US012788468B2

(12) United States Patent
Scheib

(10) Patent No.: US 12,788,468 B2
(45) Date of Patent: Nov. 10, 2026

(54) SYSTEMS AND METHODS OF COMMUNICATING THERMAL INFORMATION FOR SURGICAL ROBOTIC DEVICES

(71) Applicant: Auris Health, Inc., Redwood City, CA (US)

(72) Inventor: Charles J. Scheib, Loveland, OH (US)

(73) Assignee: Auris Health, Inc., Santa Clara, CA (US)

(*) Notice: Subject to any disclaimer, the term of this patent is extended or adjusted under 35 U.S.C. 154(b) by 749 days.

(21) Appl. No.: 17/211,752

(22) Filed: Mar. 24, 2021

(65) Prior Publication Data

US 2021/0298815 A1 Sep. 30, 2021

Related U.S. Application Data

(60) Provisional application No. 62/994,178, filed on Mar. 24, 2020.

(51) Int. Cl.

*A61B 18/00* (2006.01)
*A61B 1/00* (2006.01)
(Continued)

(52) U.S. Cl.

CPC ............ *A61B 18/12* (2013.01); *A61B 1/0005* (2013.01); *A61B 18/085* (2013.01); *A61B 34/25* (2016.02);
(Continued)

(58) Field of Classification Search

CPC ... A61B 1/0005; A61B 1/2676; A61B 1/2736; A61B 18/085; A61B 34/25; A61B 34/37;
(Continued)

(56) References Cited

U.S. PATENT DOCUMENTS

| | | | |
|---|---|---|---|
| 4,771,262 | A | 9/1988 | Reuss |
| 4,896,554 | A | 1/1990 | Culver |

(Continued)

FOREIGN PATENT DOCUMENTS

| | | |
|---|---|---|
| EP | 1800593 | 6/2007 |
| EP | 1109497 | 5/2009 |

(Continued)

OTHER PUBLICATIONS

International Search Report and Written Opinion for Application No. PCT/IB2021/050252, dated Apr. 15, 2021, 11 pages.

(Continued)

*Primary Examiner* — Jaymi E Della
(74) *Attorney, Agent, or Firm* — FBT GIBBONS LLP

(57) ABSTRACT

A medical system includes a thermal instrument, one or more processors, and memory. The medical system receives a user input for selecting a desired mode of two or more predefined modes, and places the medical system in the desired mode of the two or more predefined modes based on the user input. While the medical system is in a first mode of the two or more predefined modes, one or more signals for providing a feedback signal to a user are sent. The one or more signals are based on a temperature of a thermal instrument and a distance between the thermal instrument and a secondary object.

12 Claims, 45 Drawing Sheets

(51) Int. Cl.

*A61B 18/08* (2006.01)
*A61B 18/12* (2006.01)
*A61B 34/00* (2016.01)
*A61B 34/37* (2016.01)
*G01S 17/08* (2006.01)
*G06T 7/521* (2017.01)
*A61B 17/00* (2006.01)

(52) U.S. Cl.

CPC .............. *A61B 34/37* (2016.02); *A61B 34/76* (2016.02); *G01S 17/08* (2013.01); *G06T 7/521* (2017.01); *A61B 1/00059* (2013.01); *A61B 2017/00084* (2013.01); *A61B 2017/00115* (2013.01); *A61B 2018/00595* (2013.01); *A61B 2018/0063* (2013.01); *A61B 2018/00636* (2013.01); *A61B 2018/00666* (2013.01); *A61B 2018/00678* (2013.01); *A61B 2018/00714* (2013.01); *A61B 2018/00761* (2013.01); *A61B 2018/00791* (2013.01); *A61B 2018/00821* (2013.01); *A61B 2018/00898* (2013.01); *A61B 2018/00982* (2013.01); *A61B 2560/0487* (2013.01); *A61B 2562/0271* (2013.01); *G06T 2207/10028* (2013.01); *G06T 2207/30004* (2013.01)

(58) Field of Classification Search

CPC .......... A61B 34/76; A61B 2017/00084; A61B 2017/00115; A61B 2018/00595; A61B 2018/0063; A61B 2018/00678; A61B 2018/00714; A61B 2018/00761; A61B 2018/00791; A61B 2018/00821; A61B 2018/00898; A61B 2560/0487; A61B 2562/0271; A61B 1/00097; A61B 1/313; A61B 90/36; A61B 2018/00404; A61B 2018/00589; A61B 90/94; A61B 2017/00119; A61B 2034/302; A61B 18/12; A61B 1/00059; A61B 2018/00636; A61B 2018/00666; A61B 2090/365; G01S 17/08; G06T 7/521; G06T 2207/10028; G06T 2207/30004

See application file for complete search history.

(56) References Cited

U.S. PATENT DOCUMENTS

| | | | |
|---|---|---|---|
| 5,008,528 | A | 4/1991 | Duchon |
| 5,176,310 | A | 1/1993 | Akiyama et al. |
| 5,280,781 | A | 1/1994 | Oku |
| 5,499,632 | A | 3/1996 | Hill et al. |
| 5,524,180 | A | 6/1996 | Wang et al. |
| 5,526,812 | A | 6/1996 | Dumoulin et al. |
| 5,762,458 | A | 6/1998 | Wang et al. |
| 5,831,614 | A | 11/1998 | Tognazzini et al. |
| 5,899,851 | A | 5/1999 | Koninckx |
| 5,963,770 | A | 10/1999 | Eakin |
| 6,007,550 | A | 12/1999 | Wang et al. |
| 6,016,439 | A | 1/2000 | Acker |
| 6,038,467 | A | 3/2000 | De Bliek et al. |
| 6,096,004 | A | 8/2000 | Meglan et al. |
| 6,425,865 | B1 | 7/2002 | Salcudean et al. |
| 6,466,198 | B1 | 10/2002 | Feinstein |
| 6,468,265 | B1 | 10/2002 | Evans et al. |
| 6,490,467 | B1 | 12/2002 | Bucholz |
| 6,516,421 | B1 | 2/2003 | Peters |
| 6,690,964 | B2 | 2/2004 | Beiger et al. |
| 6,856,827 | B2 | 2/2005 | Seeley et al. |
| 6,933,469 | B2 | 8/2005 | Ellis et al. |
| 7,206,627 | B2 | 4/2007 | Abovitz |
| 7,594,925 | B2 | 9/2009 | Danek |
| 8,003,941 | B1 | 8/2011 | Heinke et al. |
| 8,180,114 | B2 | 5/2012 | Nishihara et al. |
| 8,577,650 | B2 | 11/2013 | Baker et al. |
| 8,716,973 | B1 | 5/2014 | Lammertse |
| 8,718,837 | B2 | 5/2014 | Wang et al. |
| 8,971,597 | B2 | 3/2015 | Zhao et al. |
| 9,011,427 | B2 | 4/2015 | Price et al. |
| 9,241,767 | B2 | 1/2016 | Prisco et al. |
| 9,283,046 | B2 | 3/2016 | Walker et al. |
| 9,304,590 | B2 | 4/2016 | Joshi et al. |
| 9,498,291 | B2 | 11/2016 | Balaji et al. |
| 9,503,681 | B1 | 11/2016 | Popescu et al. |
| 9,504,604 | B2 | 11/2016 | Alvarez |
| 9,561,019 | B2 | 2/2017 | Mihailescu et al. |
| 9,561,083 | B2 | 2/2017 | Yu et al. |
| 9,566,414 | B2 | 2/2017 | Wong et al. |
| 9,622,827 | B2 | 4/2017 | Yu et al. |
| 9,636,184 | B2 | 5/2017 | Lee et al. |
| 9,713,509 | B2 | 7/2017 | Schuh et al. |
| 9,727,963 | B2 | 8/2017 | Mintz et al. |
| 9,737,371 | B2 | 8/2017 | Romo et al. |
| 9,737,373 | B2 | 8/2017 | Schuh |
| 9,744,335 | B2 | 8/2017 | Jiang |
| 9,763,741 | B2 | 9/2017 | Alvarez et al. |
| 9,770,216 | B2 | 9/2017 | Brown et al. |
| 9,788,910 | B2 | 10/2017 | Schuh |
| 9,827,061 | B2 | 11/2017 | Balaji et al. |
| 9,844,412 | B2 | 12/2017 | Bogusky et al. |
| 9,867,635 | B2 | 1/2018 | Alvarez et al. |
| 9,918,681 | B2 | 3/2018 | Wallace et al. |
| 9,931,025 | B1 | 4/2018 | Graetzel et al. |
| 9,949,749 | B2 | 4/2018 | Noonan et al. |
| 9,955,986 | B2 | 5/2018 | Shah |
| 9,962,228 | B2 | 5/2018 | Schuh et al. |
| 9,980,785 | B2 | 5/2018 | Schuh |
| 9,993,313 | B2 | 6/2018 | Schuh et al. |
| 10,016,900 | B1 | 7/2018 | Meyer et al. |
| 10,022,192 | B1 | 7/2018 | Ummalaneni |
| 10,028,789 | B2 | 7/2018 | Quaid et al. |
| 10,080,576 | B2 | 9/2018 | Romo et al. |
| 10,123,843 | B2 | 11/2018 | Wong et al. |
| 10,130,427 | B2 | 11/2018 | Tanner et al. |
| 10,136,959 | B2 | 11/2018 | Mintz et al. |
| 10,145,747 | B1 | 12/2018 | Un et al. |
| 10,149,720 | B2 | 12/2018 | Romo |
| 10,159,532 | B1 | 12/2018 | Ummalaneni et al. |
| 10,159,533 | B2 | 12/2018 | Moll et al. |
| 10,169,875 | B2 | 1/2019 | Mintz et al. |
| 10,206,746 | B2 | 2/2019 | Walker et al. |
| 10,219,874 | B2 | 3/2019 | Yu et al. |
| 10,225,492 | B1 | 3/2019 | Steffanson et al. |
| 10,231,793 | B2 | 3/2019 | Romo |
| 10,231,867 | B2 | 3/2019 | Alvarez et al. |
| 10,244,926 | B2 | 4/2019 | Noonan et al. |
| 10,282,064 | B2 | 5/2019 | Vahala et al. |
| 10,285,574 | B2 | 5/2019 | Landey et al. |
| 10,299,870 | B2 | 5/2019 | Connolly et al. |
| 10,314,463 | B2 | 6/2019 | Agrawal et al. |
| 10,346,976 | B2 | 7/2019 | Averbuch |
| 10,383,765 | B2 | 8/2019 | Alvarez et al. |
| 10,398,518 | B2 | 9/2019 | Yu et al. |
| 10,405,939 | B2 | 9/2019 | Romo et al. |
| 10,405,940 | B2 | 9/2019 | Romo |
| 10,426,559 | B2 | 10/2019 | Graetzel et al. |
| 10,426,661 | B2 | 10/2019 | Kintz |
| 10,434,660 | B2 | 10/2019 | Meyer |
| 10,464,209 | B2 | 11/2019 | Ho et al. |
| 10,470,830 | B2 | 11/2019 | Hill |
| 10,482,599 | B2 | 11/2019 | Mintz et al. |
| 10,493,241 | B2 | 12/2019 | Jiang |
| 10,500,001 | B2 | 12/2019 | Yu et al. |
| 10,517,692 | B2 | 12/2019 | Eyre et al. |
| 10,524,866 | B2 | 1/2020 | Srinivasan |
| 10,539,478 | B2 | 1/2020 | Lin |
| 10,543,048 | B2 | 1/2020 | Noonan et al. |
| 10,555,778 | B2 | 2/2020 | Ummalaneni et al. |
| 10,631,949 | B2 | 4/2020 | Schuh et al. |
| 10,639,108 | B2 | 5/2020 | Romo et al. |
| 10,639,109 | B2 | 5/2020 | Bovay et al. |
| 10,639,114 | B2 | 5/2020 | Schuh |

(56) References Cited

U.S. PATENT DOCUMENTS 10,667,871 B2 6/2020 Romo et al.
10,667,875 B2 6/2020 DeFonzo
10,675,101 B2 6/2020 Walker et al.
10,682,189 B2 6/2020 Schuh et al.
10,688,283 B2 6/2020 Wong et al.
10,701,290 B2 6/2020 Steffanson et al.
10,702,348 B2 7/2020 Moll et al.
10,716,461 B2 7/2020 Jenkins
10,743,751 B2 8/2020 Landey et al.
10,744,035 B2 8/2020 Alvarez et al.
10,751,140 B2 8/2020 Wallace et al.
10,765,303 B2 9/2020 Graetzel et al.
10,765,487 B2 9/2020 Ho
10,779,898 B2 9/2020 Hill
10,786,329 B2 9/2020 Schuh et al.
10,786,432 B2 9/2020 Jornitz et al.
10,792,464 B2 10/2020 Romo et al.
10,792,466 B2 10/2020 Landey et al.
10,806,531 B2 10/2020 Berry et al.
10,813,539 B2 10/2020 Graetzel et al.
10,814,101 B2 10/2020 Jiang
10,820,947 B2 11/2020 Julian
10,820,954 B2 11/2020 Marsot et al.
10,827,913 B2 11/2020 Ummalaneni et al.
10,828,118 B2 11/2020 Schuh et al.
10,835,153 B2 11/2020 Rafii-Tari et al.
10,849,702 B2 12/2020 Hsu et al.
10,850,013 B2 12/2020 Hsu
10,881,280 B2 1/2021 Baez
11,304,686 B2 4/2022 Manzke et al.
2002/0077533 A1 6/2002 Bieger et al.
2002/0082612 A1 6/2002 Moll et al.
2002/0120188 A1 8/2002 Brock et al.
2002/0161280 A1 10/2002 Chatenever et al.
2002/0173878 A1 11/2002 Watanabe
2003/0218003 A1* 11/2003 Ellis ......................... H05B 3/36
219/494
2004/0047044 A1 3/2004 Dalton
2004/0263535 A1 12/2004 Birkenbach et al.
2005/0043718 A1 2/2005 Madhani
2005/0085714 A1 4/2005 Foley et al.
2005/0171583 A1* 8/2005 Mosher .............. A61B 18/1485
607/113
2005/0193451 A1 9/2005 Quistgaard et al.
2005/0222554 A1 10/2005 Wallace et al.
2006/0079745 A1 4/2006 Viswanathan et al.
2006/0095022 A1 5/2006 Moll et al.
2006/0106375 A1* 5/2006 Werneth ............. A61B 18/1492
606/41
2006/0173290 A1 8/2006 Lavallee et al.
2006/0200026 A1 9/2006 Wallace et al.
2007/0083098 A1 4/2007 Stern et al.
2007/0138992 A1 6/2007 Prisco et al.
2007/0144298 A1 6/2007 Miller
2007/0185486 A1 8/2007 Hauck et al.
2008/0027313 A1 1/2008 Shachar
2008/0033418 A1* 2/2008 Nields .................... A61B 18/18
606/41
2008/0033442 A1 2/2008 Amoit
2008/0077128 A1 3/2008 Woloszko et al.
2008/0082109 A1 4/2008 Moll et al.
2008/0097465 A1 4/2008 Rollins et al.
2008/0108870 A1 5/2008 Wiita et al.
2008/0140087 A1 6/2008 Barbagli et al.
2008/0183068 A1 7/2008 Carls et al.
2008/0183188 A1 7/2008 Carls et al.
2008/0306490 A1 12/2008 Lakin et al.
2009/0248036 A1 10/2009 Hoffman et al.
2009/0259230 A1 10/2009 Khadem
2009/0259412 A1 10/2009 Brogardh
2009/0326322 A1 12/2009 Diolaiti
2009/0326556 A1 12/2009 Diolaiti et al.
2010/0019890 A1 1/2010 Helmer et al.
2010/0039506 A1 2/2010 Sarvestani et al.
2010/0076263 A1 3/2010 Tanaka
2010/0121269 A1 5/2010 Goldenberg
2010/0125284 A1 5/2010 Tanner et al.
2010/0161129 A1 6/2010 Costa et al.
2010/0204613 A1 8/2010 Rollins et al.
2010/0225209 A1 9/2010 Goldberg
2010/0328455 A1 12/2010 Nam et al.
2011/0021926 A1 1/2011 Spencer
2011/0113852 A1 5/2011 Prisco
2011/0118748 A1 5/2011 Itkowitz
2011/0118752 A1 5/2011 Itkowitz et al.
2011/0118753 A1 5/2011 Itkowitz et al.
2011/0130718 A1 6/2011 Kidd et al.
2011/0196199 A1 8/2011 Donhowe et al.
2011/0235855 A1 9/2011 Smith
2011/0238010 A1 9/2011 Kirschenman et al.
2011/0248987 A1 10/2011 Mitchell
2011/0276058 A1 11/2011 Choi et al.
2011/0306873 A1 12/2011 Shenai et al.
2012/0059392 A1 3/2012 Diolaiti
2012/0071752 A1 3/2012 Sewell
2012/0071891 A1 3/2012 Itkowitz et al.
2012/0071892 A1 3/2012 Itkowitz et al.
2012/0071894 A1 3/2012 Tanner et al.
2012/0075638 A1 3/2012 Rollins et al.
2012/0078053 A1 3/2012 Phee et al.
2012/0103123 A1 5/2012 Mcinroy et al.
2012/0158011 A1 6/2012 Sandhu
2012/0203067 A1 8/2012 Higgins et al.
2012/0253276 A1 10/2012 Govari et al.
2012/0296161 A1 11/2012 Wallace et al.
2012/0314022 A1 12/2012 Jo
2013/0018306 A1 1/2013 Ludwin
2013/0060146 A1 3/2013 Yang et al.
2013/0165854 A1 6/2013 Sandhu et al.
2013/0199540 A1* 8/2013 Buske ....................... H05H 1/42
128/845
2013/0245375 A1 9/2013 DiMaio et al.
2013/0317519 A1 11/2013 Romo et al.
2014/0107666 A1 4/2014 Madhani
2014/0111457 A1 4/2014 Briden et al.
2014/0142591 A1 5/2014 Alvarez et al.
2014/0222204 A1 8/2014 Kawashima
2014/0243614 A1* 8/2014 Rothberg ............. A61B 8/5207
600/407
2014/0276392 A1 9/2014 Wong et al.
2014/0277333 A1 9/2014 Lewis et al.
2014/0357984 A1 12/2014 Wallace et al.
2015/0018622 A1 1/2015 Tesar et al.
2015/0094710 A1 4/2015 Edwards et al.
2015/0105747 A1 4/2015 Rollins et al.
2015/0157191 A1 6/2015 Phee et al.
2015/0169836 A1 6/2015 Vahala et al.
2015/0224845 A1 8/2015 Anderson et al.
2015/0265807 A1 9/2015 Park et al.
2015/0290454 A1 10/2015 Tyler et al.
2015/0375399 A1 12/2015 Chiu et al.
2016/0026253 A1 1/2016 Bradski et al.
2016/0059412 A1 3/2016 Oleynik
2016/0098095 A1 4/2016 Gonzalez-Banos et al.
2016/0183841 A1 6/2016 Duindam et al.
2016/0213436 A1 7/2016 Inoue
2016/0213884 A1 7/2016 Park
2016/0256069 A1 9/2016 Jenkins
2016/0270865 A1 9/2016 Landey et al.
2016/0287279 A1 10/2016 Bovay et al.
2016/0314710 A1 10/2016 Jarc
2016/0314716 A1 10/2016 Grubbs
2016/0314717 A1 10/2016 Grubbs
2016/0324580 A1 11/2016 Esterberg et al.
2017/0007337 A1 1/2017 Dan
2017/0100091 A1* 4/2017 Eigil ...................... A61B 8/085
2017/0113070 A1* 4/2017 Tanttu ...................... A61N 7/02
2017/0143429 A1 5/2017 Richmond et al.
2017/0172664 A1 6/2017 Weingarten et al.
2017/0202627 A1 7/2017 Sramek et al.
2017/0209073 A1 7/2017 Sramek et al.
2017/0290631 A1 10/2017 Lee et al.
2018/0025666 A1 1/2018 Ho et al.
2018/0049832 A1* 2/2018 Eckert .................... A61B 34/30

(56) References Cited

U.S. PATENT DOCUMENTS

| | | | | |
|---|---|---|---|---|
| 2018/0078321 | A1 | 3/2018 | Liao | |
| 2018/0079090 | A1 | 3/2018 | Koenig et al. | |
| 2018/0168734 | A1* | 6/2018 | Strobl | G01J 5/0803 |
| 2018/0221038 | A1 | 8/2018 | Noonan et al. | |
| 2018/0221039 | A1 | 8/2018 | Shah | |
| 2018/0235509 | A1* | 8/2018 | Doron | A61B 5/287 |
| 2018/0279852 | A1 | 10/2018 | Rafii-Tari et al. | |
| 2018/0289431 | A1 | 10/2018 | Draper et al. | |
| 2018/0325499 | A1 | 11/2018 | Landey et al. | |
| 2018/0360435 | A1 | 12/2018 | Romo | |
| 2019/0000559 | A1 | 1/2019 | Berman et al. | |
| 2019/0000560 | A1 | 1/2019 | Berman et al. | |
| 2019/0000576 | A1 | 1/2019 | Mintz et al. | |
| 2019/0090969 | A1 | 3/2019 | Jarc et al. | |
| 2019/0110839 | A1 | 4/2019 | Rafii-Tari et al. | |
| 2019/0151032 | A1 | 5/2019 | Mustufa et al. | |
| 2019/0151148 | A1 | 5/2019 | Alvarez et al. | |
| 2019/0167366 | A1 | 6/2019 | Ummalaneni | |
| 2019/0175009 | A1 | 6/2019 | Mintz | |
| 2019/0183585 | A1 | 6/2019 | Rafii-Tari et al. | |
| 2019/0183587 | A1 | 6/2019 | Rafii-Tari et al. | |
| 2019/0216548 | A1 | 7/2019 | Ummalaneni | |
| 2019/0223974 | A1 | 7/2019 | Romo | |
| 2019/0262086 | A1 | 8/2019 | Connolly et al. | |
| 2019/0269468 | A1 | 9/2019 | Hsu et al. | |
| 2019/0274764 | A1 | 9/2019 | Romo | |
| 2019/0290109 | A1 | 9/2019 | Agrawal et al. | |
| 2019/0290215 | A1 | 9/2019 | Gilbert | |
| 2019/0298460 | A1 | 10/2019 | Al-Jadda | |
| 2019/0298465 | A1 | 10/2019 | Chin | |
| 2019/0336238 | A1 | 11/2019 | Yu | |
| 2019/0365201 | A1 | 12/2019 | Noonan et al. | |
| 2019/0365209 | A1 | 12/2019 | Ye et al. | |
| 2019/0365479 | A1 | 12/2019 | Rafii-Tari | |
| 2019/0365486 | A1 | 12/2019 | Srinivasan et al. | |
| 2019/0371012 | A1 | 12/2019 | Flexman | |
| 2019/0375383 | A1 | 12/2019 | Alvarez | |
| 2019/0380787 | A1 | 12/2019 | Ye | |
| 2019/0380797 | A1 | 12/2019 | Yu | |
| 2020/0000533 | A1 | 1/2020 | Schuh | |
| 2020/0015806 | A1 | 1/2020 | Scheib et al. | |
| 2020/0015905 | A1* | 1/2020 | Scheib | G01S 17/36 |
| 2020/0038121 | A1 | 2/2020 | Yang et al. | |
| 2020/0038123 | A1 | 2/2020 | Graetzel | |
| 2020/0039086 | A1 | 2/2020 | Meyer | |
| 2020/0046434 | A1 | 2/2020 | Graetzel | |
| 2020/0054385 | A1* | 2/2020 | Weinkam | A61B 18/04 |
| 2020/0069192 | A1 | 3/2020 | Sanborn et al. | |
| 2020/0085516 | A1 | 3/2020 | DeFonzo | |
| 2020/0093549 | A1 | 3/2020 | Chin | |
| 2020/0093554 | A1 | 3/2020 | Schuh | |
| 2020/0100855 | A1 | 4/2020 | Leparmentier | |
| 2020/0107894 | A1 | 4/2020 | Wallace | |
| 2020/0121502 | A1 | 4/2020 | Kinlz | |
| 2020/0146769 | A1 | 5/2020 | Eyre | |
| 2020/0170720 | A1 | 6/2020 | Ummalaneni | |
| 2020/0171660 | A1 | 6/2020 | Ho | |
| 2020/0188043 | A1 | 6/2020 | Yu | |
| 2020/0197112 | A1 | 6/2020 | Chin | |
| 2020/0206472 | A1 | 7/2020 | Ma | |
| 2020/0217733 | A1 | 7/2020 | Lin | |
| 2020/0222134 | A1 | 7/2020 | Schuh | |
| 2020/0237458 | A1 | 7/2020 | DeFonzo | |
| 2020/0261172 | A1 | 8/2020 | Romo | |
| 2020/0268459 | A1 | 8/2020 | Noonan et al. | |
| 2020/0268460 | A1 | 8/2020 | Tse | |
| 2020/0281787 | A1 | 9/2020 | Ruiz | |
| 2020/0297437 | A1 | 9/2020 | Schuh | |
| 2020/0297444 | A1 | 9/2020 | Camarillo | |
| 2020/0305983 | A1 | 10/2020 | Yampolsky | |
| 2020/0305989 | A1 | 10/2020 | Schuh | |
| 2020/0305992 | A1 | 10/2020 | Schuh | |
| 2020/0315717 | A1 | 10/2020 | Bovay | |
| 2020/0315723 | A1 | 10/2020 | Hassan | |
| 2020/0323596 | A1 | 10/2020 | Moll | |
| 2020/0330167 | A1 | 10/2020 | Romo | |
| 2020/0345216 | A1 | 11/2020 | Jenkins | |
| 2020/0345432 | A1 | 11/2020 | Walker | |
| 2020/0352420 | A1 | 11/2020 | Graetzel | |
| 2020/0360183 | A1 | 11/2020 | Alvarez | |
| 2020/0360659 | A1 | 11/2020 | Wong | |
| 2020/0367726 | A1 | 11/2020 | Landey et al. | |
| 2020/0367981 | A1 | 11/2020 | Ho et al. | |
| 2020/0375678 | A1 | 12/2020 | Wallace | |
| 2020/0405317 | A1 | 12/2020 | Wallace | |
| 2020/0405411 | A1 | 12/2020 | Draper et al. | |
| 2020/0405419 | A1 | 12/2020 | Mao | |
| 2020/0405420 | A1 | 12/2020 | Purohit | |
| 2020/0405423 | A1 | 12/2020 | Schuh | |
| 2020/0405424 | A1 | 12/2020 | Schuh | |
| 2020/0405434 | A1 | 12/2020 | Schuh | |
| 2020/0406002 | A1 | 12/2020 | Romo | |
| 2021/0007819 | A1 | 1/2021 | Schuh | |
| 2021/0008341 | A1 | 1/2021 | Landey et al. | |
| 2022/0379463 | A1 | 12/2022 | Hansen | |

FOREIGN PATENT DOCUMENTS

| | | |
|---|---|---|
| EP | 2158834 | 3/2010 |
| JP | 2006-326128 A | 12/2006 |
| WO | WO-08/049088 | 4/2008 |
| WO | WO-10/025522 | 3/2010 |
| WO | WO-17/214243 | 12/2017 |

OTHER PUBLICATIONS

Reddy et al. May 2005 P153. Porcine pulmonary vein ablation using a novel robotic catheter control system and realtime integration of CT imaging with electroanatomical mapping Hearth Rhythm, 2(5):S121.

Ren et aL 2011 Multisensor data fusion in an integrated tracking system for endoscopic surgery IEEE Transactions on Information Technology in Biomedicine 16(1):106111.

Final Office Action dated Mar. 27, 2024; U.S. Appl. No. 17/148,946, filed Jan. 14, 2021; 12 pages.

Office Action dated Feb. 27, 2024; U.S. Appl. No. 17/211,732, filed Mar. 24, 2021; 32 pages.

European Extended Search Report; Application No. 21774565.2; Mar. 19, 2024; 9 pages.

Office Action dated Oct. 30, 2023; U.S. Appl. No. 17/148,946, filed Jan. 14, 2021; 23 pages.

Chinese First Office Action and Search Report dated Jul. 18, 2025, for Application No. 202180023653.X, 12 pages.

* cited by examiner

SYSTEMS AND METHODS OF COMMUNICATING THERMAL INFORMATION FOR SURGICAL ROBOTIC DEVICES

RELATED APPLICATIONS

This application claims the benefit of, and priority to, U.S. Provisional Patent Application Ser. No. 62/994,178, filed on Mar. 24, 2020, and is related to U.S. patent application Ser. No. 17/148,946, filed on Jan. 14, 2021, which are incorporated by reference herein in their entirety.

TECHNICAL FIELD

This application is directed to robotic medical systems, and more particularly to heat indicators configured for use with robotic medical systems.

BACKGROUND

Medical procedures, such as laparoscopy or endoscopy, may involve accessing and visualizing an internal region of a patient. In a laparoscopic procedure, for example, a medical instrument can be inserted into an internal region through a laparoscopic access port. Robotically-enabled medical system can be used to perform such medical procedures. The robotically-enabled medical systems may include several robotic components, including, for example, robotic arms, robotic instrument manipulators, and robotic medical instruments, such as robotically controllable laparoscopes or endoscopes. The robotically-enabled medical systems can be controlled using a user console that may include one or more hand operated inputs as well as one or more foot operated inputs.

SUMMARY

The systems, methods and devices of this disclosure each have several innovative aspects, no single one of which is solely responsible for the desirable attributes disclosed herein.

In one aspect, a robotic medical system is provided. The robotic medical system can include a medical instrument including a distal end configured to be inserted into a patient and apply heat to tissue within the patient. The robotic medical system can further include a robotic manipulator engaged with the medical instrument and configured to operate the medical instrument. The robotic medical system can also include a temperature sensor configured to take one or more temperature readings of the medical instrument. The robotic medical system can include a viewer configured to display an image of the medical instrument and an image overlay conveying information indicative of a temperature of the medical instrument. The information conveyed by the image overlay can be based on the one or more temperature readings taken by the temperature sensor. In some configurations, the image overlay can be displayed over at least a portion of the image of the medical instrument. In some configurations, the image overlay is displayed over at least the distal end of the medical instrument of the image.

In some configurations, the medical instrument further includes a wrist. The image overlay can be displayed over at least the wrist of the medical instrument of the image. The image overlay can be displayed around at least a portion of the image of the medical instrument. The image overlay can be displayed around a second image overlay associated with the medical instrument.

The second image overlay can convey a state or an identity of the medical instrument. The image overlay can include a temperature meter indicating a temperature of the medical instrument.

The image overlay can be capable of displaying multiple colors. The multiple colors can include a first color indicating that the medical instrument is heated and a second color indicating that the medical instrument is cooled. The image overlay can display multiple colors that continually transition from the first color to the second color. The image overlay can display the first color until the medical instrument reaches a temperature threshold. The image overlay can display the second color once the medical instrument reaches the temperature threshold. In some configurations, the image overlay can include a number indicating the temperature of the medical instrument. The image overlay can include a time until the medical instrument reaches a temperature threshold.

In some configurations, the viewer is on a physician console. In some configurations, the viewer is on a tower. In some configurations, the viewer is on the medical instrument.

In some configurations, the information can be based on a direct measurement of temperature of the distal end of the medical instrument. In some configurations, the medical instrument can include a wrist. The information can be based on a direct measurement of temperature of the wrist of the medical instrument. The image overlay can convey information based on known characteristics of the medical instrument including one or more of a firing time, a thermal decay constant, and an external body temperature. In some configurations, the temperature sensor is located within the medical instrument.

In another aspect, a method of controlling a robotic medical instrument can be provided. The method can include operating the robotic medical instrument with a robotic manipulator engaged with the robotic medical instrument. The method can further include measuring a temperature at a distal end of the robotic medical instrument. The method can further include limiting a functionality of the robotic medical instrument based on the measured temperature.

In some configurations, the method can further include displaying an image of the robotic medical instrument and an image overlay that conveys information regarding the measured temperature. The functionality can be limited until the measured temperature falls below a temperature threshold. In some configurations, limiting the functionality can include limiting a speed of the robotic medical instrument. In some configurations, limiting the functionality can include preventing actuation of the robotic medical instrument. In some configurations, the method can further include generating one or more of a visual, audible, or haptic alarm to indicate the measured temperature. The alarm can indicate the temperature is above a temperature threshold.

In accordance with some embodiments, a medical system includes a thermal instrument; one or more processors; and memory storing instructions for execution by the one or more processors. The medical system receives first information indicating a temperature of the thermal instrument, receives second information indicating a distance between the thermal instrument and a secondary object, determines whether the temperature indicated by the first information satisfies a first criterion, determines whether the distance indicated by the second information satisfies a second criterion, and sends one or more signals for providing a feedback signal to a user.

In accordance with some embodiments, a non-transitory computer readable storage medium stores instructions for execution by one or more processors of a medical system. The stored instructions include instructions for, in accordance with a determination that warning criteria are satisfied, providing a warning signal to a user console, wherein the warning criteria are based on temperature information indicating a temperature of a thermal instrument and distance information indicating a distance between the thermal instrument and a secondary object.

In some embodiments, the stored instructions include instructions for determining a distance threshold based on the temperature information. Determining that the warning criteria are satisfied includes determining that the distance between the thermal instrument and the secondary object is less than the distance threshold.

In accordance with some embodiments, an electronic device includes one or more processors, and memory storing instructions for execution by the one or more processors. The electronic device receives an image of a surgical site, receives first information indicating a temperature of a thermal instrument, receives second information indicating a distance between the thermal instrument and a secondary object, generates a combined image by combining the image of the surgical site and a graphical representation based on (i) the temperature of the thermal instrument and (ii) the distance between the thermal instrument and the secondary object, and provides the combined image for display on a display device.

In some embodiments, the instructions for generating the combined image include instructions for overlaying the graphical representation on the image of the surgical site. In some embodiments, the graphical representation includes a distance indicator representing the distance between the thermal instrument and the secondary object. In some embodiments, the graphical representation includes a distance threshold indicator representing a distance threshold.

In accordance with some embodiments, a medical system includes a thermal instrument, one or more processors, and memory storing instructions for execution by the one or more processors. The medical system receives a user input for selecting a desired mode of two or more predefined modes, and places the medical system in the desired mode of the two or more predefined modes based on the user input. While the medical system is in a first mode of the two or more predefined modes, one or more signals for providing a feedback signal to a user are sent. The one or more signals are based on a temperature of a thermal instrument and a distance between the thermal instrument and a secondary object.

In accordance with some embodiments, a non-transitory computer readable storage medium stores instructions for execution by one or more processors of a medical system. The stored instructions include instructions for, while the medical system is in a first mode of two or more predefined modes: receiving first information indicating a temperature of a thermal instrument; receiving second information indicating a distance between a thermal instrument and a secondary object; determining whether the temperature of the thermal instrument exceeds a temperature threshold; determining whether the distance between the thermal instrument and the secondary object is less than a distance threshold; and in accordance with a determination that the temperature of the thermal instrument exceeds the temperature threshold and a determination that the distance between the thermal instrument and the secondary object is less than the distance threshold, sending one or more signals for providing a feedback signal indicating a thermal distance warning.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System-Cart.

Figure 1:
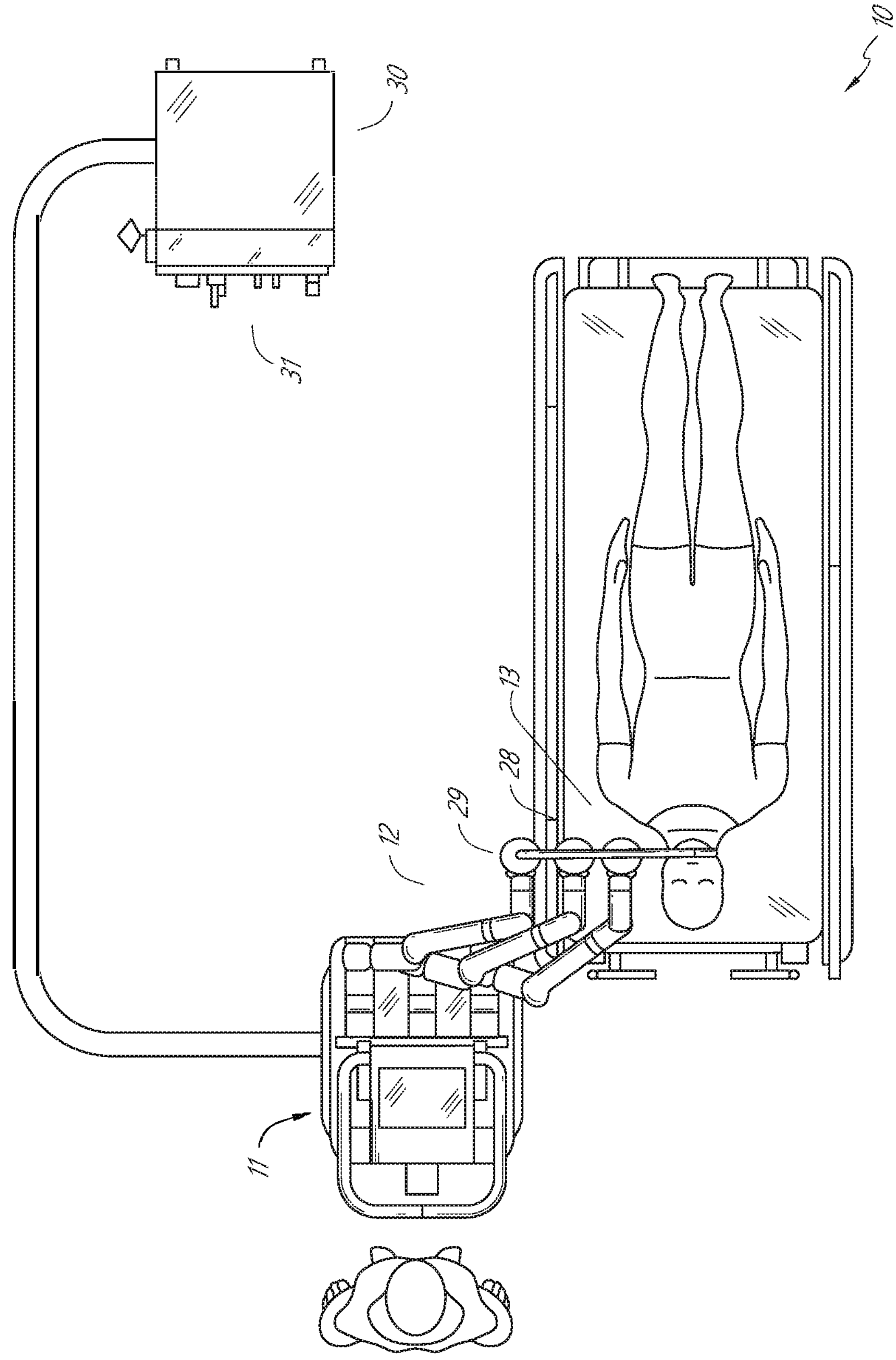
FIG. 1 illustrates an embodiment of a cart-based robotic system arranged for diagnostic and/or therapeutic bronchoscopy.
Figure 2:
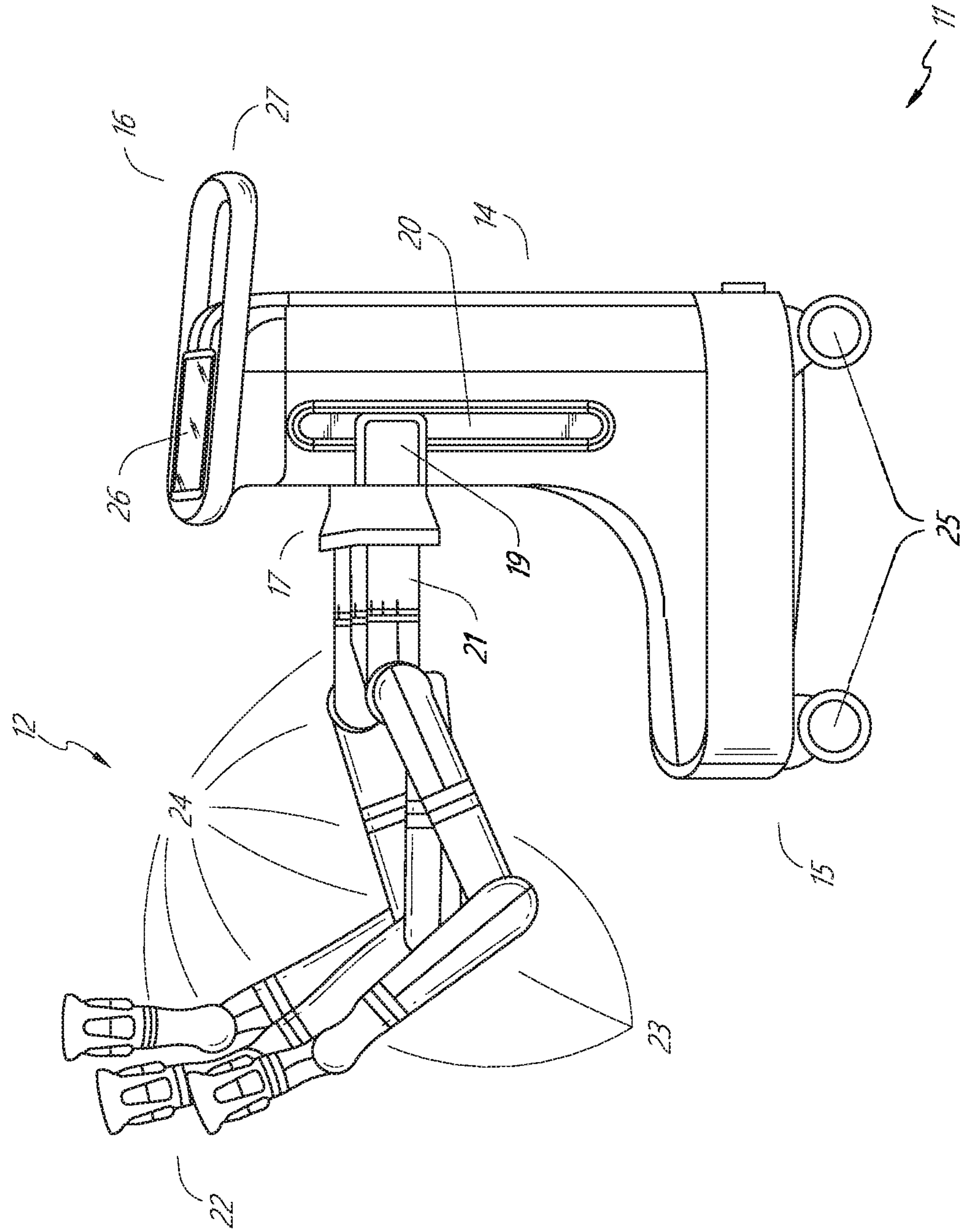
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
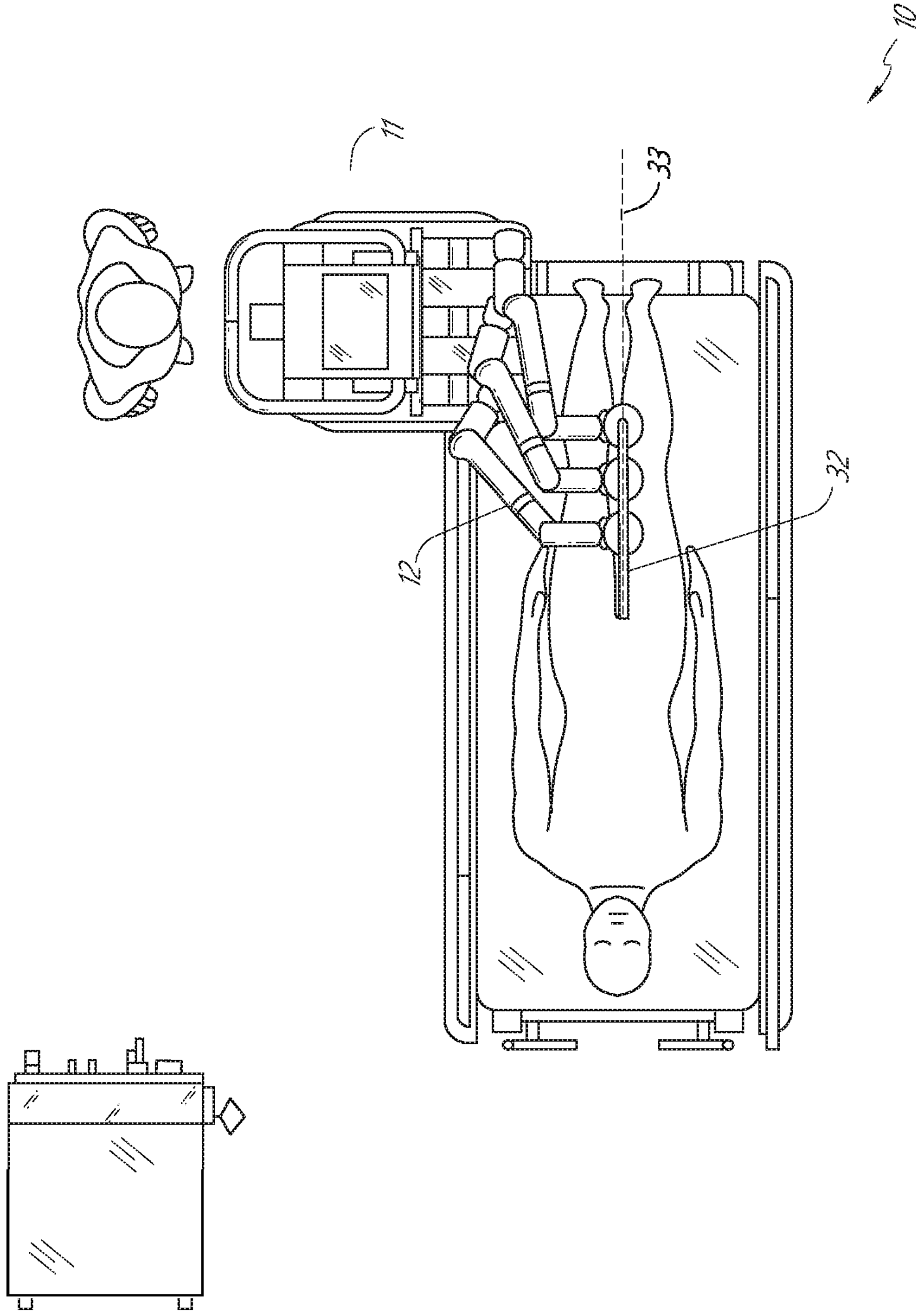
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
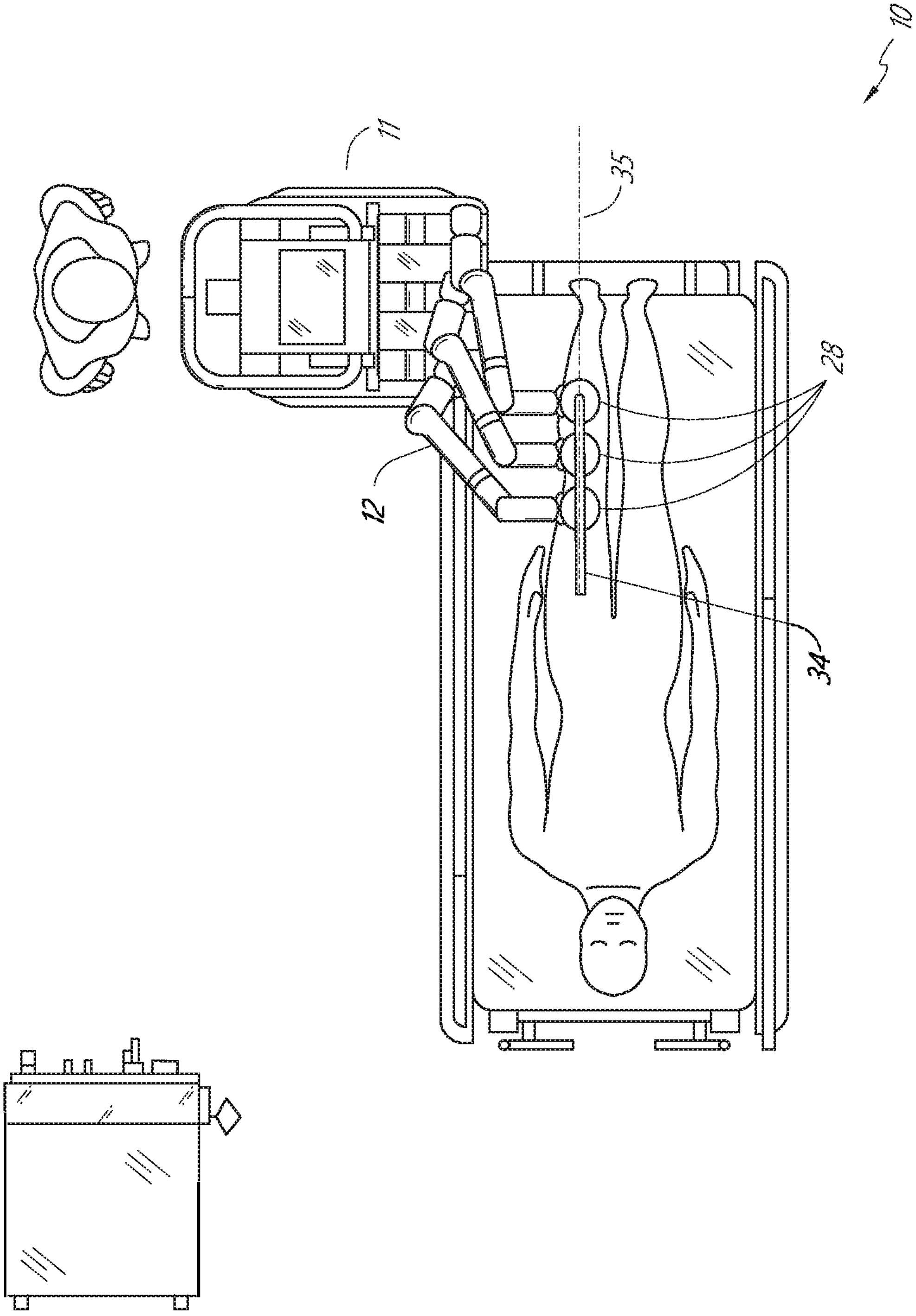
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
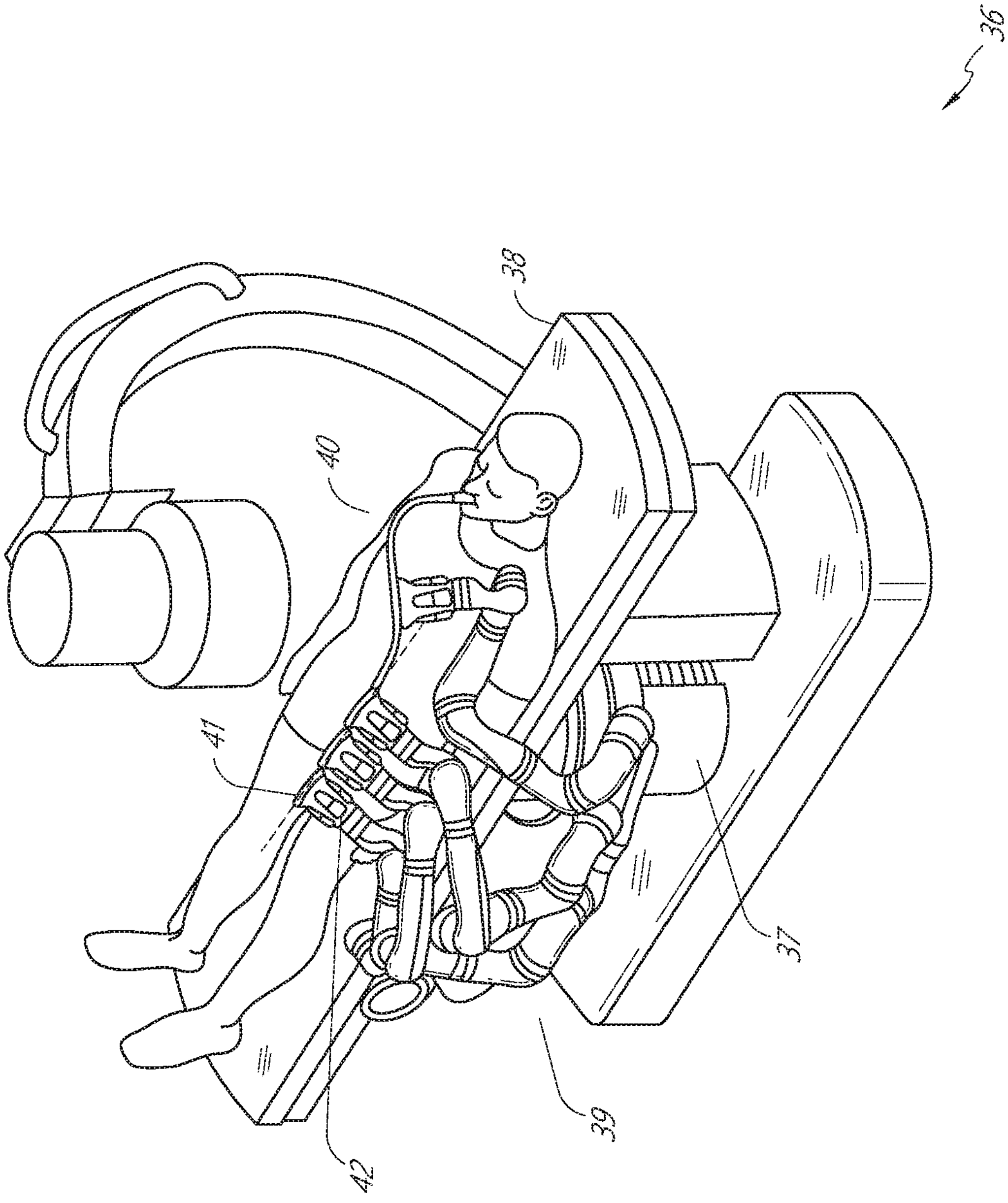
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
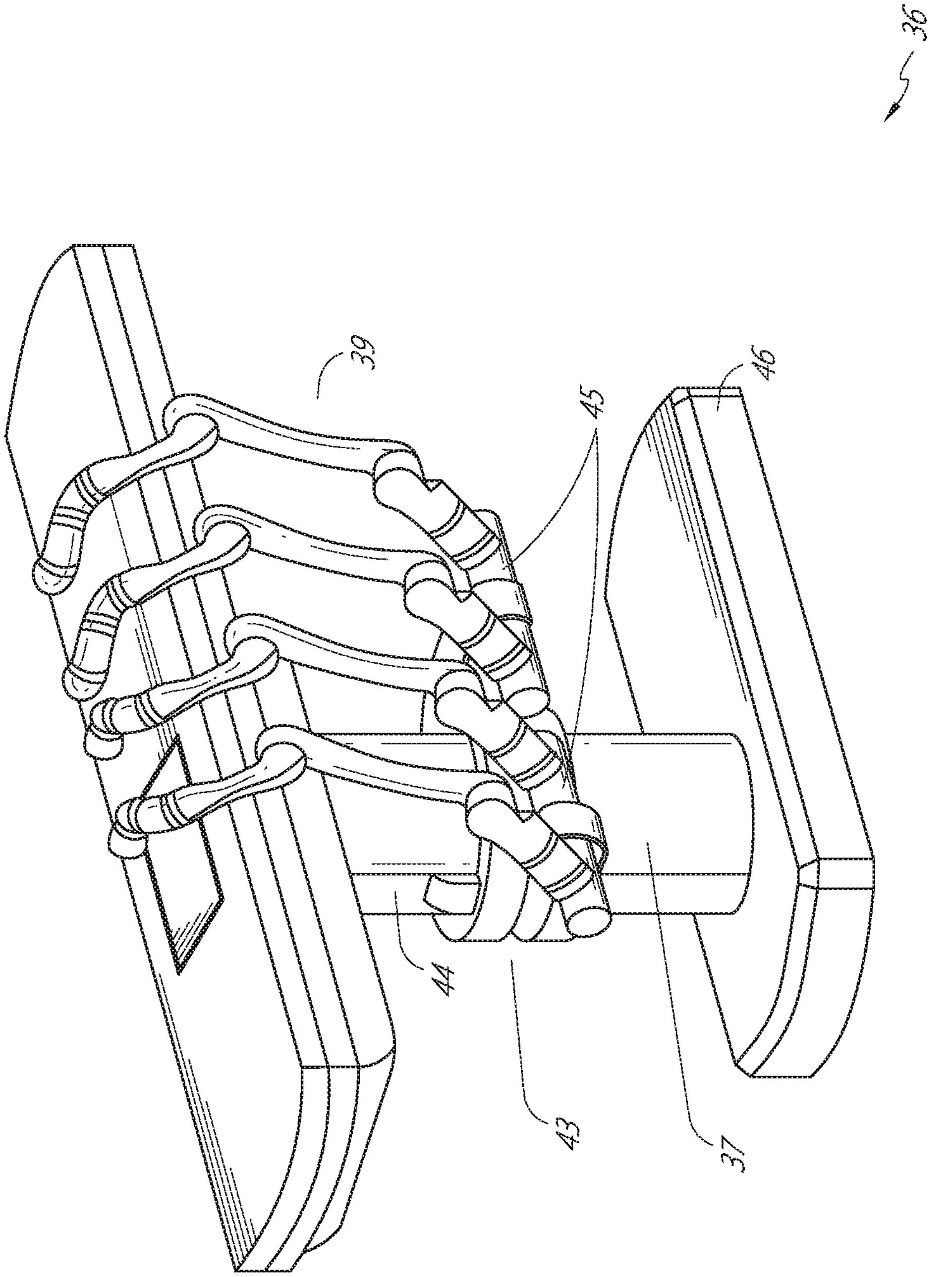
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
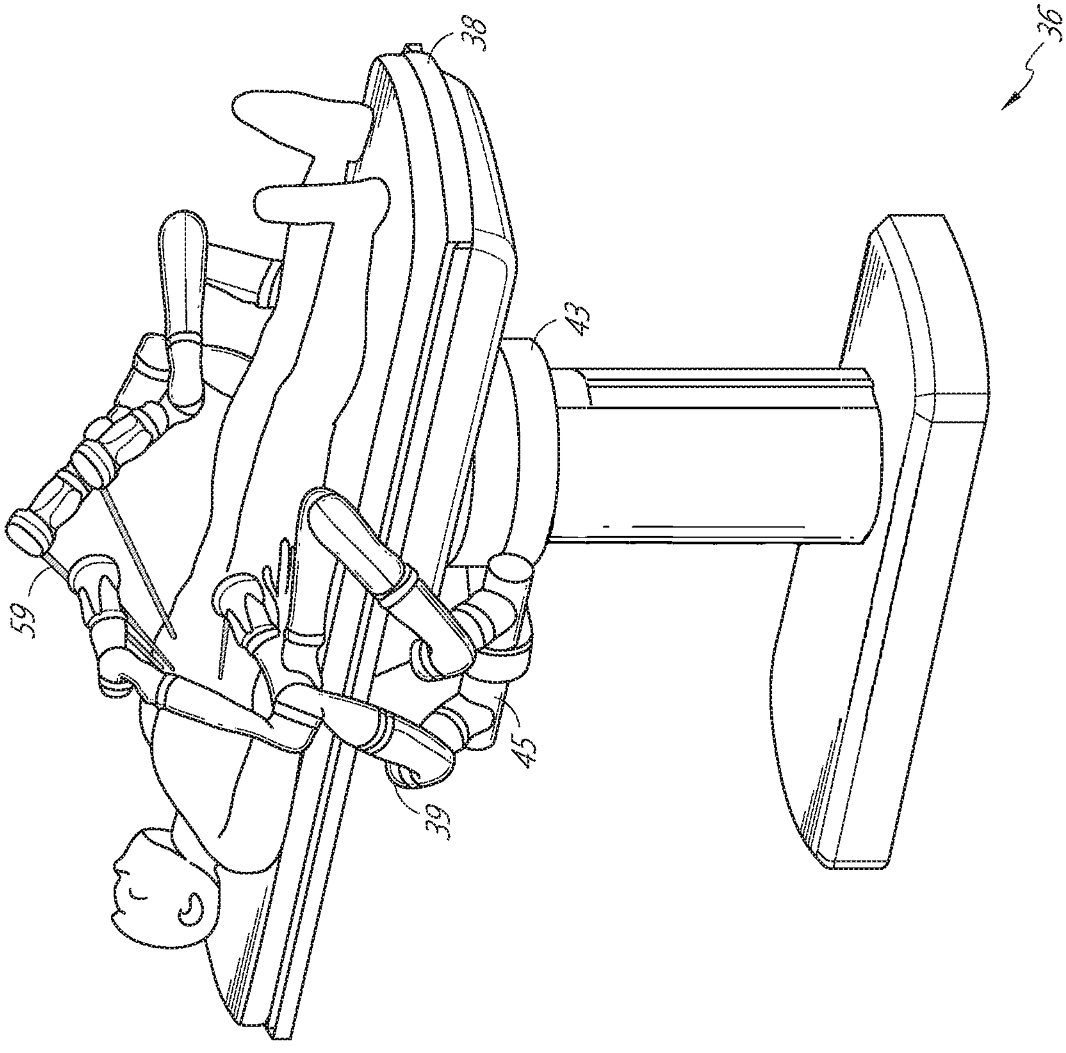
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
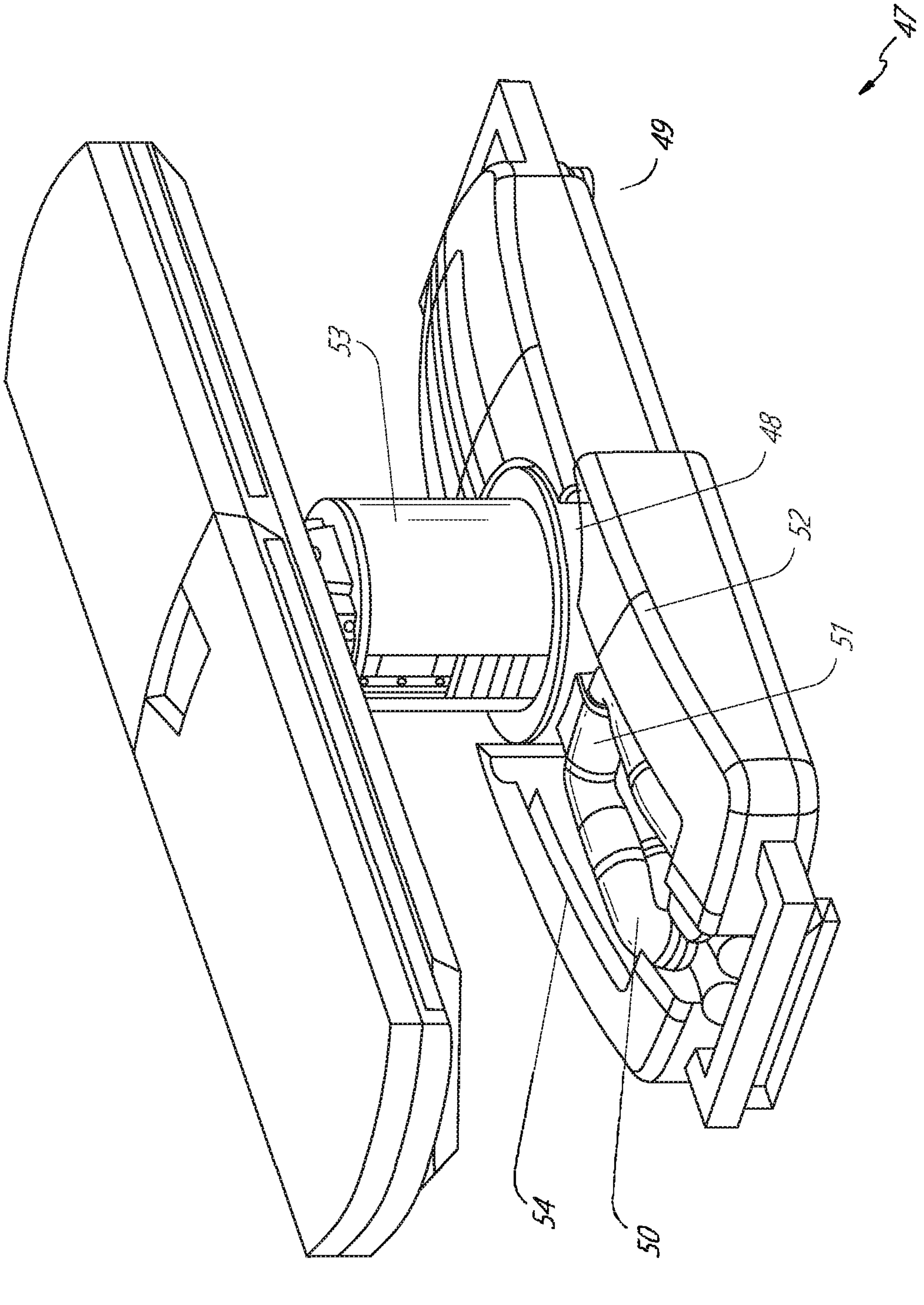
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
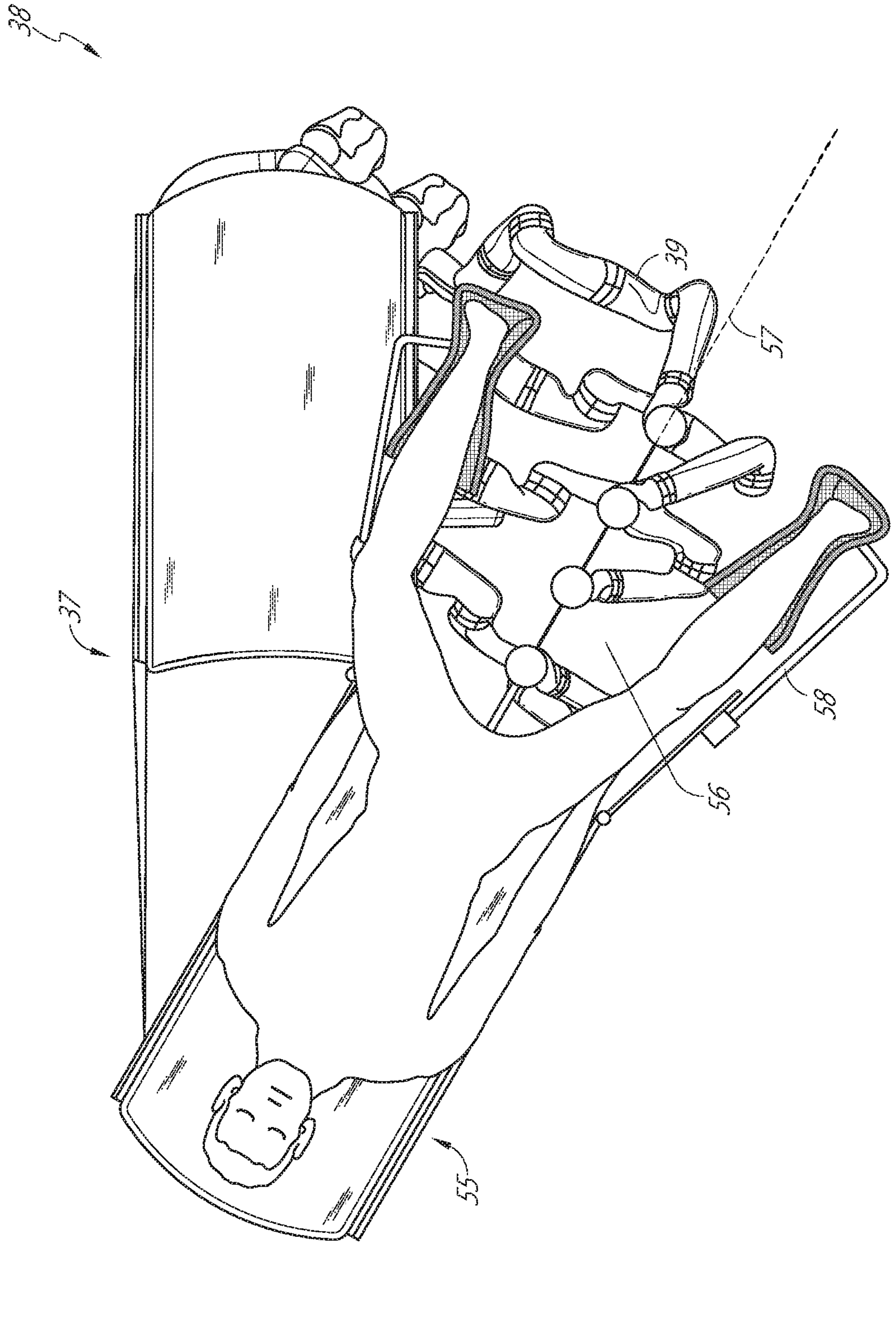
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
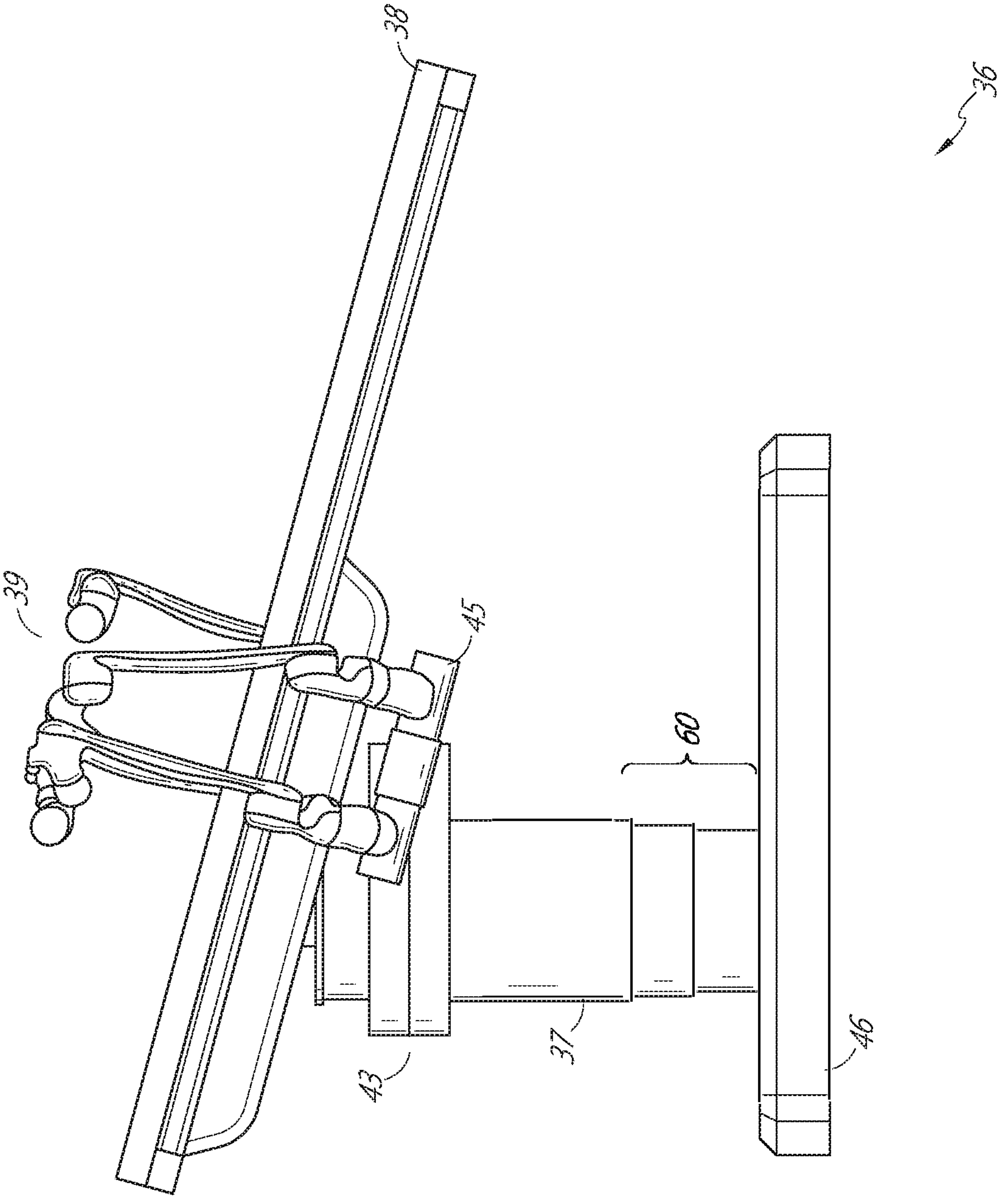
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
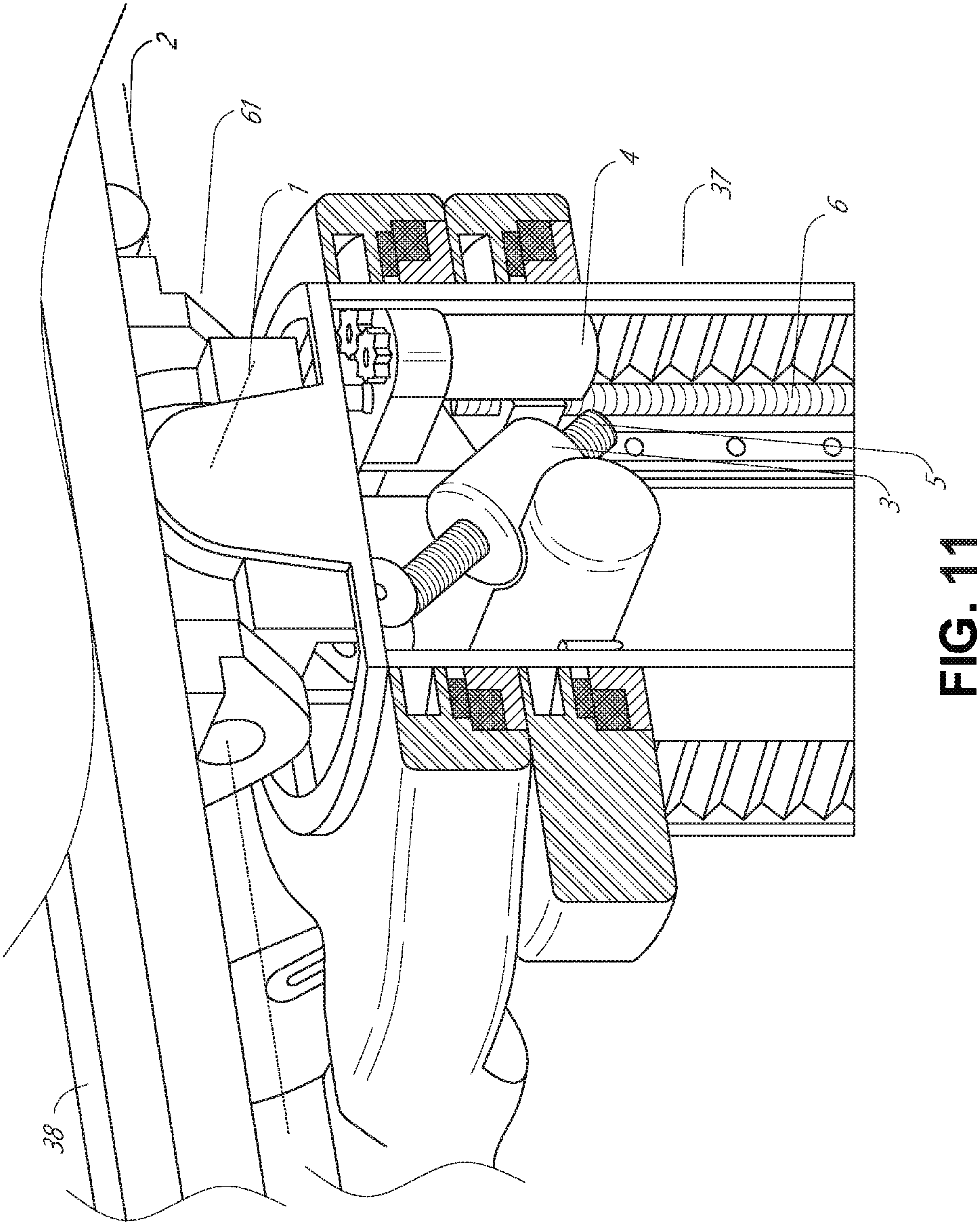
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
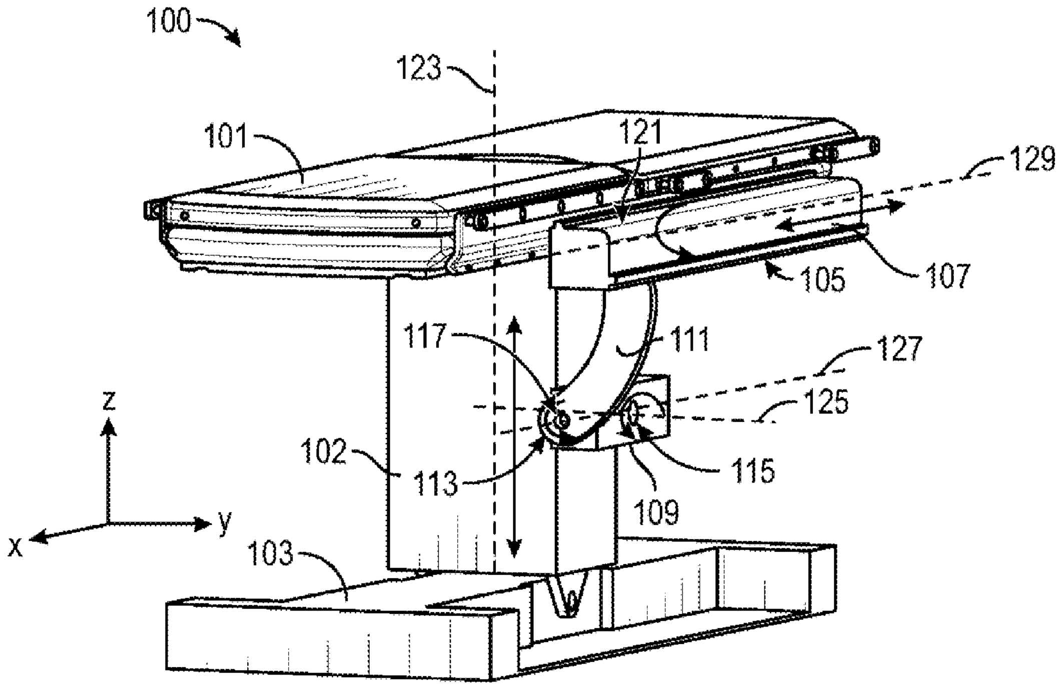
FIG. 12 illustrates an alternative embodiment of a table-based robotic system.
Figure 13:
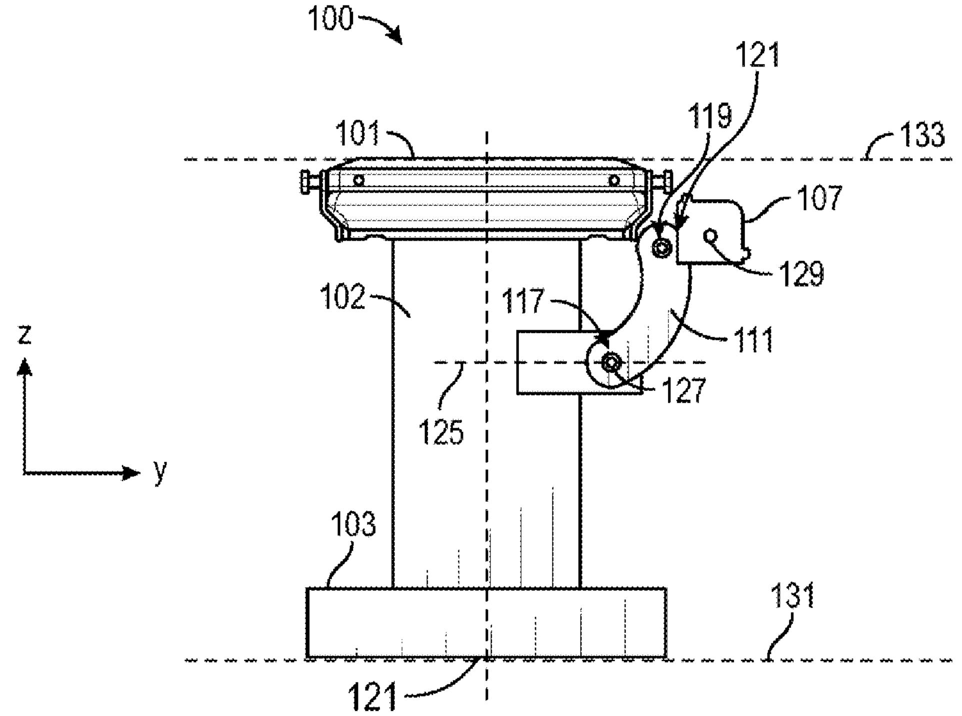
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
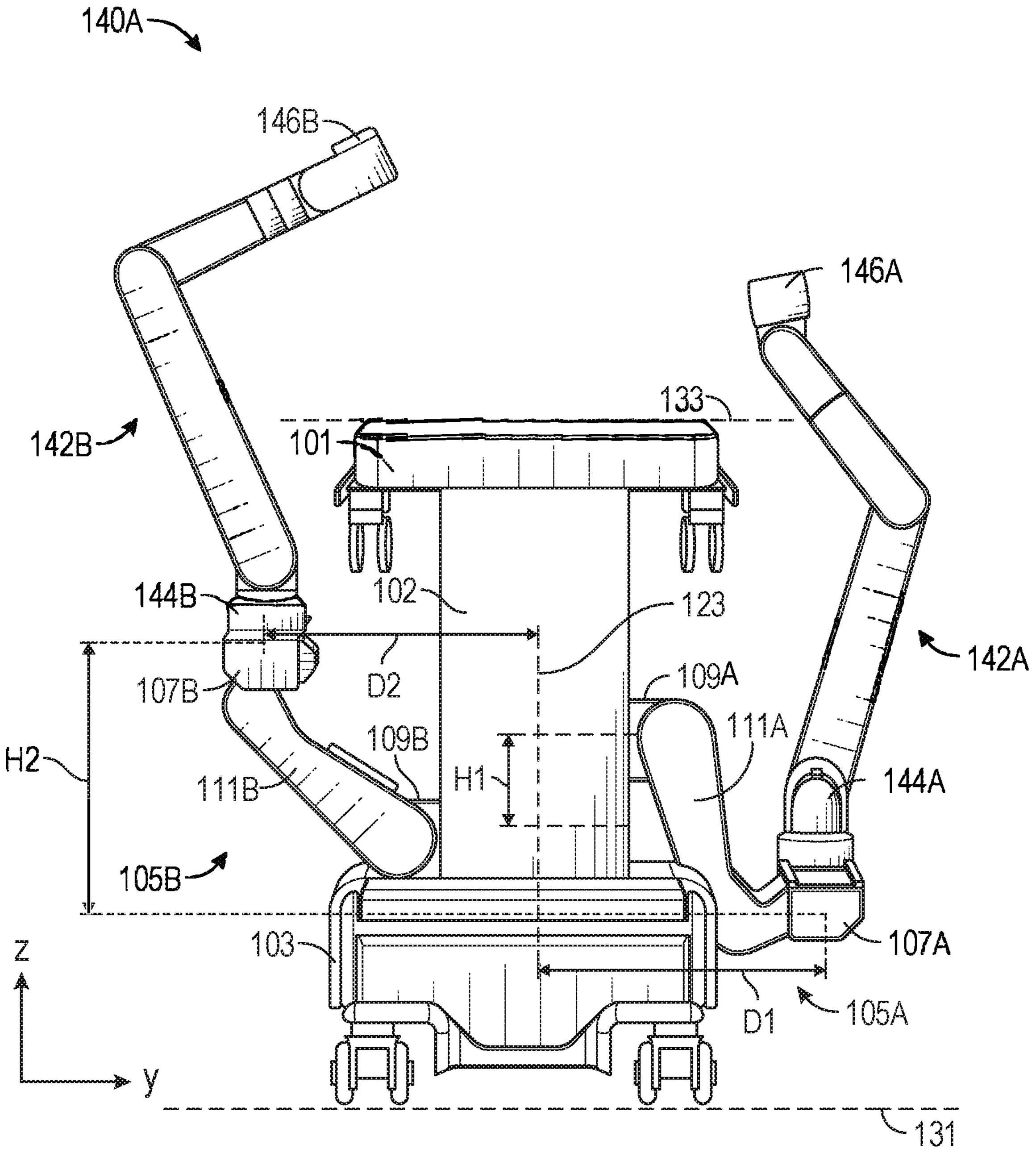
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
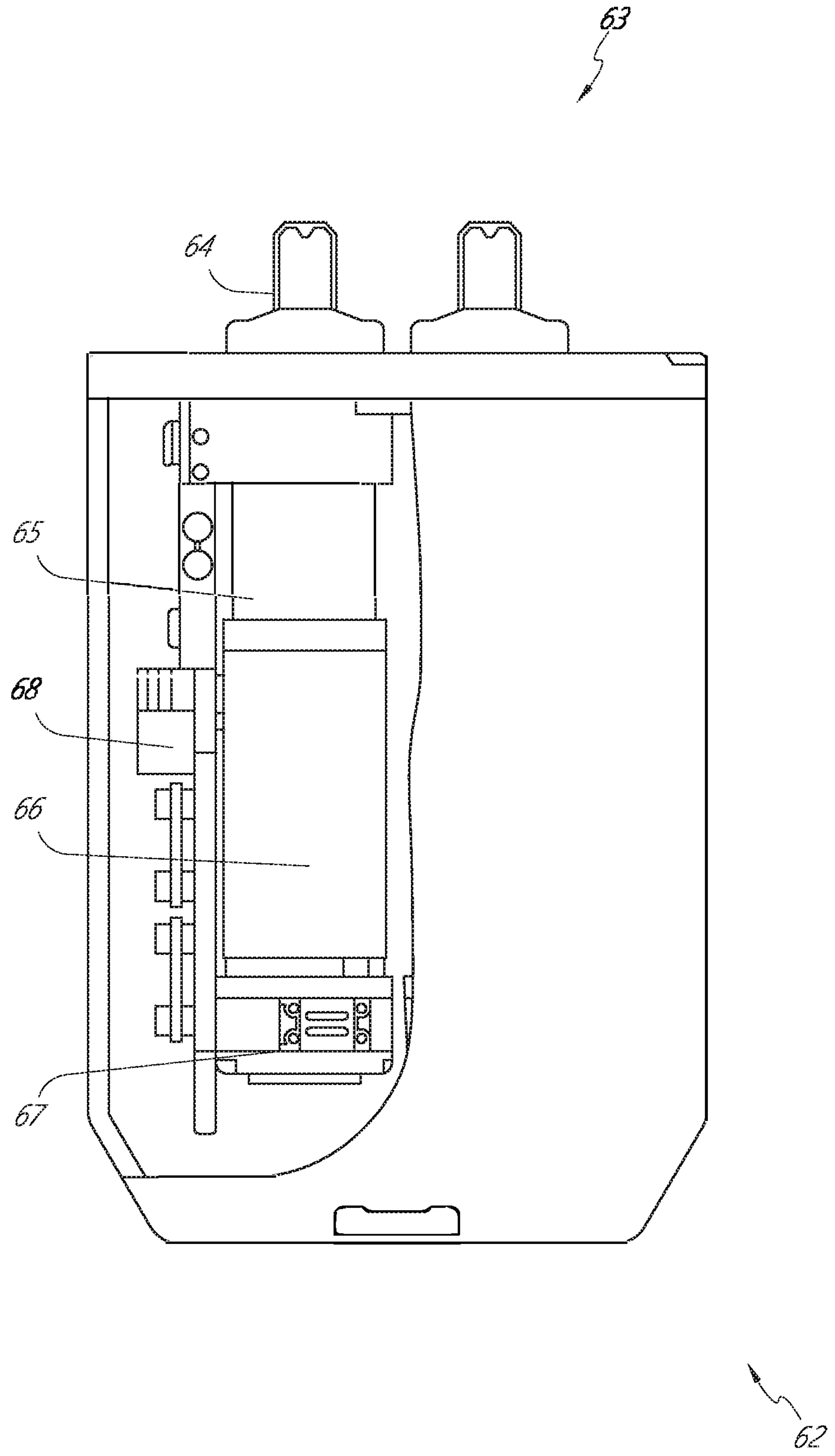
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
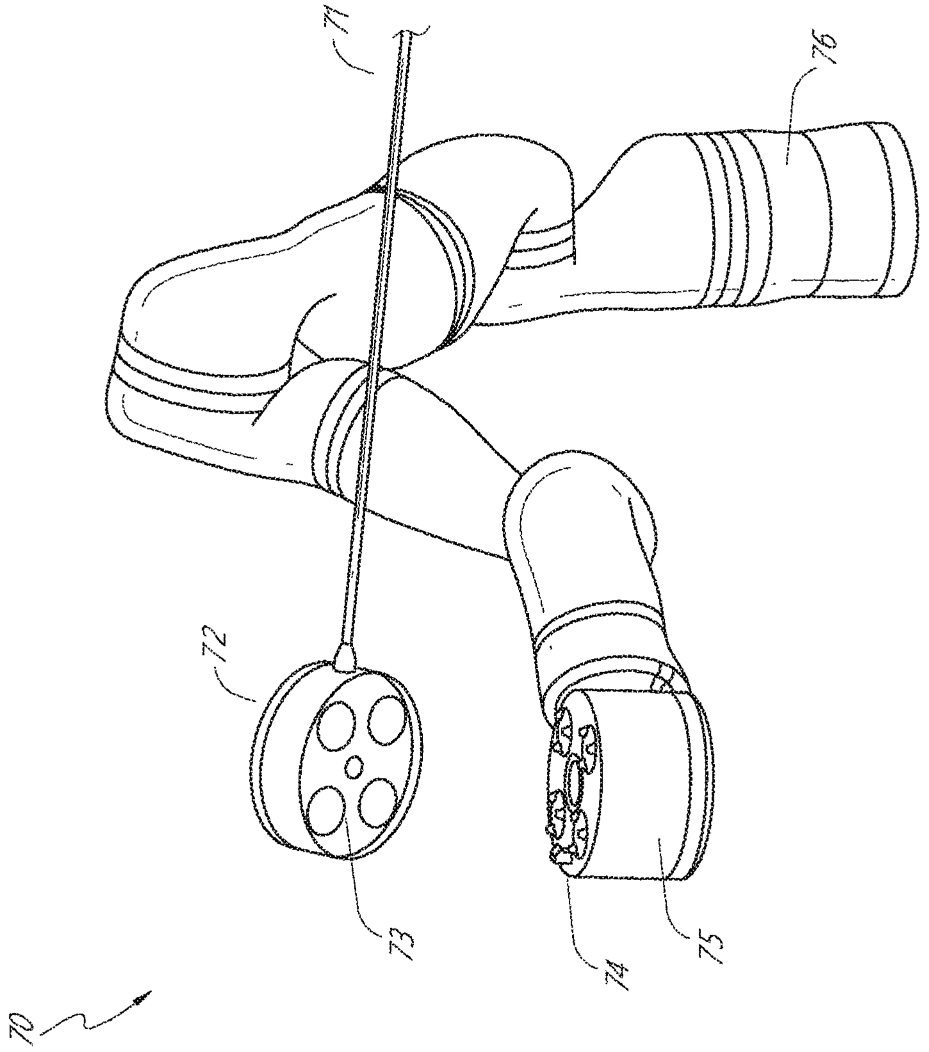
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft

71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
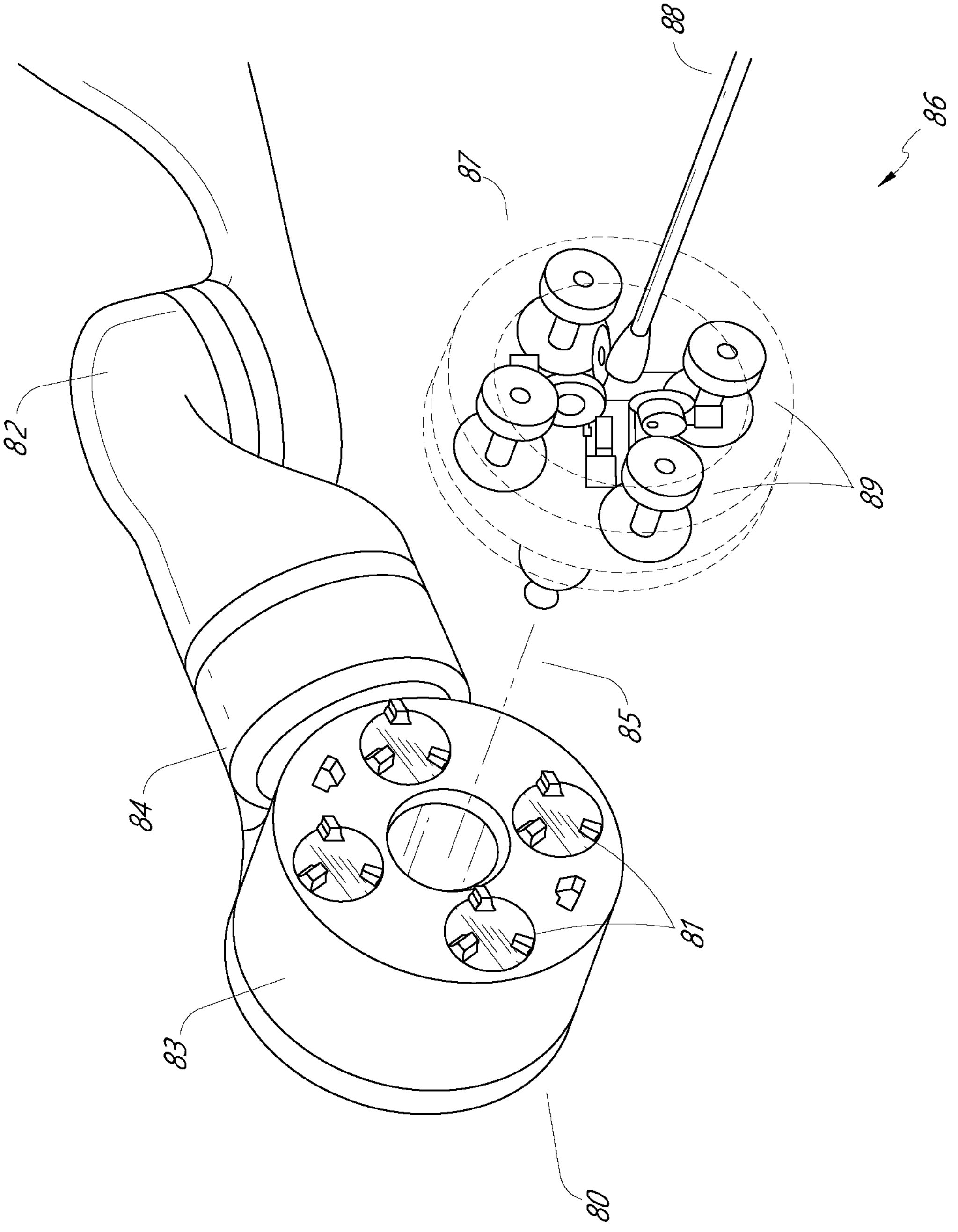
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
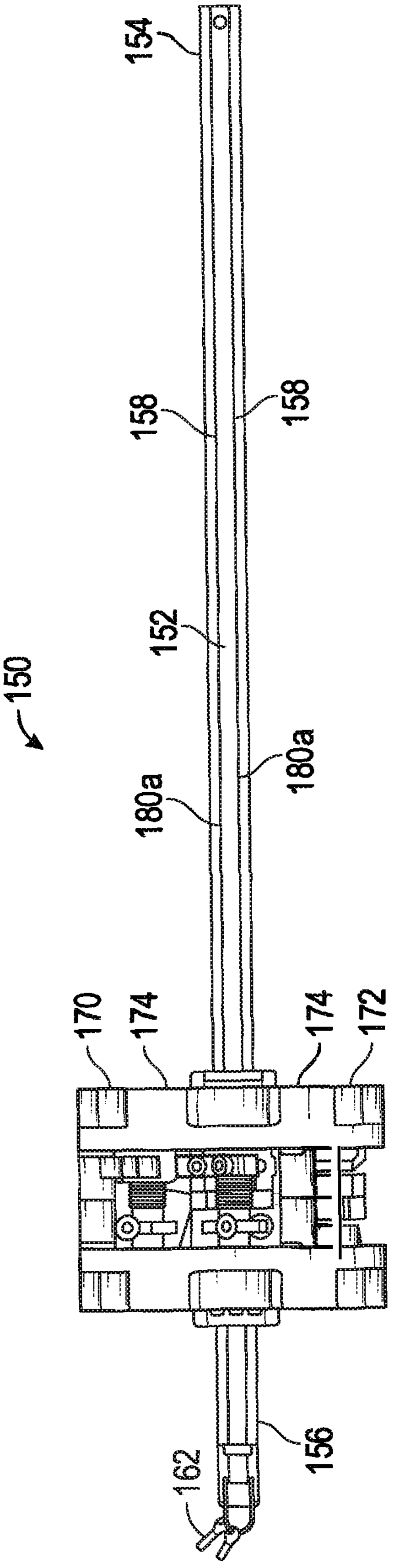
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
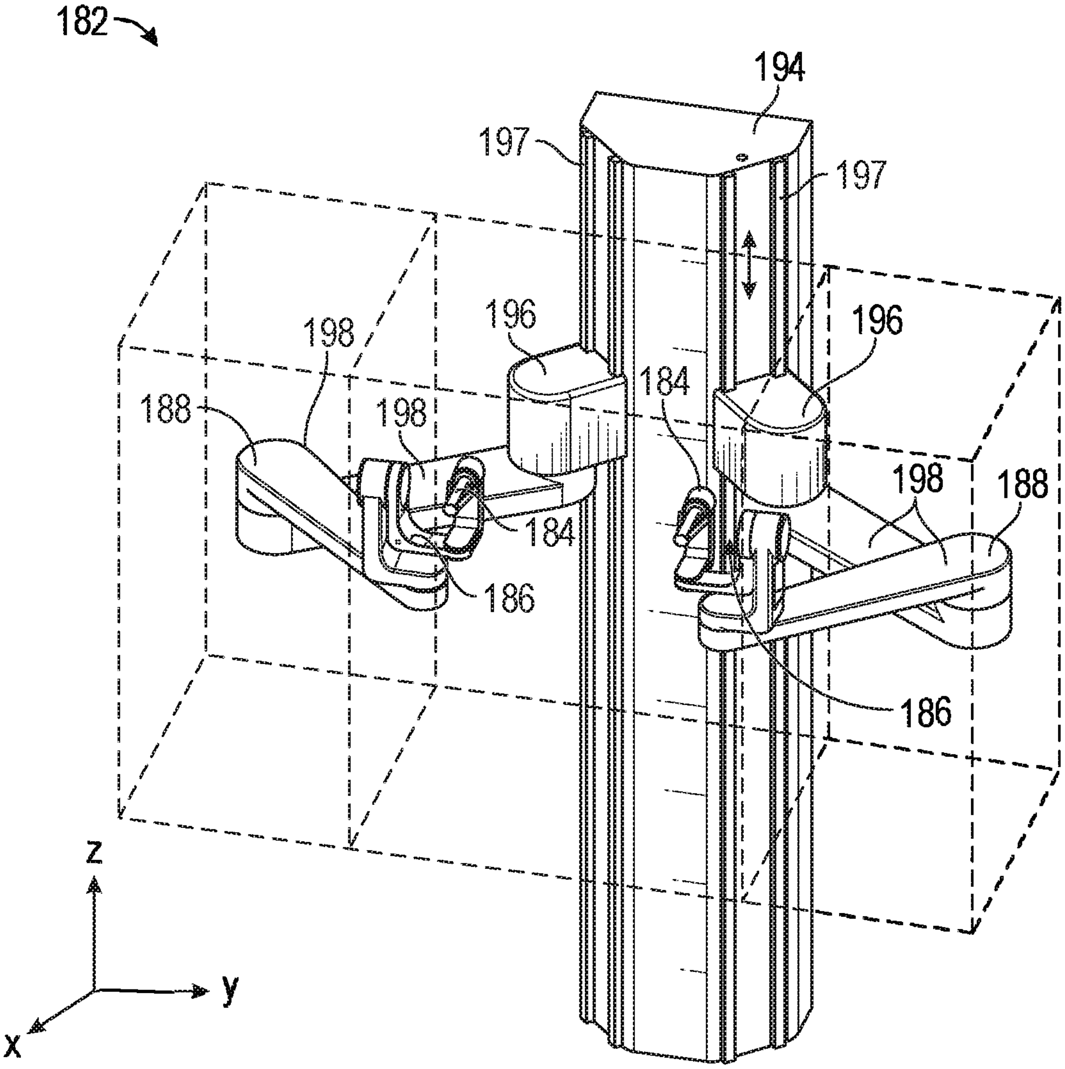
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
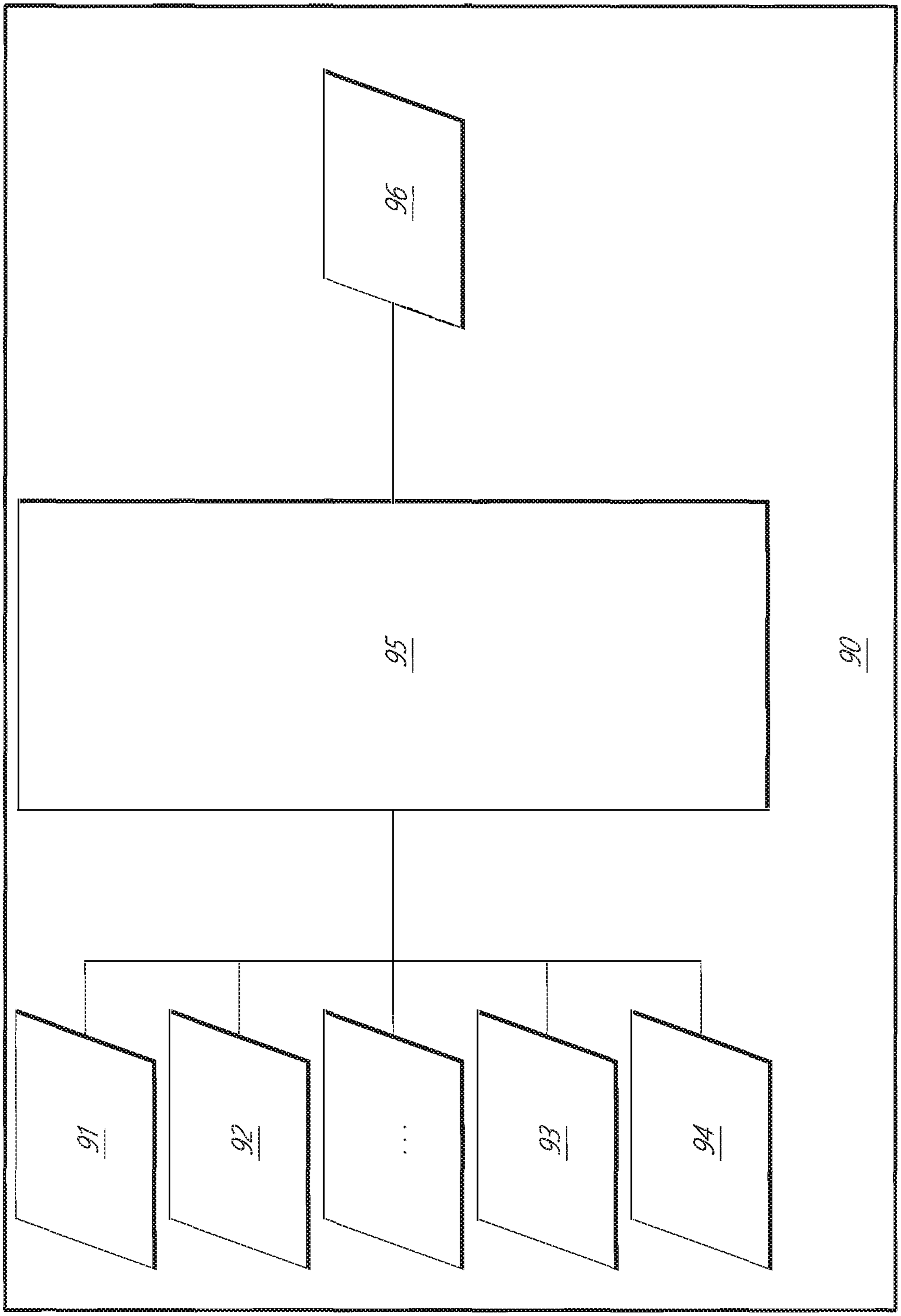
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Indicators for Robotic Medical Devices

Robotic medical systems, such as those described above with reference to FIGS. 1-20 and others, can include one or more indicators or indicator devices.

For example, a robotic medical system can include one or more indicators (such as visual, audible, or haptic indicators, among others) which can be configured to communicate or provide information about the system to a user or other medical personnel in an operating room.

Such indicators can be particularly useful for robotic medical systems that include a plurality of robotically controlled moveable components. In particular, the robotic medical systems can include medical instruments that change in temperature. The indicators can be configured to provide various functions as will be described below, including, for example, providing thermal information regarding the robotic system and/or components thereof. In some examples, other information may also be conveyed, such as information related to the identity or type of the medical instrument or related to a state of the medical instrument.

The indicators can be configured to provide or communicate thermal information about the system and/or its components. In some examples, the indicators can be configured to provide information related to a temperature state of the system or component(s) thereof. For example, an indicator can communicate that one or more components of the system is at an increased temperature. The indicator can serve to notify users in the vicinity of the system about the temperature of a component, so that the user knows to wait before moving the component or to wait before delivering additional energy to the component. This can advantageously prevent contact at unacceptable temperatures between the component and the patient, user, or other parts of the system. This can increase safety for those using these components delivering heat or energy. As will be described in more detail below, the indicators can advantageously be communicated in a number of ways and positioned in various components of the robotic system.

Figure 21A:
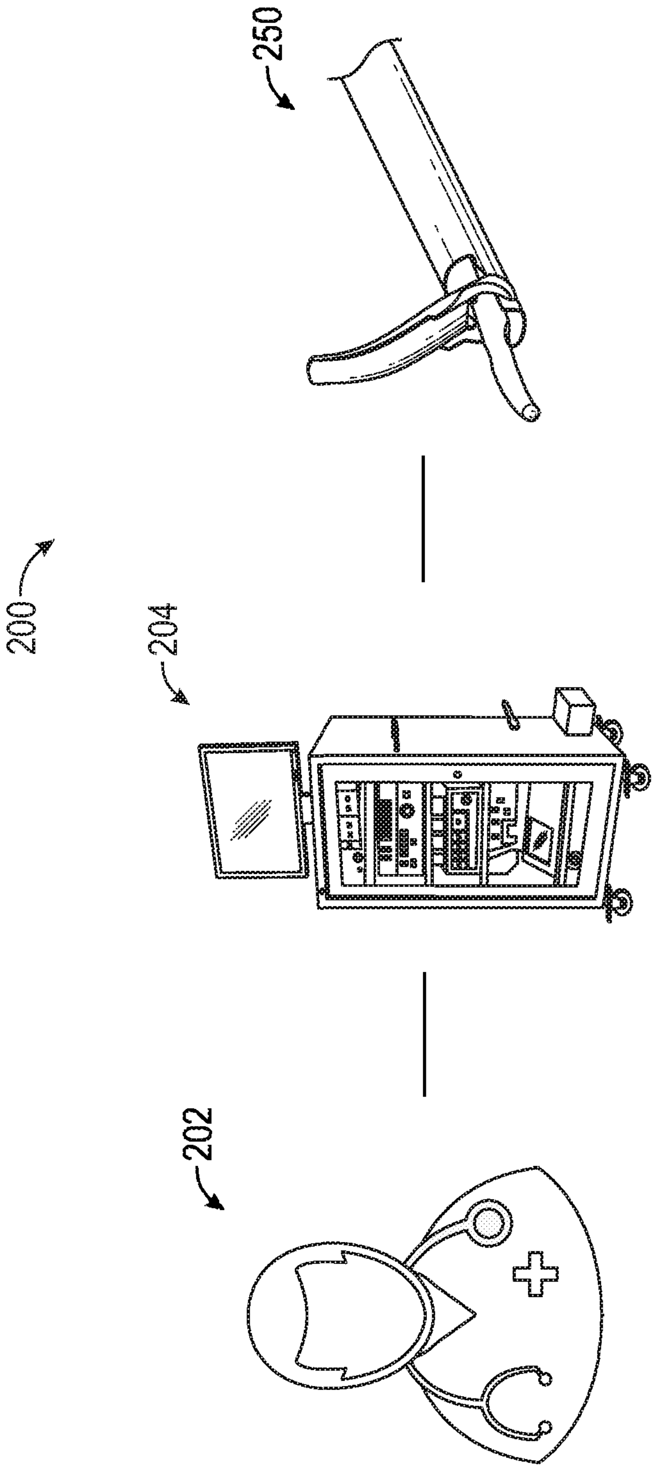
FIG. 21A illustrates a first example of a robotic system that includes one or more indicators.
Figure 21B:
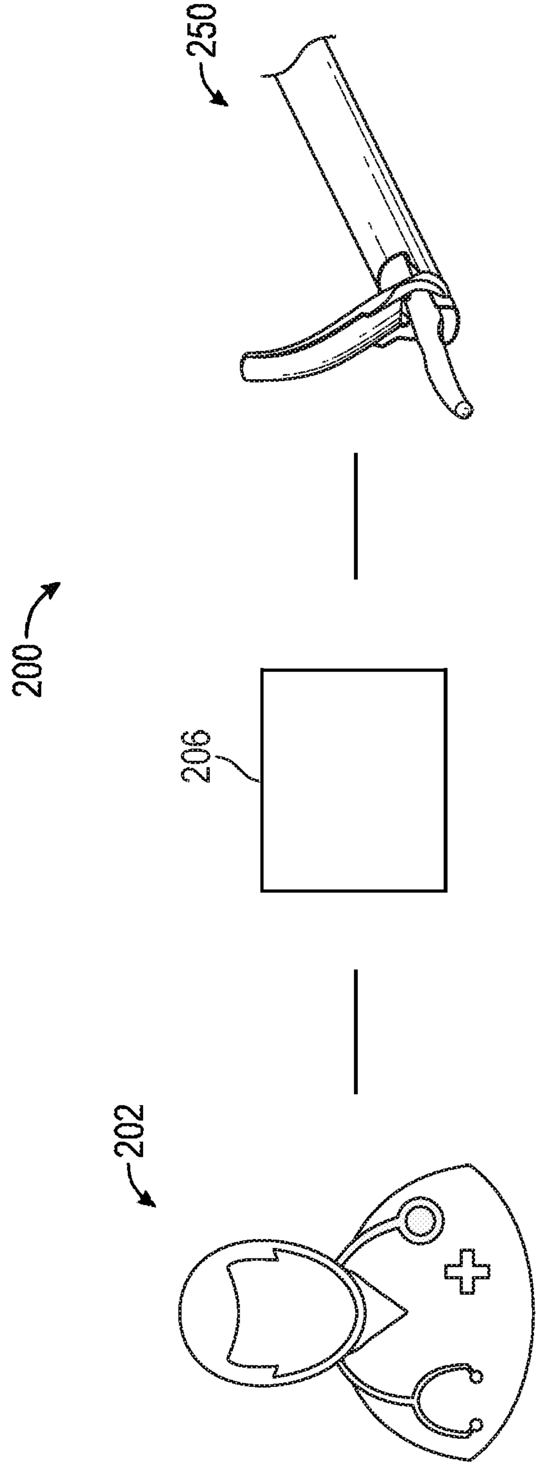
FIG. 21B illustrates a second example of a robotic system that includes one or more indicators.

FIGS. 21A and 21B illustrate examples of robotic systems 200 that may include one or more indicators. As shown in FIG. 21A, a user 202 may utilize or interact with the robotic system 200, which can include, among other things, a tower console 204 and a medical instrument 250 attached to and controlled by one or more robotic arms (not shown). As shown in FIG. 21B, the robotic system 200 can include a viewer 206 and a medical instrument 250 attached to and controlled by one or more robotic arms (not shown). In some embodiments, the viewer 206 can be part of a surgeon console. The medical instrument 250 can include a distal end configured to be inserted into a patient and apply heat to tissue within the patient. The medical instrument 250 can be controlled by a robotic manipulator (not shown) which is engaged with the medical instrument 250 and which can be configured to operate the medical instrument 250. The system 200 can be similar in some respects to the systems 10, 100, 140A described above. For example, with reference to FIGS. 1-4, the one or more robotic arms 12 of system 10 can engage with and control the medical instrument 250.

The robotic system 200 can include a temperature sensor configured to take one or more temperature readings of the medical instrument 250. The temperature sensor can be positioned in various places in the system 200. In some examples, the temperature sensor can be located within or near the medical instrument 250. In some examples, the temperature sensor can be configured to take a direct measurement of temperature of the distal end of the medical instrument 250. The distal end can include, for example, one or more of an end effector, jaws, a wrist, and/or a portion of a shaft of the medical instrument 250. In an example where the medical instrument 250 includes a wrist, the temperature measurement can be based on a direct measurement of the temperature of the wrist of the medical instrument 250. In some examples, the temperature measurement can be based on a direct measurement of the temperature of various parts of the medical instrument 230, such as the end effector, the jaws, and/or the shaft.

The temperature data from the temperature sensor can be received by one or more components of the robotic system 200, such as, for example, the tower console 204, the viewer 206 and/or other systems(s) in communication with the robotic system 200. For example, the tower console 204 or viewer 206 can include a screen or display configured to display one or more indicators. The one or more indicators can convey information related to a temperature of the medical instrument 250, based on the one or more temperature readings taken by the temperature sensor. The viewer 206 can be at various places within the robotic system 200. In some examples, the viewer 206 can be a screen or a display that is part of a physician/user console, a tower, a cart, and/or the medical instrument 250 itself.

As discussed below, the display can include a rendering of an image or representation (graphical or otherwise) of the medical instrument 250. The display can also include an image overlay over the image of the medical instrument 250. The display can also include an indicator in the form of an image overlay that conveys information based on the one or more temperature readings taken by the temperature sensor (s).

The medical instrument 250 may comprise a number of medical instruments. For example, the medical instrument 250 can be used for a variety of surgical tasks such as dissection, cutting, ligation, and/or sealing. The medical instrument 250 can perform these functions by applying thermal energy to tissue. The medical instrument 250 can includes jaws, which are heated by electrical current, and in turn deliver thermal energy to the tissue. More generally, in some embodiments, the medical instrument 250 is an energy-delivering instrument that delivers energy from an energy source to cause a thermal effect (e.g., in tissue). Examples of energy devices that act in this manner include monopolar electrocautery instruments and advanced energy instruments, such as vessel sealers. In some cases, such energy-delivering instruments are also called thermal instruments. A common issue with these types of medical instruments is that there is typically a cool-down period associated with each firing of the medical instrument, as the end effectors of the instrument need to fully disperse the generated heat before the next contact with tissue. This can limit the speed or frequency with which the medical instrument can be used, since the user may have to wait for the medical instrument to cool before attempting the next firing. This can also lead to serious consequences for the patient, including inadvertent injury to adjacent structures or vessel rupture if the medical instrument is moved incorrectly or inadvertently before the instrument is adequately cooled. The indicators described herein are advantageously provided to alert a surgeon of when a medical instrument 250 has been adequately cooled.

Figure 22:
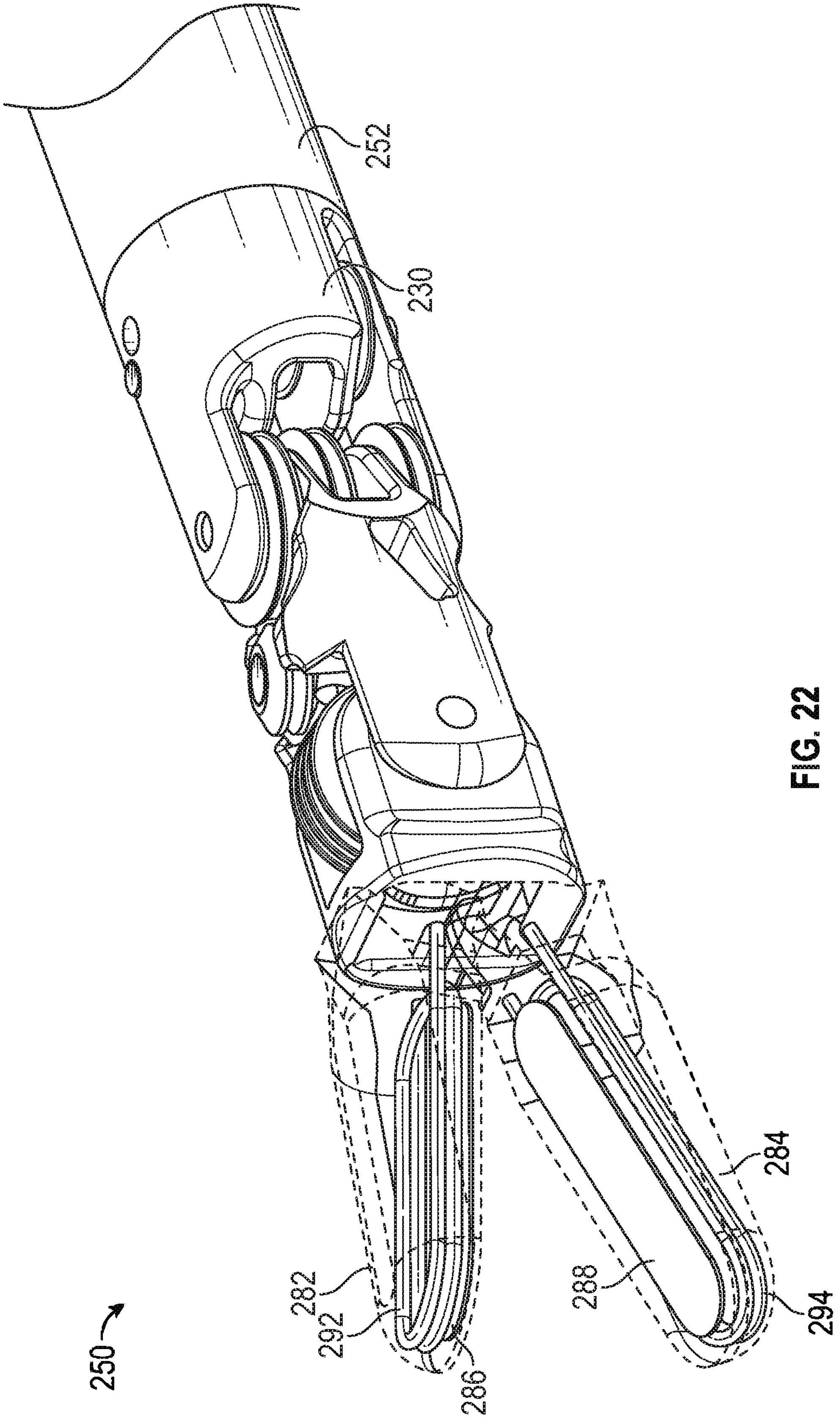
FIG. 22 illustrates a perspective view of a distal portion of a medical instrument configured to provide resistive heating.

FIG. 22 illustrates a top perspective view of a distal portion of one embodiment of a medical instrument 250 capable of resistive heating. The medical instrument 250 can include a multi-functional grasper and cutter including a shaft 252, a wrist 230, and an end effector including an upper jaw 282 and a lower jaw 284. At least one of the upper jaw 282 and lower jaw 284 includes a pad (e.g., upper pad 286, lower pad 288) formed in part of a ferrous material that allows resistive heat to be generated. In this example, the instrument 250 is capable of multiple functions, including sealing and cutting, simply by modifying the temperature of the upper and lower pads 286, 288, thereby advantageously reducing the need for a physical cutting blade. In an alternative example, a physical cutting blade (not shown) can also be provided with the upper and lower pads 286, 288 if desired. The elongated shaft 252 can be coupled to an instrument handle (not shown). The wrist 230 can move in multi-degrees of freedom. For example, in the present example, the wrist 230 is capable of moving in both the pitch and yaw dimensions of movement.

The end effector includes an upper jaw 282 and a lower jaw 284 configured to, among other things, grasp tissue. The upper jaw 282 has an upper pad 286 and a conductive line 292 adjacent to the upper pad 286. Likewise, the lower jaw 284 has a lower pad 288 and a conductive line 294 adjacent to the lower pad 288. In some examples, the upper pad 286 and lower pad 288 can be formed entirely of a ferrous material. In other examples, the upper pad 286 and the lower pad 288 can be formed of a non-ferrous material that is coated at least in part by a ferrous material. In some examples, the conductive lines 292, 294 can form a loop or coil that extends substantially around a perimeter of the upper and lower pads 286, 288. In other examples, the conductive lines 292, 294 are not in the form of a loop or coil, but is simply a straight, linear, wavy, or zig-zagged line that extends adjacent the pads 286, 288.

Current can be delivered through the conductive lines 292, 294 from a power source (not shown) to generate heat within the upper and lower pads 286, 288. Current is delivered through the conductive lines 292, 294, thereby generating heat in the upper and lower pads 286, 288 via magnetic induction. While the instrument described is heated at the end effector or jaws, medical instruments can be heated in multiple areas, including the multi degree of freedom wrist 230 or shaft 252. Advantageously, the heat can be monitored and modulated via a processor or controller, as described above, thereby allowing for different functions, such as cauterization, hemostasis or cutting. One skilled in the art will appreciate that the instrument embodiment in FIG. 22 is just one example of a type of instrument capable of generating heat via resistive heating, and that there are other ways for instruments to generate heat, such as by electrosurgery and laser technology. In some embodiments, heat can be generated on and around an instrument (e.g., around nearby tissue) via harmonic oscillations or vibrations. In some embodiments, a harmonic instrument can vibrate, thereby causing frictional heat to be generated between the instrument and adjacent tissue.

To avoid risk of injury to a patient, the medical instrument 250 after heating should be cooled prior to engaging tissue again or prior to firing the medical instrument 250 again. In some examples, the medical instrument 250 should be cooled to a temperature, such as approximately 75, 70, 65, 60, 55, 50, 45, 40, 35 or 30 degrees Celsius. In some examples, a certain temperature and/or time between firings can be set as threshold for subsequent activation of the medical instrument.

As previously described, the medical instrument 250 can include a temperature sensor. The temperature information can be captured by direct measurement of the temperature of the end effector of the medical instrument. The temperature can also be determined based on inputs, such as known characteristics of the medical instrument, including, e.g., firing time, thermal decay constant(s), external or intracorporeal body temperature, or combinations thereof. In some embodiments, a sensor (e.g., an infrared, CCD, CMOS, or the like) can be coupled to one of the tools (e.g., the laparoscope). In an embodiment in which the sensor (e.g., infrared sensor) is attached to a laparoscope, the laparoscope is capable of sensing temperature of a multiple of sites within the view of the camera.

The system can use indicators to inform a user, such as a clinician, when the medical instrument is or will be available for safe use. Note that while the indicator(s) can be used and illustrated with respect to the end effector of the medical instrument, the indicator(s) can also be used and illustrated with respect to the wrist, shaft, or anywhere else on the instrument that may be heated. The indicators can include be communicated in a variety of ways, such as visually, audibly, haptically, or any combination thereof. In some examples, the indicators can be communicated visually and positioned on a graphical user interface or on the instrument itself. Other locations for the indicators are also possible, such as on a patient table or bed, a cart, or one or more robotic arms.

The illustrated positions of the indicators are provided by way of example, not limitation. Further, not all indicators need be included in all embodiments. For example, in some embodiments, one or more of the indicators may be omitted from the viewer 300. Features and functionality of the visual indicators will be described in this section with reference to the example embodiments illustrated in FIGS. 23-27. The illustrated embodiments are provided by way of example and illustration and are not intended to be limiting. Upon consideration of this disclosure, one of skill in the art will appreciate that other configurations and embodiments, which are within the scope of this disclosure for systems with indicators are possible. Further, several notable advantages of indicators configured to display thermal information for use with robotic medical systems will be described below. Not all of the described advantages need be provided by every embodiment, and the indicators may also provide advantages that are not described herein.

Figure 23A:
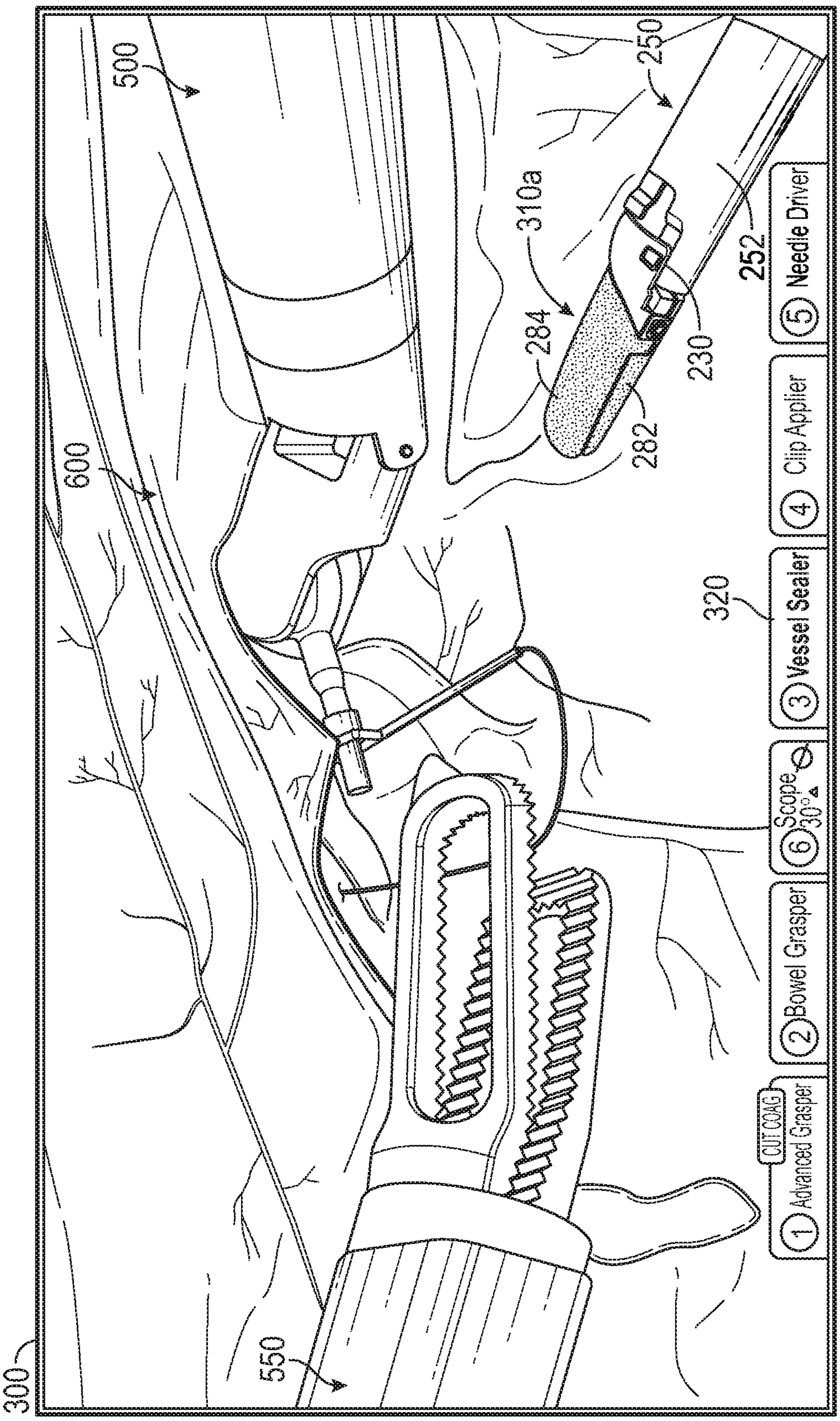
FIGS. 23A, 23B, 24A, and 24B illustrate examples of a viewer that includes one or more heat indicators over a representation of a distal portion of a medical instrument.
Figure 23B:
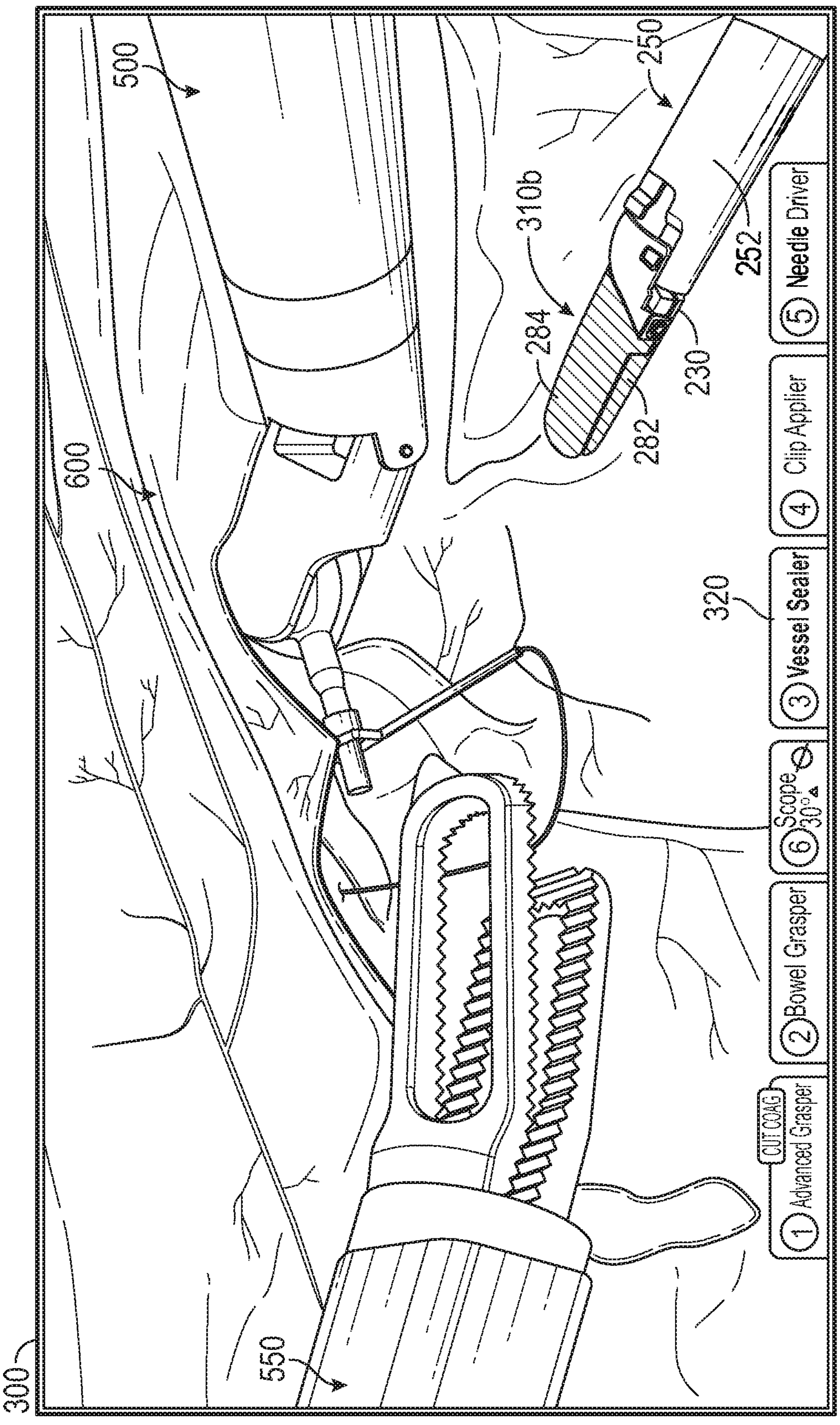

FIGS. 23A and 23B illustrate exemplary embodiments of a viewer 300 that may include one or more indicators. In the illustrated embodiment, as will be explained in further detail below, the viewer 300 can be configured to display, among other things, an image or representation of a medical instrument 250 with one or more indicators regarding a status of the medical instrument 250, such as, e.g., a heat or temperature level of a distal portion of the medical instrument 250. In the illustrated embodiment, the distal portion of the medical instrument 250 comprises a pair of jaws 282, 284 configured to deliver heat and/or clamp together. In the illustrated embodiment, the indicators comprise visual indicators and take the form of a color-coded overlay 310 on top of the jaws of the medical instrument 250.

The viewer 300 can be configured to allow the user to view images of a treatment site 600 from one or more imaging devices (e.g., cameras) of the robotic system in order to facilitate control of the system to perform a robotic medical procedure. For example, a robotically-controllable endoscope of the robotic system can include a camera positioned at a distal tip thereof. The user can view an image from the camera of the endoscope in the viewer 300 in order to facilitate control of the endoscope and/or other components of the robotic medical system. As another example, the robotic system may include one or more cameras laparoscopically or endoscopically inserted into a patient. The user can view images from the inserted cameras in order to facilitate control of one or more additional robotically-controlled medical instruments, such as one or more additional laparoscopically inserted medical instruments, such as the medical instruments 250, 500, and 550 as shown. The viewer 300 can comprise a screen for viewing the images from the one or more cameras. In some embodiments, the viewer 300 includes a stereographic or stereoscopic viewer.

With continued reference to FIGS. 23A and 23B, illustrated is an embodiment of a viewer 300 configured to display/render an image or representation of at least a portion of a medical instrument 250 alongside other tools or instruments 500, 550 at a treatment site 600. The viewer 300 can also display, for example, an indicator in the form of an image overlay 310 displayed over the image of the medical instrument 250. Although the illustrated examples of FIGS. 23A and 23B show an image overlay 310 displayed over the representations of the jaws 282, 284 of the medical instrument 250, the image overlay 310 can be displayed over other portions of the representation of the medical instrument 250, such as anywhere on the distal end of the medical instrument 250. In addition to or alternatively, the image overlay 310 may be displayed over other parts of the representation of the medical instrument 250, such as the representation of the wrist 230 or the representation of the shaft 252.

In FIGS. 23A and 23B, the image overlay 310 is shown as a region of shading over the representations of the end effector 282, 284, which can correspond to different colors or patterns, such as flashing, to a user of the display 300. This can be advantageous as the image overlay 310 is displayed over the representation of the portion of the medical instrument 250 of interest, as the jaws 282, 284 of the medical instrument 250 are the portion of the medical instrument 250 that applies heat. This allows the information conveyed by the image overlay 310 to be displayed directly on the image or representation of the medical instrument for which it is related.

FIG. 23A shows a first indicator 310*a* of a first color or pattern and FIG. 23B shows a second indicator 310*b* of a second color or pattern. In some examples, the different colors or patterns of indicators 310 correspond to different temperatures of the medical instrument 250. For example, an indicator 310 of a first color (e.g., green) can indicate the temperature is cool or below a certain temperature threshold, while an indicator 310 of a second color (e.g., red) different from the first color can indicate the temperature is hot or above a certain temperature threshold. In some examples, a pattern of flashing, such as variations in frequency, can indicate a temperature of the medical instrument 230. In some examples, the opacity of the indicator 310 can indicate a temperature of the medical instrument 250. For example, a more opaque color of the indicator 310 can indicate the temperature is high, while a lower opacity of the color of the indicator 310 can indicate the temperature is low. The temperature may be considered high when it is above a certain threshold. The temperature may be considered low when it is below a certain threshold. The threshold can be based on a user input, a user preference, the patient, the type of procedure, the type of instrument, the type of functionality being performed by the medical instrument, or any other number of factors.

As noted above, the system can include one or more controllers configured to be operated by the user in order to provide control of various aspects or components of the robotic medical system. The one or more controllers can include gimbals or pedals. Examples of such controllers 182 have been described above with reference to FIG. 19. In related aspects, one or more of the controllers can be configured to selectively couple and control medical instruments. The one or more controllers can be configured to allow a user to fire or activate a thermal/heat (e.g., cauterizing, sealing, etc.) feature of a medical instrument. The controllers can be configured to perform or activate different functions of the instruments (e.g., cut, grasp, coagulate, seal, etc.). Additional features and functionality of the controllers 182 have been described above with reference to FIG. 19, which illustrates one embodiment thereof. Other embodiments of handheld controllers are also possible, including controllers that include keyboards, touchpads, buttons, joysticks, mice, etc.

As described above, the system 200 may be configured to control more than one medical instruments as well as more than one modalities of each of the medical instruments. For example, as shown in FIGS. 23A-23B, there may be a first medical instrument 250, a second medical instrument 500, and a third medical instrument 550 at a treatment site 600. FIGS. 23A-23B also show a menu or series of tabs, each associated with the different medical instruments or with the various modalities of the medical instruments. Each medical instrument or particular modality of the medical instrument can have a tab or an associated image overlay that indicates the state, type, or identity of the medical instrument (e.g. "Vessel Sealer"). For example, a series of tabs are shown in FIGS. 23A-23B, including the "Vessel Sealer" tab 320 which is associated with the medical instrument 250.

In some examples, the menu or series of tabs may be image overlays positioned on an image or representation of a treatment site 600 within a patient of the viewer 300. The associated image overlay or tab of a certain medical instrument can be bolded, highlighted, enlarged, or otherwise differentiated when a user input (e.g. controller 182) is selectively coupled to the associated medical instrument. For example, the "Vessel Sealer" tab 320 can be bolded when the medical instrument 250 is selectively coupled to a user input. In some examples, the tab associated with the vessel sealer may be highlighted, bolded, enlarged, or otherwise differentiated to indicate the vessel sealer instrument is active, actuated, in motion, or heated. In some examples, each of the series of tabs may be selectable or clickable, where selecting or clicking a particular tab, the associated medical device can be selectively coupled to a user input. The menu or series of tab can be positioned anywhere on the viewer 300. As shown in the illustrated example in FIGS. 23A-23B, the menu or series of tab can be positioned on the bottom side of the viewer 300.

Figure 24A:
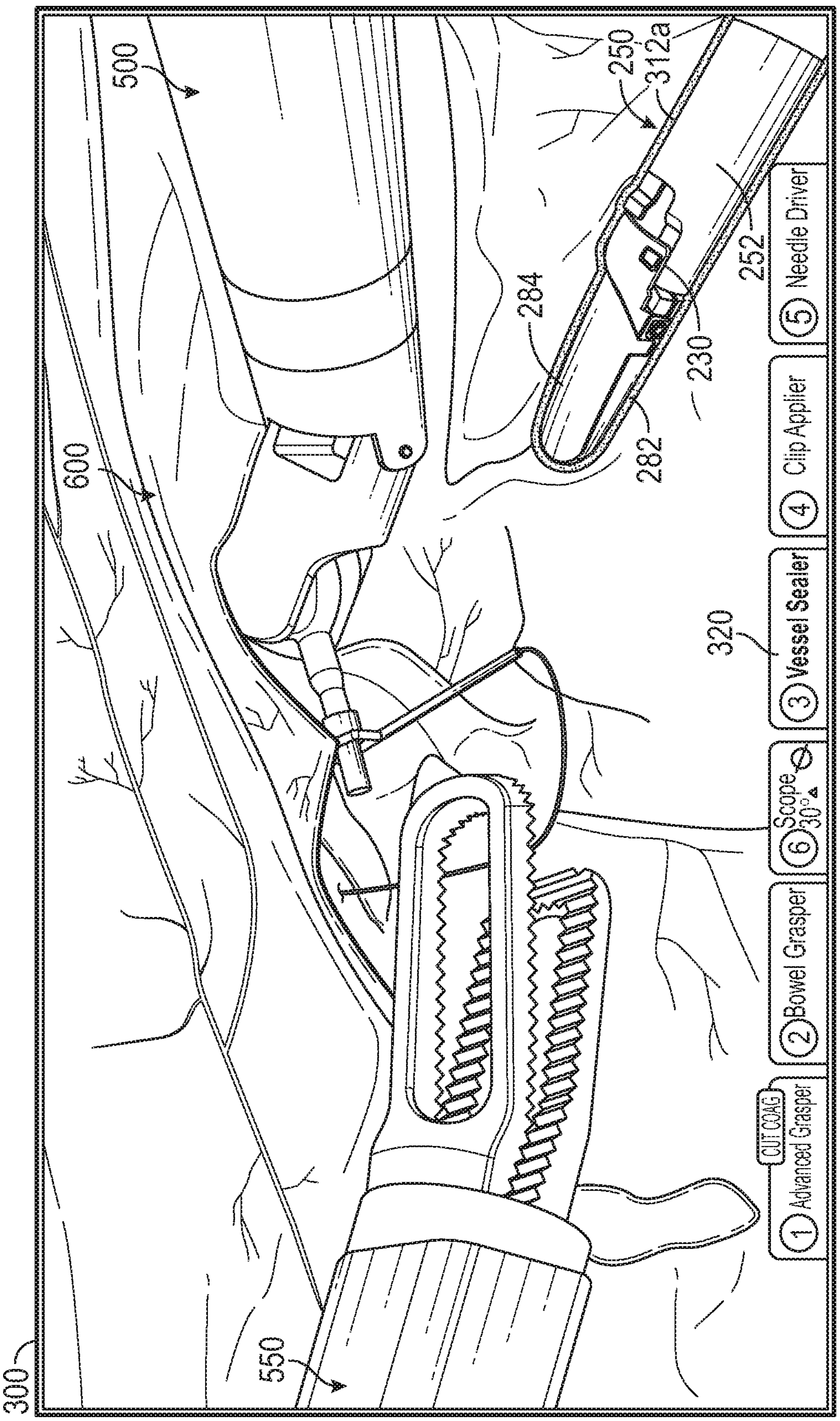
Figure 24B:
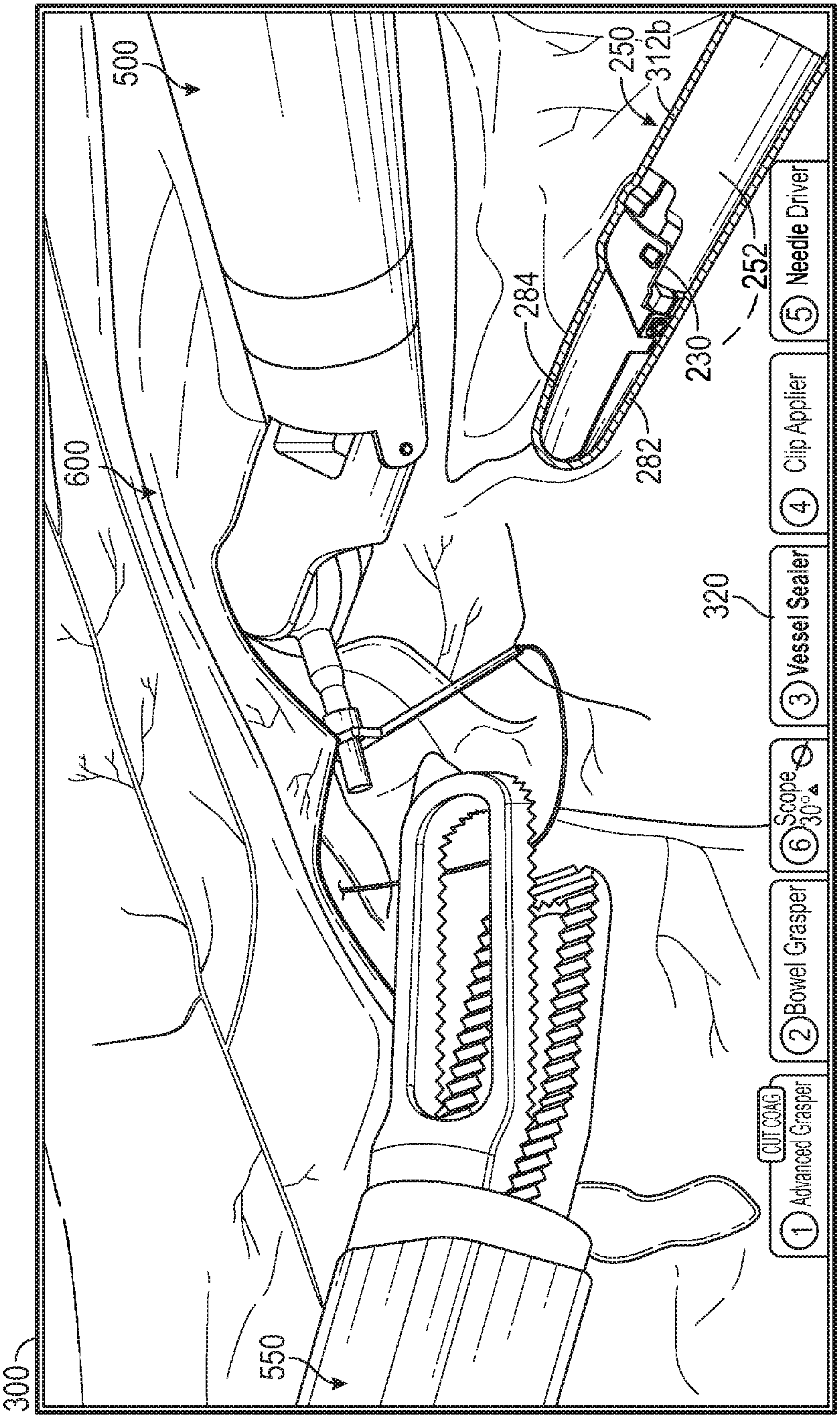

In FIGS. 24A-24B, the viewer 300 is shown including an image of a medical instrument 250. The image overlay 310 may be a region or an outline of shading around a portion of the representation of the medical instrument 250. Similar to FIGS. 23A-23B, the image overlay 310 may have different shading or patterns (such as described above) to indicate different temperatures of the medical instrument 250. As shown in FIG. 24A, a first image overlay 310*a* is positioned around the representation of the jaws 282, 284, the wrist 230, and the shaft 252 to indicate a first temperature. Similarly, in FIG. 24B, a second image overlay 310*b* of a different color or pattern is positioned around the representation of the jaws 282, 284, the wrist 230, and the shaft 252 to indicate a second temperature, different from the first temperature.

Figure 25A:
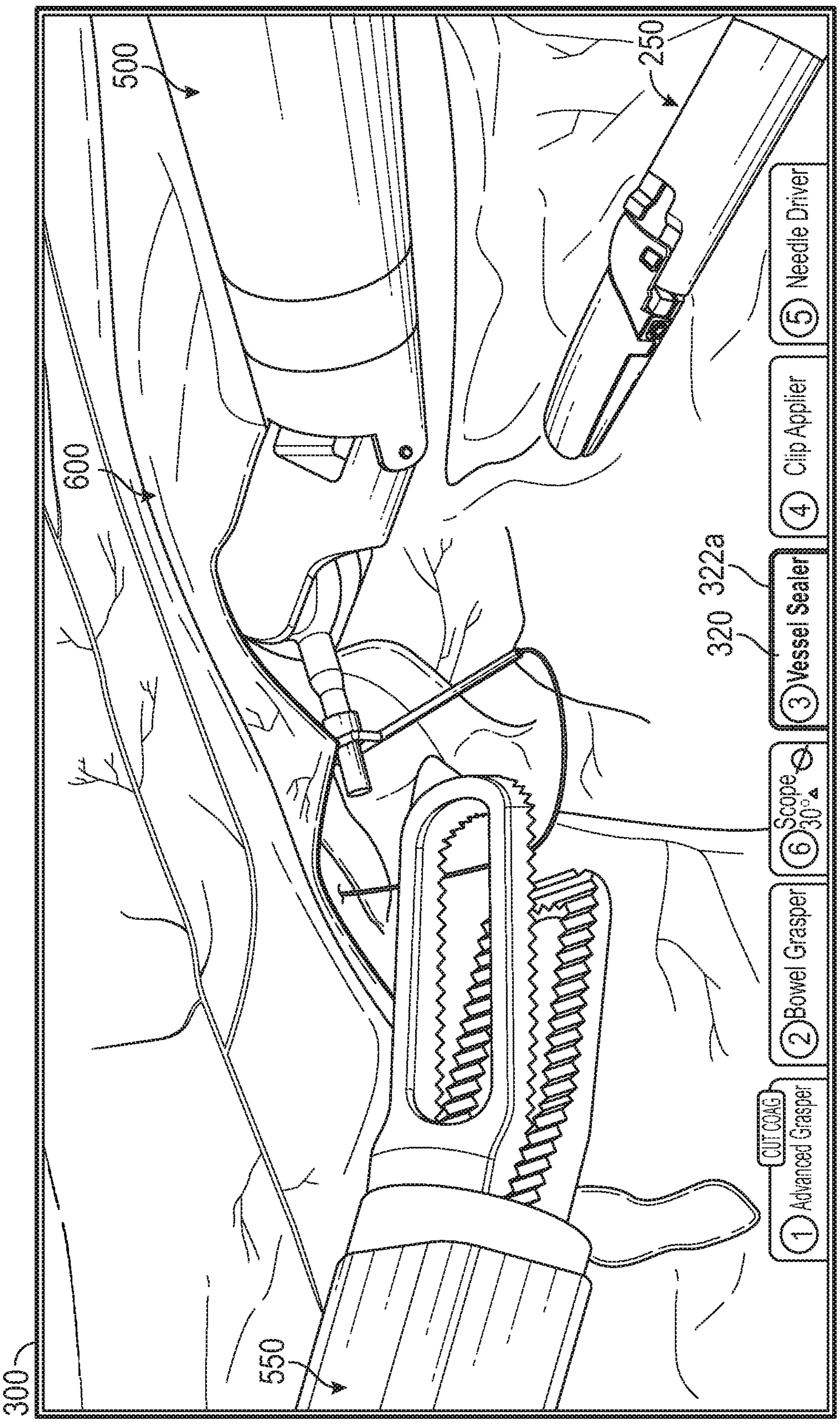
FIGS. 25A, 25B, 26A, and 26B illustrate examples of a viewer that includes one or more indicators regarding heat for a medical instrument.
Figure 25B:
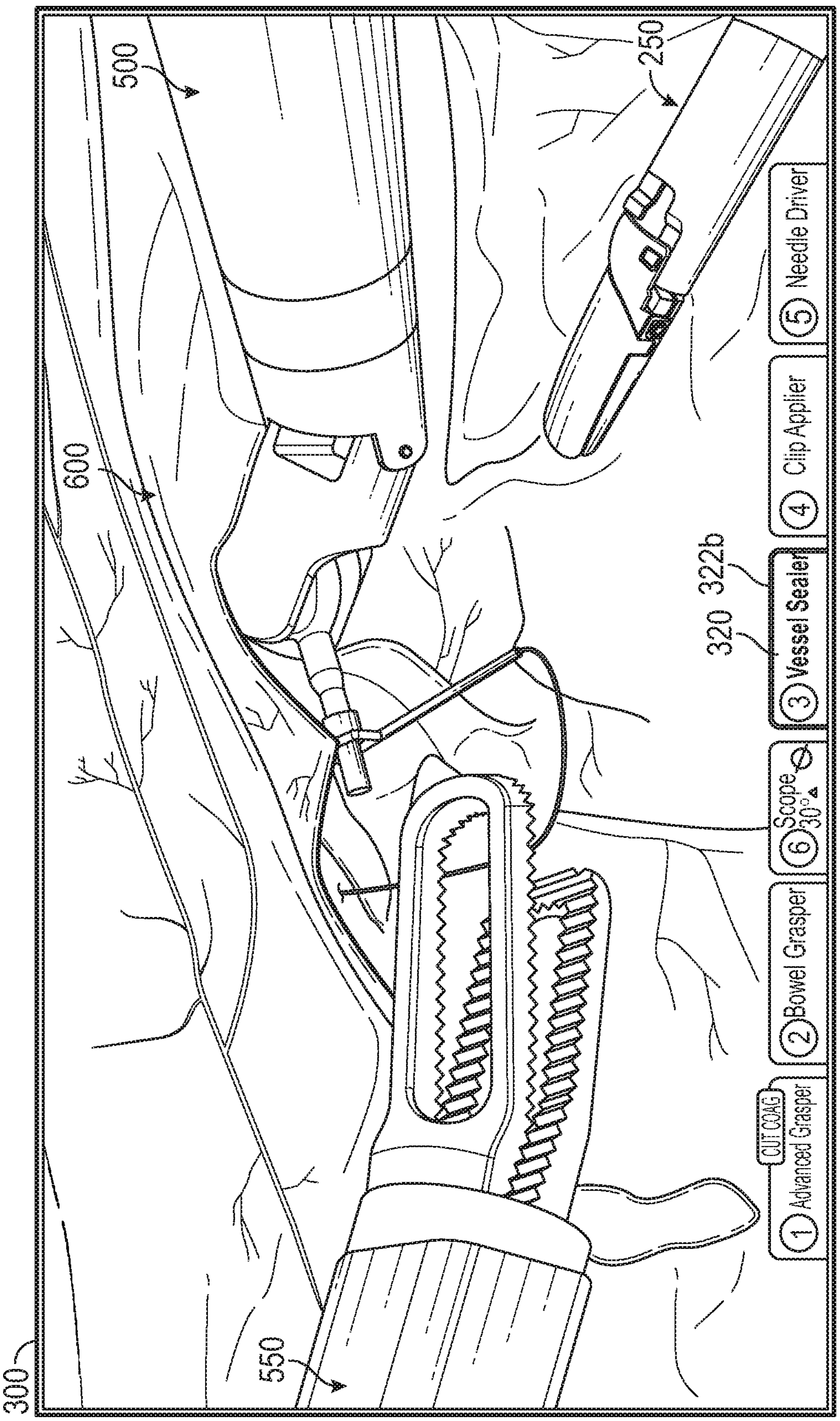

In FIGS. 25A-25B, the viewer 300 is shown including an image or representation of the medical instrument 250. The image overlay 322 may be a region or outline of shading around a second image overlay 320 associated with the medical instrument 250. In some examples, the image overlay 322 can be positioned over the second image overlay 320 associated with the medical instrument 250. The image overlay 322 can be positioned around or over the associated image overlay 320 to indicate a temperature of the associated medical instrument. As shown in FIG. 25A, a first image overlay 322*a* is positioned partially around a perimeter of the associated image overlay 320 to indicate a first temperature. Similarly, in FIG. 25B, a second image overlay 322*b* of a different color or pattern is positioned around a perimeter of the associated image overlay 320 to indicate a second temperature, different from the first temperature. This position of the image overlay 322 can be advantageous as the second overlay 320 can remain in a constant position on the viewer 300, regardless of the position of the medical instrument 250. This can allow an observer to quickly determine the temperature of the device without first locating where the device is positioned on the viewer 300. This allows the information conveyed by the image overlay 322 to be communicated on other indicators associated with the medical instrument 250.

Figure 26A:
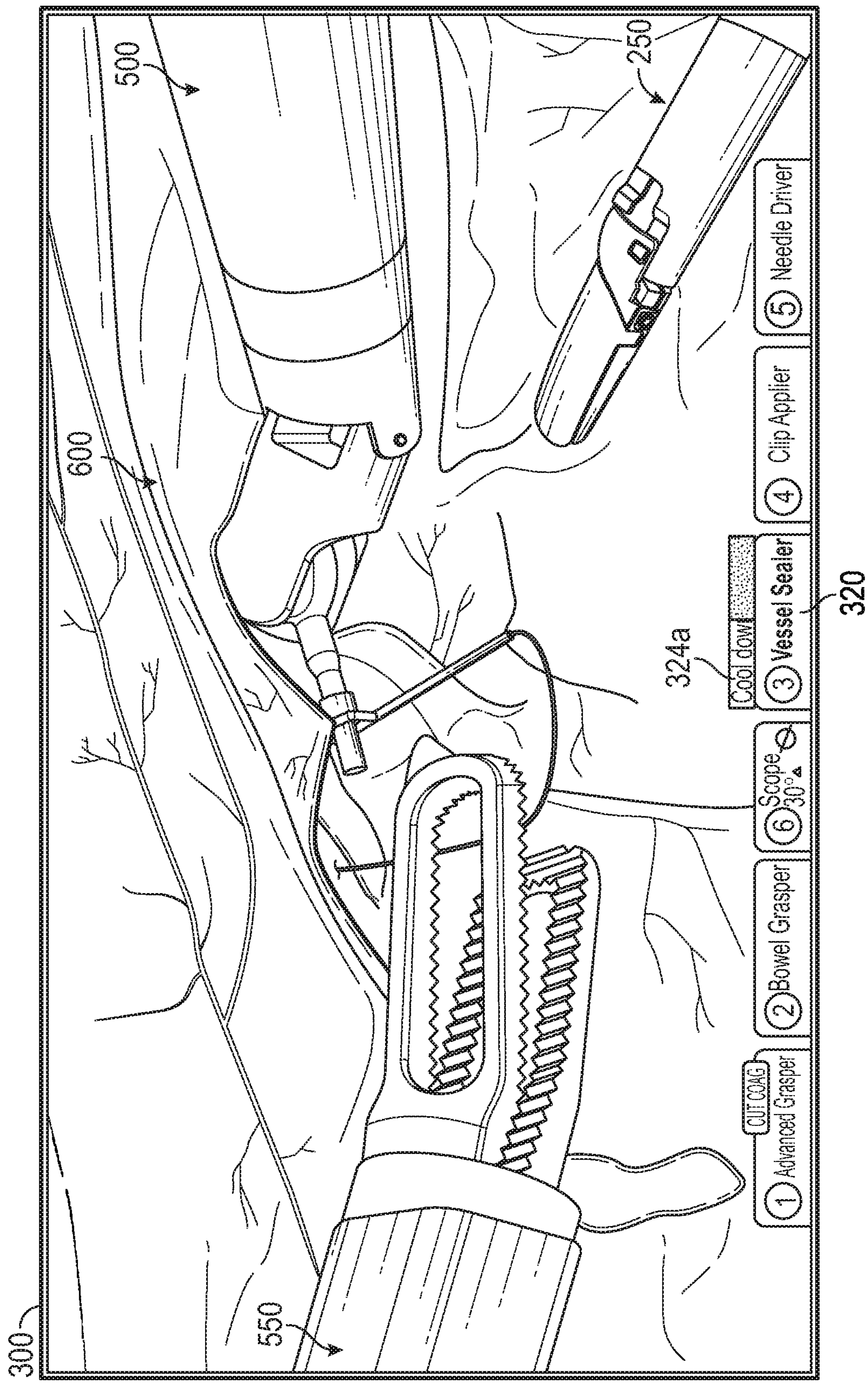
Figure 26B:
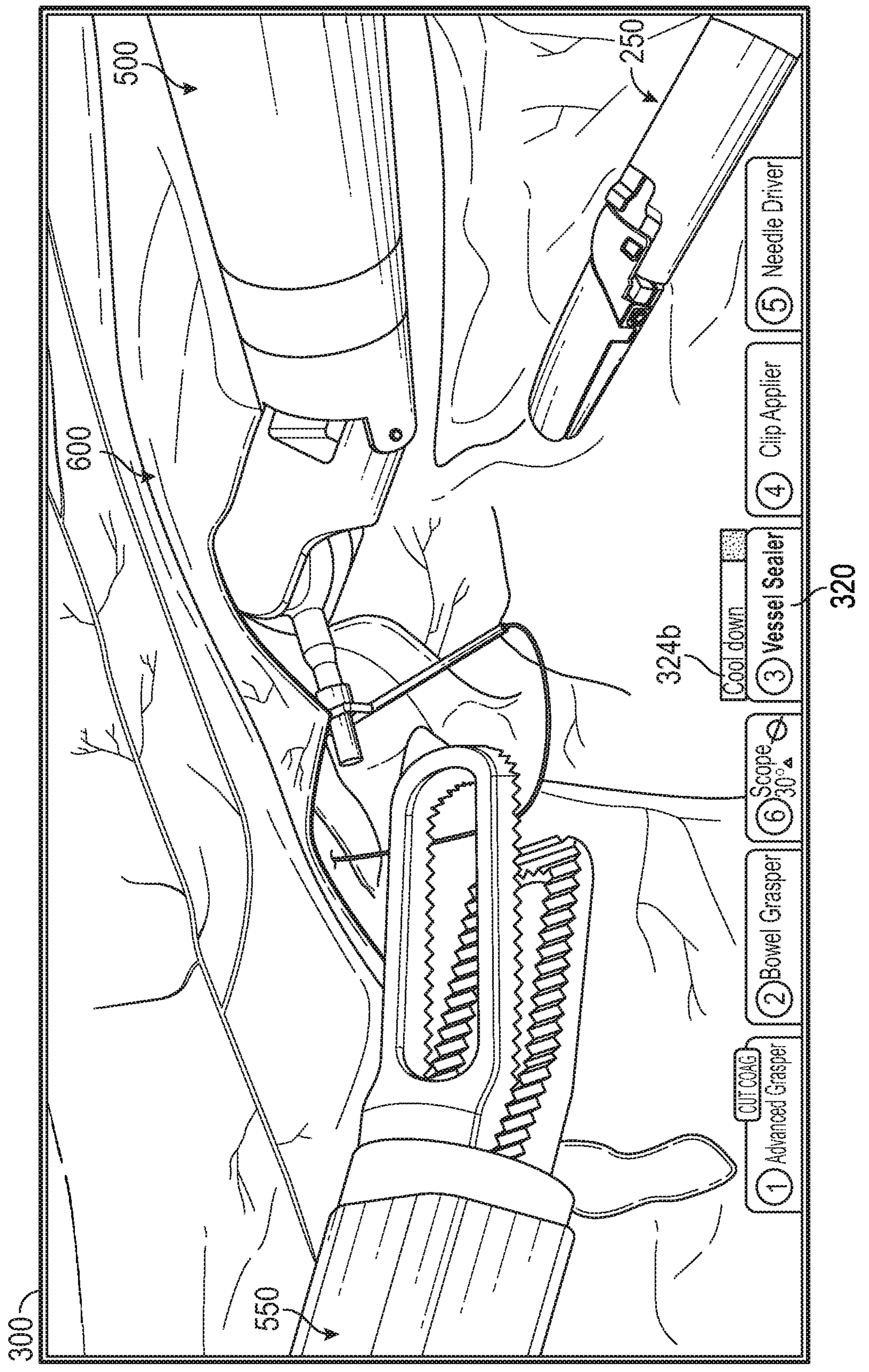

As shown in FIGS. 26A-26B, a combination of text and colors or shading can be used to indicate the temperature of the medical instrument 250. In FIG. 26A, the image overlay 322 is positioned on top of the second image overlay 320. The image overlay 324*a* can be shown as a progress bar, where shading of the progress bar indicates how much of the cool down period remains or how high the temperature is of the medical instrument 250. In FIG. 26B, the image overlay 324*b* is shown with less shading in the progress bar, indicating the cool down period is nearly complete and the temperature is almost cooled down.

Figure 27A:
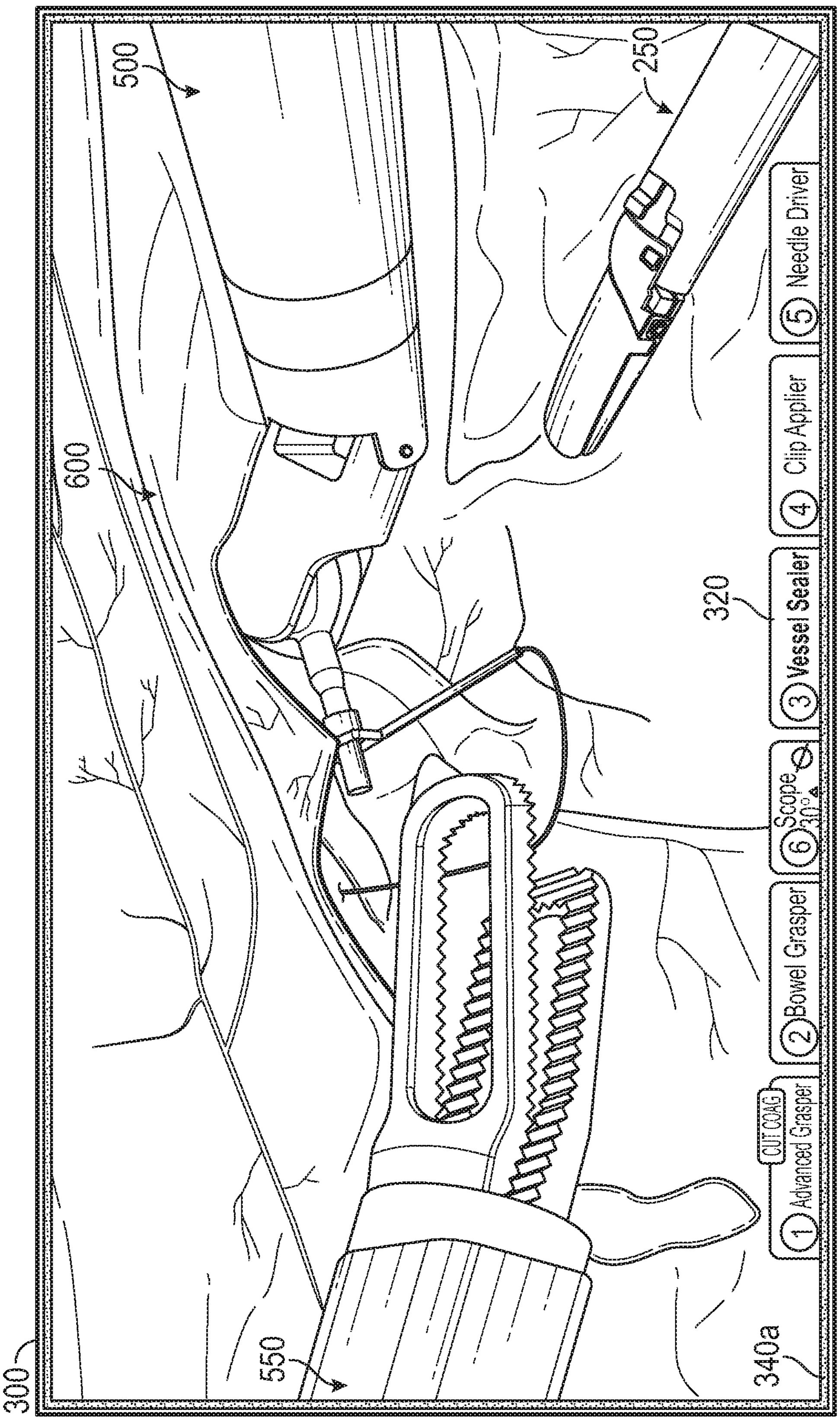
FIGS. 27A and 27B illustrate examples of a viewer that includes one or more heat indicators around a perimeter of the viewer.
Figure 27B:
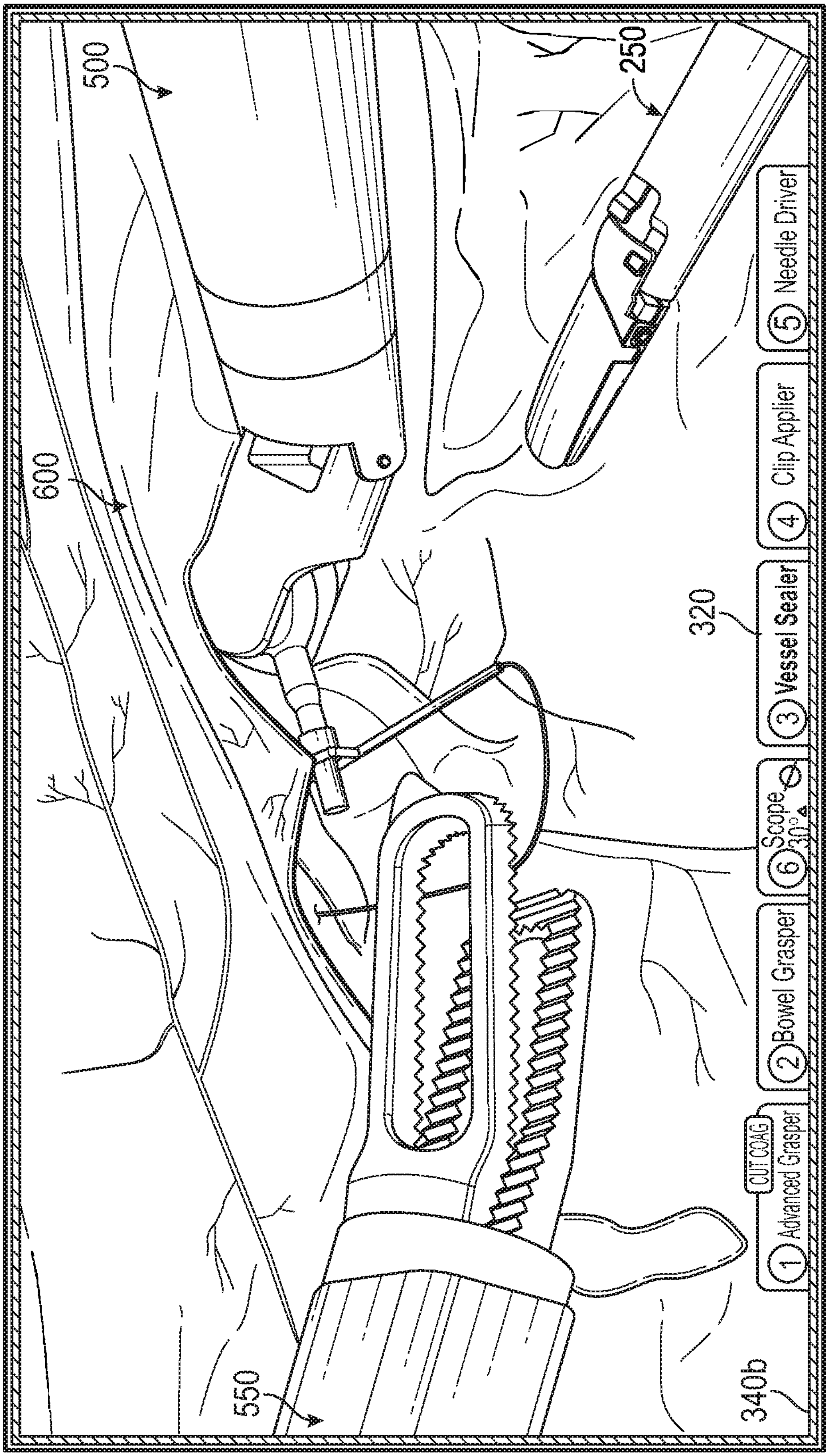

In some examples, the indicators can be displayed or communicated unassociated with the medical instrument. In FIGS. 27A-27B, the viewer 300 is shown including an image 350 of the medical instrument 250. The image overlay 340 may be a region of shading around the perimeter of the viewer 300. In some examples, the image overlay 340 may be a region of shading of a partial perimeter (e.g. a single side, the top and bottom, the sides) of the viewer 300. In some examples, such as shown in FIGS. 27A-27B, the image overlay 340 may be a region of shading around the entire perimeter of the viewer 300. This type of overlay may be advantageous as its increased size may increase the visibility of the image overlay 340 to a user observing the screen. This may allow an observer to determine the temperature of the medical instrument 250, even when looking other parts of the viewer 300, such as at other medical devices. In FIG. 27A, the first image overlay 340*a* is positioned around the entire perimeter of the viewer 300 to indicate a first temperature of the medical instrument. In FIG. 27B, the second image overlay 340*b* is positioned around the entire perimeter of the viewer 300 to indicate a second temperature of a medical instrument.

Furthermore, although only one indicator is shown in each of the illustrated embodiments below, other numbers of indicators are also possible. For example, the indicator 310 shown in FIGS. 23A-23B, the indicator 322 shown in FIGS. 25A-25B, or the indicator 340 shown in FIGS. 27A-27B can be shown simultaneously.

Furthermore, although visual indicators are displayed in these figures, other types of indicators can be used in combination with or in lieu of the visual indicators. For example, audio indicators can include various tones or volumes to indicate the temperature of the medical instrument. The audio indicators can be positioned in various positions in the system, such as at a tower console, a head-in viewers (2D or 3D), operating room monitors, console monitors, touchscreens, tower consoles, user input displays, or patient side interfaces.

Similarly, a haptic indicator may be used, which can include different patterns of vibration or resistance to indicate the temperature of the medical instrument. For example, an instrument handle, an instrument, or a user input (such as a gimbal, pedal, or controllers such as controller 182) can vibrate when the temperature of the medical instrument has reached a certain threshold. In another example, the user input or medical instrument can provide resistance until the temperature of the medical instrument has reached a certain threshold. The user input can also include indicators related to the thermal information of the medical instrument. In some examples, while a user input is selectively coupled to a medical instrument 250 that is configured to deliver heat, the user input can be configured to provide haptic indicators to the user to indicate the medical instrument 250 is at or above a certain temperature. For example, the controller 182 can vibrate or provide a haptic pattern to indicate the temperature is above or below a threshold. The user input can also provide haptic resistance if the temperature is above a threshold, thus preventing the user from moving the coupled medical instrument until the temperature falls below a temperature threshold. The user input can provide haptic feedback that a medical instrument 250 is sufficiently cooled to move or engage tissue. The user input can also provide haptic feedback that the medical instrument is ready to or is not ready to be fired or heated.

The indicators described herein can be considered "dynamic" because, in some examples, the indicators can change based on a variety of factors, including, for example, a user input, a state of the robotic system, a state of a component of the robotic system (such as a state of a robotic arm, a state of a robotic medical instrument, etc.), and/or a type of medical procedure being performed, among other factors. In some examples, the system is configured to determine a state of the robotic system and adjust the dynamic indicators accordingly based on the determined state. In some examples, the indicators can be used to indicate when a medical instrument has changed from one state to another (e.g., from a first temperature to a second temperature or from a non-operational state to an operational state). Thus, in certain situations, the indicators on the viewer 300 may display in one way, and in different situations, the indicators on the viewer 300 may display in a different way. For example, the indicators on the viewer 300 can be displayed around the image of the medical instrument when the controllers 182 are selectively coupled to the medical instrument. This offers improved functionality and control over previous systems, which have generally relied on a user's expertise and judgement.

In some examples, the indicators can be visual indicators, such as image overlays, as described above. The visual indicator can also be on a viewer as described herein (e.g. the viewers 300 as shown in FIG. 23A-23B, 24A-24B, 25A-25B, 26A-26B, or 27A-27B). The image overlays can be positioned on an image of a medical instrument and/or an treatment site, which may be a live feed or a representative model or depiction. In some examples, the indicators can be other types of visual indicators (such as lights, screens, or other displays) that can communicate information to a user. Visual indicators can be, for example, in the form of direct lighting, up-lighting, back-lighting, LED panels, screens, or any combination thereof. In some embodiments, the visual indicators can be configured to change patterns (e.g., a blinking or flashing pattern) and/or change intensity or brightness.

The visual indicators can be positioned in various places. In some examples, the indicators can be displayed on viewers, which may be a display or screen for displaying text, images or other symbols. The viewers as described can be positioned on a number of locations, such as a head-in viewers (2D or 3D), operating room monitors, console monitors, touchscreens, tower consoles, user input displays, or patient side interfaces. In some examples, the visual indicators can be displayed directly on a medical instrument 250, such as by a ring of light positioned on or within the medical instrument 250. The indicators can be directly on the medical instrument 250, such as the distal end, wrist 230, or shaft 252 of the medical instrument 250. The medical instrument 250 can also include a screen configured to displaying text or other symbols. The medical instrument 250 can include lights positioned on the medical instrument 250. Further, a ring or light can be positioned in any number of locations in the robotic system, such as on a user input, a controller, a robotic arm, an instrument base, or a bed rail. Other visual indicators can include light emitting diodes, lasers, or moveable colored markers. For example, the medical instrument 250 may include an associated light, which may be positioned anywhere on the medical instrument 250, such as the wrist 230 or distal shaft 252. The associated light may be a ring light or a light positioned on a surface of the medical instrument 250. The color or pattern of the light may indicate a temperature of the medical instrument 250. In some examples, a viewer (such as viewers 300 as shown in FIG. 23A-23B, 24A-24B, 25A-25B, 26A-26B, or 27A-27B) may then display an image of a medical instrument 250 which includes a visual indicator directly on the medical instrument 250.

Further, although only one viewer 300 is shown in each of the illustrated embodiments in FIG. 23A-23B, 24A-24B, 25A-25B, 26A-26B, or 27A-27B, other numbers of viewers are also possible. The indicators can be configured to update and display information contextually based on a variety of factors related to the robotic system as described. Different shading or cross-hatching has been used to illustrate different indicators that can be provided by the indicators (e.g., indications of different colors).

The indicators can convey information related to the temperature of the medical instrument in a variety of ways. The indicators can be capable of displaying multiple colors or patterns. In some examples, a first color or pattern can be used to indicate the medical instrument is heated and a second color or pattern can be used to indicate the medical instrument is cooled. In some examples, opacity, intensity, or brightness of the colors or patterns can also be used to indicate temperature. In some examples, the indicator can display multiple colors or patterns that continually transition from a first color or pattern to a second color or pattern. In some examples, the indicator can display a first color or pattern until the medical instrument reaches a temperature threshold and a second color or pattern reaches the temperature threshold.

In one example, the indicator can start with one color (e.g., red) and then continually change color until a safe color (e.g., green) is reached. In another example, the indicator can start with one color (e.g., red) and then only change to a safe color (e.g., green) when a desired temperature is reached. In addition, it is possible to add a temperature number (e.g., 70 degrees) adjacent to the visual indicators that can change.

In some examples, the indicator can include text (e.g. "cool down") to indicate the progress of the temperature of the medical instrument. For example, the indicator can include a temperature meter to indicate the temperature of the medical instrument. The indicator can also include a number indicating the temperature of the medical instrument. The indicator can include a time until the medical instrument is estimated to reach a temperature threshold. The indicator can also include a time that has elapsed since the medical instrument has been fired to provide resistive heat.

In addition, while the type of communication can be visual, audible, or haptic, these types of communications can also be combined. For example, an indicator can go from red to green, and upon reaching green, an audible signal is generated to the clinician or a corresponding haptic vibration can be generated in the medical instrument or controller.

The indicator may be communicated at various times. In some examples, the indicator can be communicated at all times. In some examples, the indicator may be communicated when a medical instrument is selectively engaged or coupled with a user input. In other examples, the indicator may be communicated when the medical instrument has been fired or activated to deliver heat. The indicator may be communicated when other instruments are activated. The indicator may be communicated when a temperature of a medical instrument is above, below, or is at a certain threshold. This threshold may comprise or otherwise relate to the threshold temperature at which the medical instrument is ready to activated or may be a different threshold.

Different types of indicators may be used together, e.g., simultaneously. For example, when a visual indicator is changed from one pattern or color to another pattern or color, it can be accompanied by an audio indicator or a change in audio indicator from a first tone to a second tone. In some examples, different types of visual indicators can be used, such as multiple image overlays or image overlay and lights.

Figure 28:
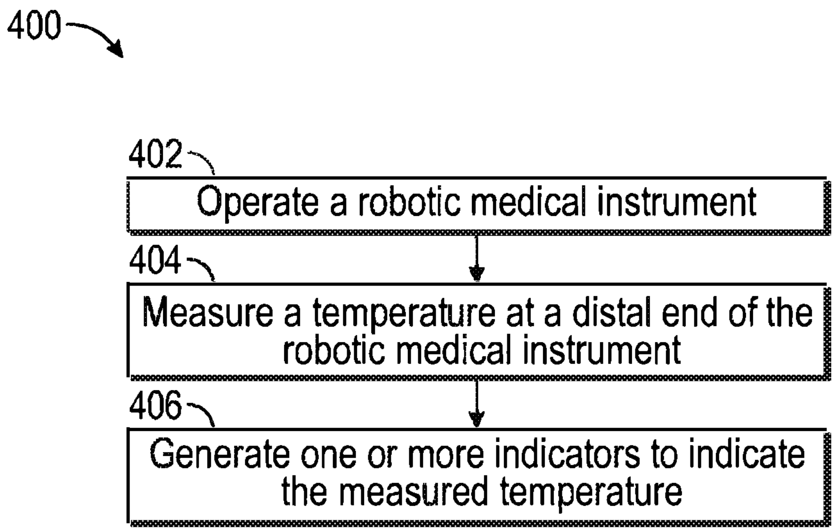
FIG. 28 is a flow chart depicting an example method for implementing indicators regarding heat for a robotic medical system.

FIG. 28 illustrates an example method 400 for implementing indicators on a robotic medical system as described herein. The method 400 begins at block 402, which includes operating a robotic medical instrument. As described above, medical instruments can be engaged with and controlled by a robotic manipulator. As described above, the medical instrument can include a jaws a distal end, which can be heated by electrical current to deliver thermal energy to tissue. Operating the robotic medical instrument can include delivering energy to tissue at a treatment site. For example, an operator can control an energy or heat delivery device to navigate to a desired target area within a patient, grasp tissue at the desired target area, and activate or fire the medical instrument to deliver energy or heat for one or more steps of a medical procedure (such as, e.g., cutting or sealing).

At block 404, the method 400 includes determining a temperature at a distal end of the robotic medical instrument. In some examples, the temperature of the distal end of the robotic medical instrument can be measured by a temperature sensor. As described herein, the temperature sensor can be placed in various positions in the system, such as at the distal end of the medical instrument to directly measure the temperature. In some examples, the temperature can be measured directly at the jaws, the wrist, or the shaft of the medical instrument. In some examples, the temperature can also be based on other variables, such as known characteristics of the medical instrument, including firing time, thermal decay constant, or external or intracorporeal body temperature. In some examples, the temperature can be compared to a threshold. For example, the threshold can be a predetermined temperature at which the medical instrument is safe to engage tissue or fire again. In some examples, the threshold can be 60 degrees Celsius. In some examples, the threshold can be about 75, 70, 65, 55, 50, 45, 40, 35 or 30 degrees Celsius.

At block 406, the method 400 includes generating one or more indicators to indicate the determined temperature. As described above, the one or more indicators can be visual, haptic, or audible or any combination thereof. For example, in some examples, the indicators can be visually displayed on a viewer (e.g., as shown in FIG. 23A-23B, 24A-24B, 25A-25B, 26A-26B, or 27A-27B). In some examples, the one or more indicators can include an image overlay that conveys information regarding the determined or measured temperature, the image overlay can be display on an image or representation of the medical instrument. The indicators can convey information related to the measured temperature, such as the temperature value itself, if the temperature is above or below a threshold, or the time to allow the medical instrument to cool before it is ready for activation.

Figure 29:
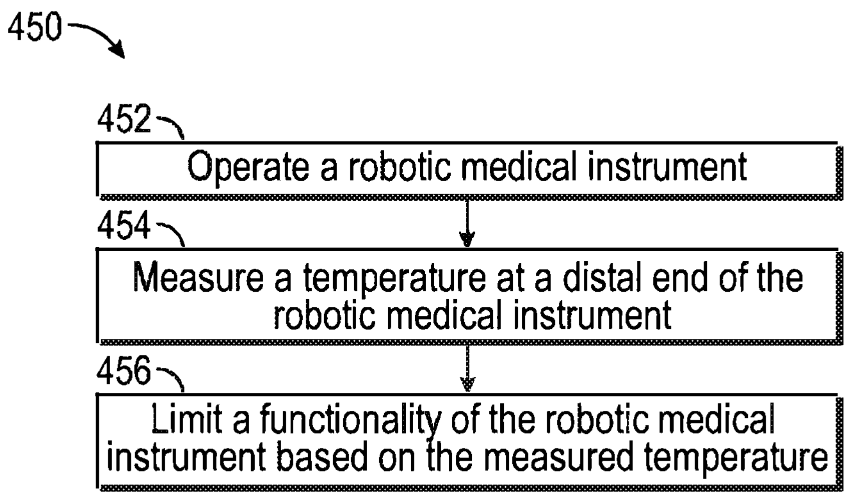
FIG. 29 is a flow chart depicting an example method for controlling a robotic medical instrument.

FIG. 29 illustrates an example method 450 for controlling a robotic medical instrument. The method 450 begins at block 452, which includes operating a robotic medical instrument. The robotic medical instrument can be operated in a number of different ways, such as those described above.

At block 454, the method 450 includes determining at temperature at a distal end of the robotic medical instrument. The temperature can be determined in a number of different ways, such as those described above.

At block 456, the method 450 includes limiting a functionality of the robotic medical instrument based on the determined temperature from block 454. For example, functionality can be limited or resistive. In some examples, limiting a functionality of the robotic medical instrument can be considered haptic feedback. For example, the robotic medical instrument can resist movement as a form of limited functionality, which can also cause resistance in the controller being operated by a user. The functionality can be limited after a certain amount of time or until the determined temperature falls below a temperature threshold. In some embodiments, limiting a functionality of the robotic medical instrument can also include turning on or off the instrument, or modifying its ability to generate energy.

In some examples, a feature of the instrument can be adjusted or modified based on the determined temperature. For example, an availability of the feature of the instrument may be reduced or modified based on the determined temperature. This limited functionality may be temporary, such as based on the determined temperature or based on a predetermined amount of time. The functionality or feature to be limited can include the speed, direction, movement of the robotic medical instrument. In some examples, limiting functionality can include preventing actuation of the robotic medical instrument, such as preventing movement of the jaws or portion of the medical instrument or preventing firing of the medical instrument.

In some examples, a controller or processor of the system can receive a signal including the determined temperature of the distal end of the robotic medical instrument. The controller or processor may then determine the determined temperature is above or below a certain threshold. Based on this determination, the controller or processor may then generate and send a signal to limit the functionality of the medical instrument. In some examples, the signal may be sent to the medical instrument to prevent movement, actuation, heat generation, activation, or any other features of the medical instrument. In some examples, the signal may be sent to a user input, such as a controller, to prevent a user from moving, actuating, or activating the medical instrument with the user input. In some examples, the signal may be sent to a user input to generate haptic resistance of the user input. For example, haptic resistance in the user input can prevent or inhibit movement of the user input (and thereby preventing or inhibiting movement of the medical instrument).

Furthermore, although limiting functionality and generating indicators are described in different methods, these features may be used simultaneously. For example, an indicator in the form of a visual or audible alarm can be generated while functionality of the medical instrument is limited when the temperature is above a certain threshold.

A. Thermal Distance Indicator.

In some embodiments, the one or more indicators are generated based on (i) a distance between a distal end of a robotic medical instrument and a tissue as well as (ii) the temperature of the distal end of the robotic medical instrument. Utilizing the distance information in addition to the temperature information, the one or more indicators are provided only when the temperature is at and/or above a critical temperature and the distance is less than a critical distance, thereby reducing the frequency of, or eliminating, the one or more indicators when the risk of an injury is low. For example, even if a robotic medical instrument (e.g., a thermal instrument) is at a high temperature (e.g., at a temperature above a critical temperature), if the robotic medical instrument is positioned sufficiently away from the tissue, the risk of inadvertently injuring the tissue is low. Reducing the frequency of, or eliminating, the one or more indicators when the risk of an injury is low reduces distraction to the physician operator performing the surgical procedure, allowing the physician operator to continue to focus on the surgical procedure.

Figure 30:
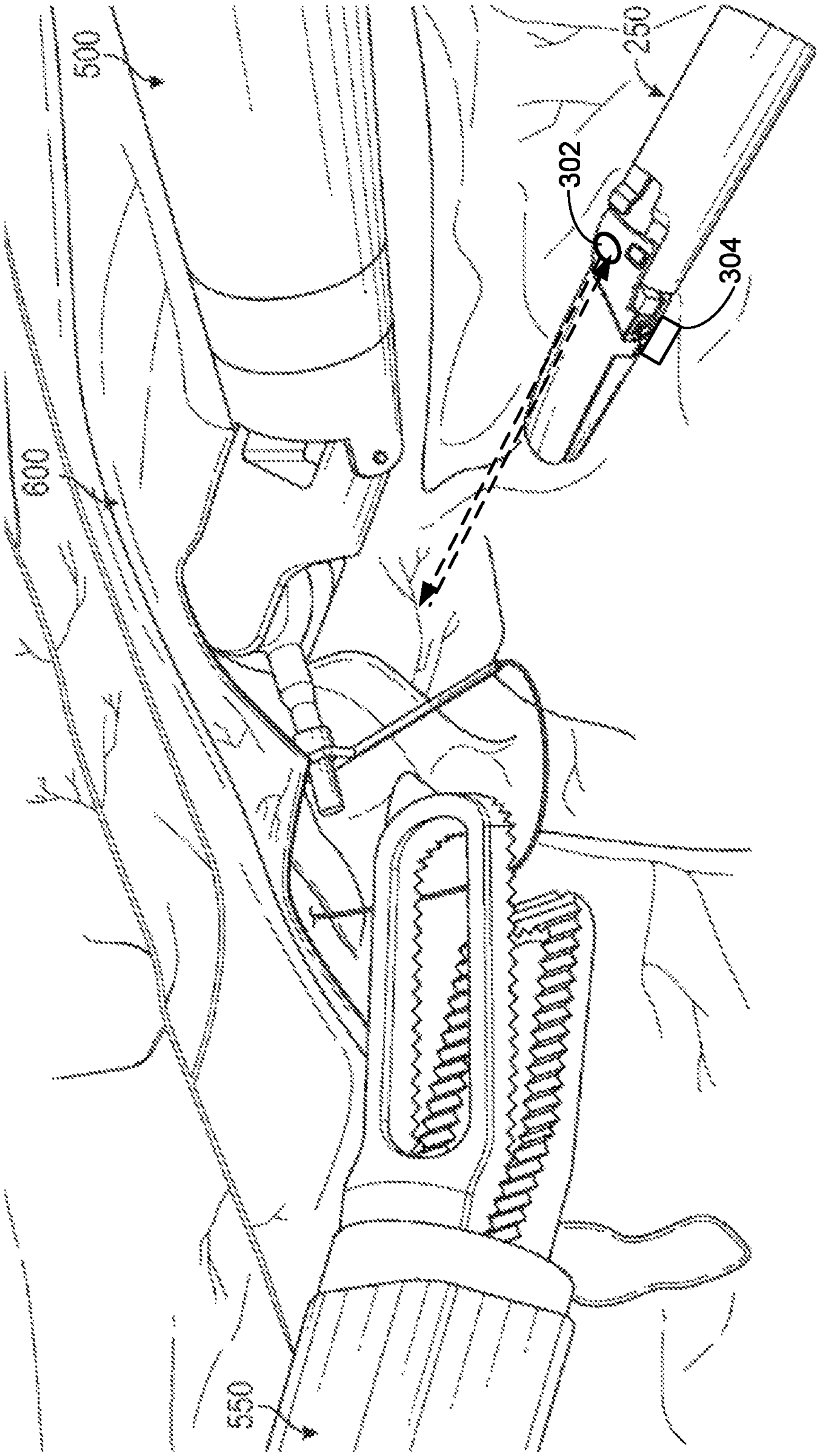
FIG. 30 illustrates a temperature sensor and a distance sensor positioned on a thermal instrument in accordance with some embodiments.

FIG. 30 illustrates a temperature sensor and a distance sensor positioned on the medical instrument 250 in accordance with some embodiments. As described with respect to FIG. 21A, in some embodiments, the medical instrument 250 delivers thermal energy to tissue for a variety of surgical tasks, such as dissection, cutting, ligation, and/or sealing. Thus, in some embodiments, the medical instrument 250 is also called a thermal instrument. Examples of the thermal instrument 250 can include a hot knife, a laser, a monopolar electrocautery instrument, or a bipolar electrocautery instrument.

In FIG. 30, a distance sensor 302 is positioned on the thermal instrument 250 to determine a distance between the thermal instrument 250 to an adjacent tissue. The distance sensor 302 may detect the distance between the thermal instrument 250 and the adjacent tissue using one or more of a variety of distance sensing methods. For example, the distance sensor 302 can determine a distance to the tissue using projection of structured light for depth sensing, time-of-flight sensing (e.g., based on light or sound), or Light Detection And Ranging (LIDAR). In some embodiments, the distance sensor 302 can also determine a shape (or profile) of the tissue in addition determining the distance.

In some embodiments, the distance is measured from a tip of the thermal instrument (e.g., a tip of the instrument end effector) to an outer surface of an adjacent tissue. In some embodiments, the distance between a side of the thermal instrument (e.g., a side of the instrument end effector) to an outer surface of an adjacent tissue is measured in addition to the distance between the tip of the thermal instrument to an outer surface of an adjacent tissue. In some embodiments, the distance between any thermally operative portion of the thermal instrument 250 (e.g., any surface with an increased temperature) and an adjacent tissue is measured. The measured distance is used in conjunction with the temperature information to provide a thermal distance warning. In some embodiments, when multiple distances are measured, a shorted distance between the thermal instrument and the surrounding tissue is used. In some embodiments, when multiple distances are measured, the distance between the thermal instrument and the surrounding tissue in a direction that corresponds to a direction that the thermal instrument is to advance is used (e.g., when an input for advancing the thermal instrument along the longitudinal axis of the thermal instrument is received, the distance between the thermal instrument and the surrounding tissue along the longitudinal axis of the thermal instrument is used).

Although FIG. 30 illustrates the distance sensor 302 positioned on a proximal location of the jaws of the thermal instrument 250, the distance sensor 302 may be positioned on the jaws (e.g., integrated with the jaws), or any other place on the thermal instrument 250. In addition, although FIG. 30 illustrates only one distance sensor 302, two or more distance sensors (e.g., an array of distance sensors) may be positioned on the thermal instrument 250.

FIG. 30 also illustrates a temperature sensor 304 positioned on the thermal instrument 250. The temperature sensor 304 detects the temperature of the thermal instrument 250 (e.g., the temperature of a tip of the instrument end effector). In some embodiments, the temperature sensor 304 also detects the temperature of adjacent or surrounding tissue. In some embodiments, the temperature sensor 304 includes one or more thermocouples. For example, multiple thermocouples may be positioned on or adjacent to any thermally operative portion of the thermal instrument 250.

Figure 31:
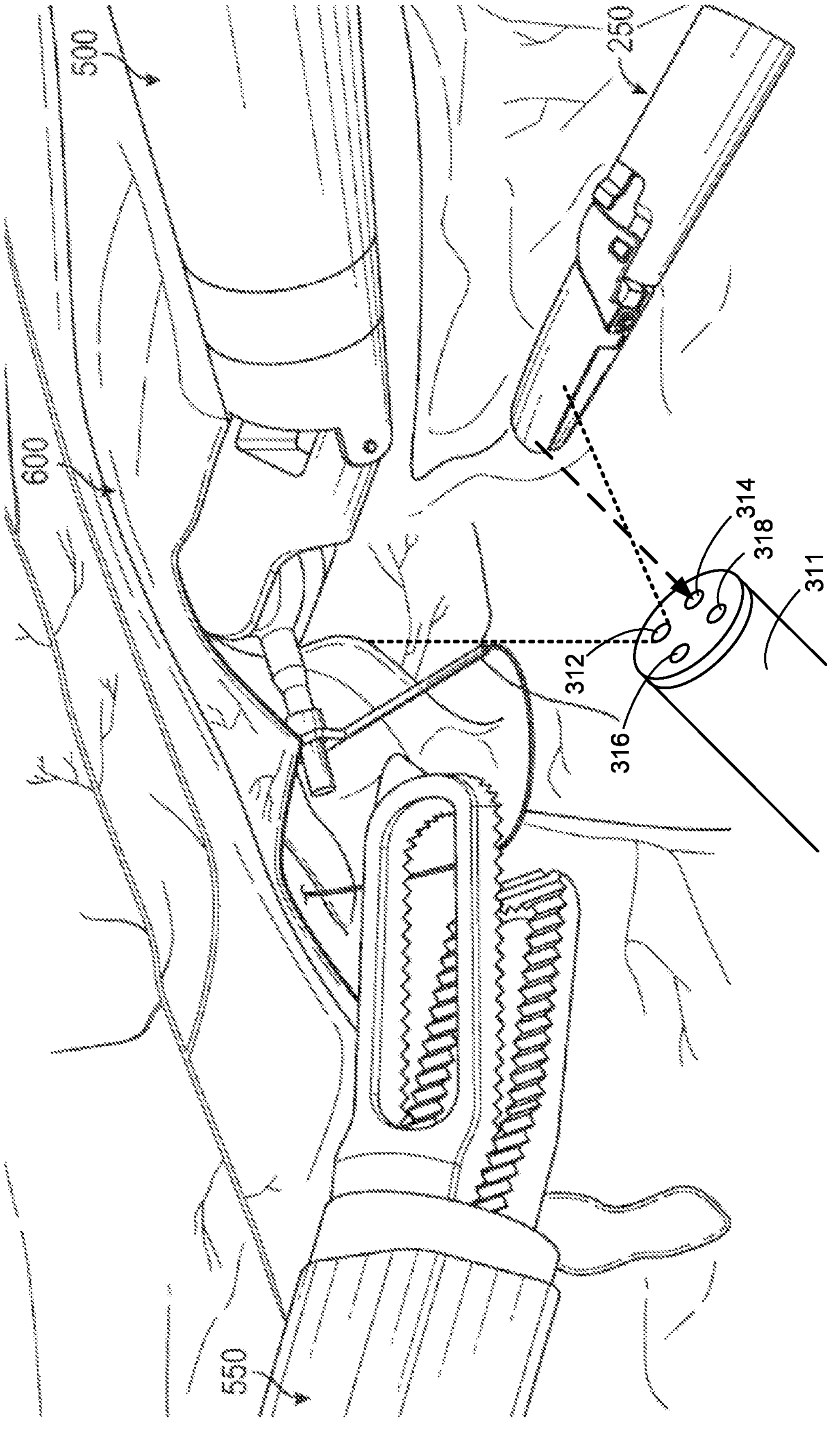
FIG. 31 illustrates a temperature sensor and a distance sensor positioned away from a thermal instrument in accordance with some embodiments.

FIG. 31 illustrates a distance sensor 312 and a temperature sensor 314 positioned away from a thermal instrument 250 in accordance with some embodiments.

In some embodiments, the distance sensor 312 and the temperature sensor 314 are coupled with (e.g., integrated with) a scope 311 that is distinct and separate from the thermal instrument 250. The distance sensor 312 coupled with the scope 311 is capable of detecting a distance between the thermal instrument 250 and the adjacent tissue. In some embodiments, the distance sensor 312 includes a depth sensor capable of detecting a three-dimensional profile of the tissue adjacent to the thermal instrument 250 (e.g., by projecting structured light from a light source 316), LIDAR, or stereoscopic imaging cameras 318. In some embodiments, the temperature sensor 314 is capable of detecting infrared light (e.g., the temperature sensor 314 includes an infrared sensor), which can be used to determine the temperature of an object (e.g., the thermal instrument 250 or the surrounding tissue). In some embodiments, the temperature sensor 314 includes an imaging camera coupled with an array of infrared sensors for concurrently detecting the temperature of the thermal instrument 250 and the surrounding tissue.

Although FIG. 30 illustrates the distance sensor 302 and the temperature sensor 304 positioned on the thermal instrument 250 and FIG. 31 illustrates the distance sensor 312 and the temperature sensor 314 positioned away from the thermal instrument 250, in some embodiments, a combination of on-and-off sensors may be used. For example, a medical system may include the distance sensor 312 positioned away from the thermal instrument 250 and the temperature sensor 304 on the thermal instrument 250. Alternatively, the medical system may include the distance sensor 302 positioned on the thermal instrument 250 and the temperature sensor 314 positioned away from the thermal instrument 250. In some embodiments, the medical system includes both the distance sensor 302 positioned on the thermal instrument 250 and the distance sensor 312 positioned away from the thermal instrument 250 as well as both the temperature sensor 304 positioned on the thermal instrument 250 and the temperature sensor 314 positioned away from the thermal instrument 250. In some embodiments, any combination of the distance sensor 302, the distance sensor 312, the temperature sensor 304, or the temperature sensor 314 may be used in a medical system.

Figure 32:
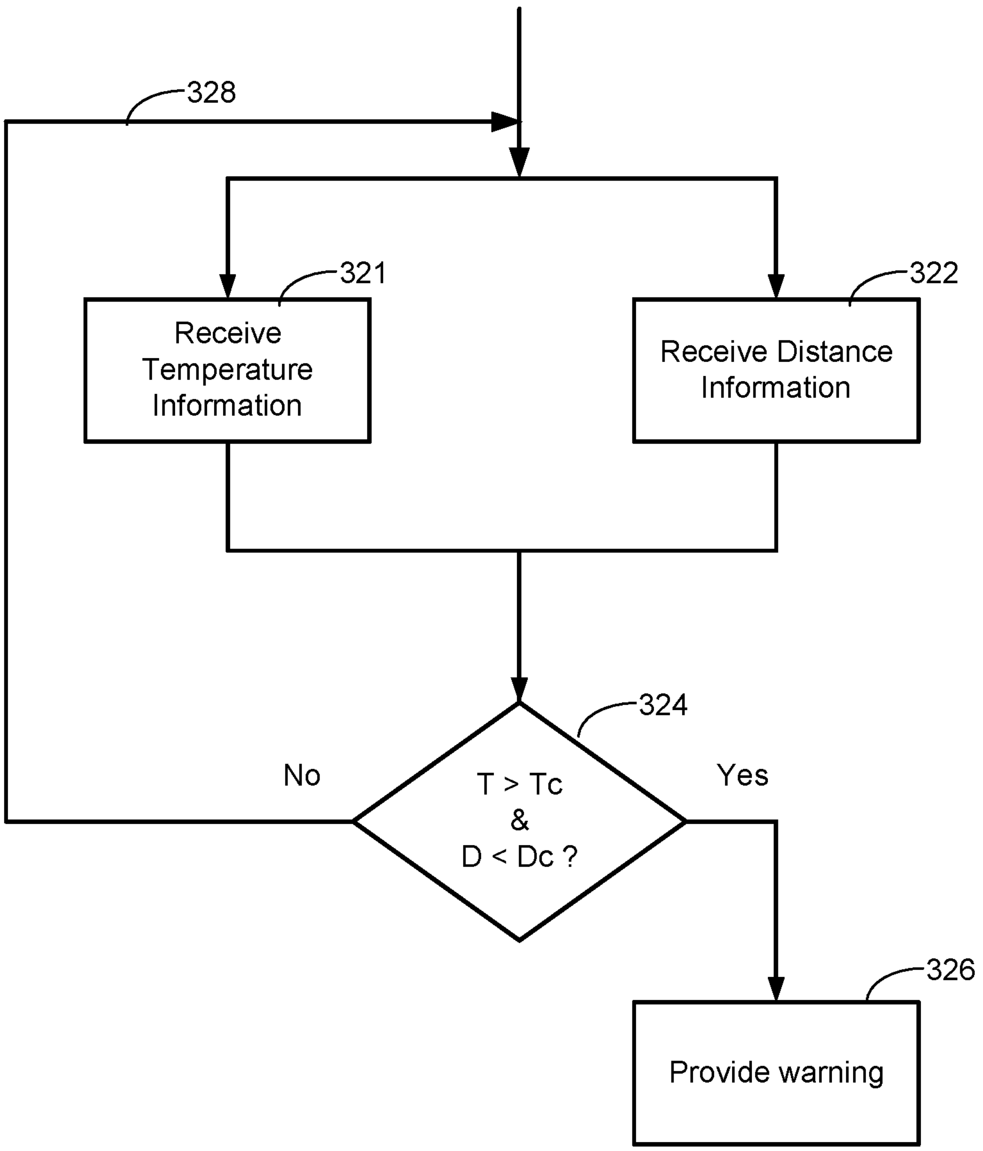
FIG. 32 is a flow diagram illustrating a method for providing a thermal distance warning in accordance with some embodiments.

FIG. 32 is a flow diagram illustrating a method for providing a thermal distance warning in accordance with some embodiments. One or more processors of a medical system receive (321) temperature information of the thermal instrument 250 and receive (322) distance information indicating a distance between the thermal instrument 250 and the surrounding tissue. The one or more processors compare (324) the temperature, T, of the thermal instrument 250 indicated by the temperature information with a critical temperature, Tc (also called a threshold temperature), and determine whether the temperature of the thermal instrument 250 exceeds the critical temperature. In addition, the one or more processors compare the distance, D, between the thermal instrument 250 and the surrounding tissue with a critical distance Dc (also called a threshold distance) and determine whether the distance between the thermal instrument 250 and the surrounding tissue is less than the critical distance Dc. If the temperature of the thermal instrument 250 is greater than (or equal to) the critical temperature and the distance between the thermal instrument 250 and the surrounding tissue is less than (or equal to) the critical distance, the one or more processors causes (326) a warning to be provided (e.g., by sending one or more signals to a device capable of providing a warning, such as a visual or haptic warning, to provide a thermal distance warning indicating that a thermal instrument having a temperature above the critical temperature is positioned with a distance less than the critical distance from the surrounding tissue). In some embodiments, if the temperature of the thermal instrument 250 is less than the critical temperature or the distance between the thermal instrument 250 and the surrounding tissue is greater than the critical distance, the one or more processors continue to monitor the temperature of the thermal instrument 250 and the distance between the thermal instrument 250 and the surrounding tissue without a warning.

Figure 33A:
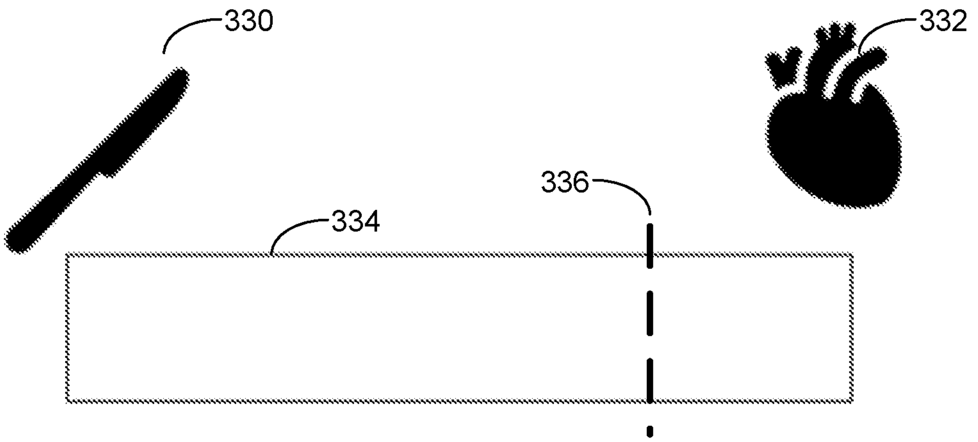
FIGS. 33A-33C illustrate an example thermal distance indicator in accordance with some embodiments.
Figure 33B:
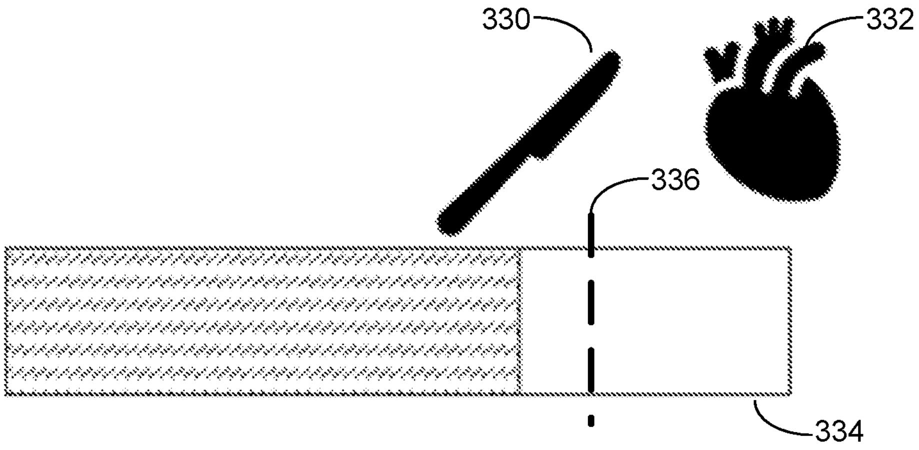
Figure 33C:
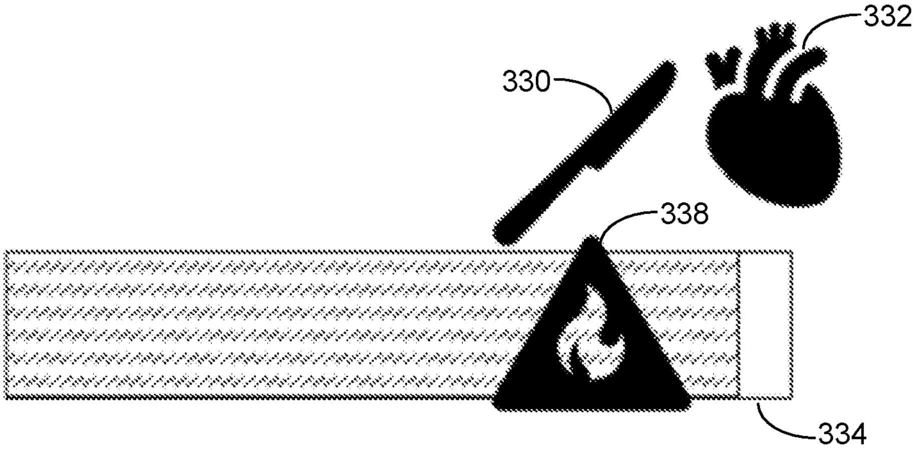

FIGS. 33A-33C illustrate an example of a thermal distance indicator used for providing a warning in accordance with some embodiments. The thermal distance indicator shown in FIGS. 33A-33C is a graphical representation with multiple graphical objects, such as a thermal instrument icon 330, a tissue or organ icon 332, a distance indicator 334, and a distance threshold indicator 336. The graphical representation may include additional graphical objects, or fewer graphical objects. The thermal distance indicator shown in FIGS. 33A-33C may be displayed in a display device (e.g., a monitor, a liquid crystal display, a cathode ray tube display, etc.).

The thermal distance indicator shown in FIG. 33A illustrates a state in which a thermal instrument is positioned away from the surrounding tissue. The distance indicator 334 in FIG. 33A includes a bar graph indicating a distance between the thermal instrument and the surrounding tissue.

FIG. 33B illustrates the thermal distance indicator for a state in which the distance between the thermal instrument and the surrounding tissue has decreased. In the thermal distance indicator of FIG. 33B, the thermal instrument icon 330 has moved toward the tissue icon 332, and the bar graph in the distance indicator 334 has decreased to indicate the reduced distance. In FIG. 33B, the distance between the thermal instrument and the surrounding tissue is greater than the critical distance represented by the distance threshold indicator 336, and no warning is provided.

FIG. 33C illustrates the thermal distance indicator for a state in which the thermal instrument is positioned within the critical distance from the surrounding tissue and the temperature of the thermal instrument is greater than the critical temperature. In FIG. 33C, the thermal instrument icon 330 has moved further toward the tissue icon 332 compared to FIG. 33B, and the bar graph in the distance indicator 334 has further decreased to indicate the further decreased distance between the thermal instrument and the surrounding tissue. In addition, the thermal distance indicator includes a warning object 338, which indicates the thermal instrument is positioned within the critical distance from the surrounding tissue and the temperature of the thermal instrument is greater than the critical temperature.

As described above, FIGS. 33A-33C illustrate the thermal distance indicator as a visual (e.g., graphical) warning to a user. In some embodiments, other types of warnings are generated in addition to, or instead of, the visual warning. For example, in response to determining that the thermal instrument is positioned within the critical distance from the surrounding tissue and the temperature of the thermal instrument is greater than the critical temperature, other types of warnings can be provided, such as a haptic warning (e.g., a vibrations or taps) or an audio warning (e.g., beeps or other preselected sound signals). In some embodiments, the warning is an electrical signal (e.g., a fault signal) used by a medical system to halt, pause, or slow down operations of a robotic arm or the thermal instrument (e.g., until the temperature of the thermal instrument falls below the critical temperature or the distance between the thermal instrument and the surrounding tissue increases above the critical distance).

Although FIGS. 33A-33C show the thermal distance indicator with a fixed distance threshold icon 336 (representing a constant distance threshold), in some embodiments, the distance threshold is adjusted. For example, the distance threshold may be adjusted based on a temperature of the thermal instrument. When the temperature of the thermal instrument is excessively high, the system can modify the distance threshold such that it can be greater to accommodate the high temperature. By enabling a dynamic distance threshold based on the temperature of the thermal instrument, the thermal distance indicator can provide information that more accurately represents the risk of thermal injury.

Figure 34A:
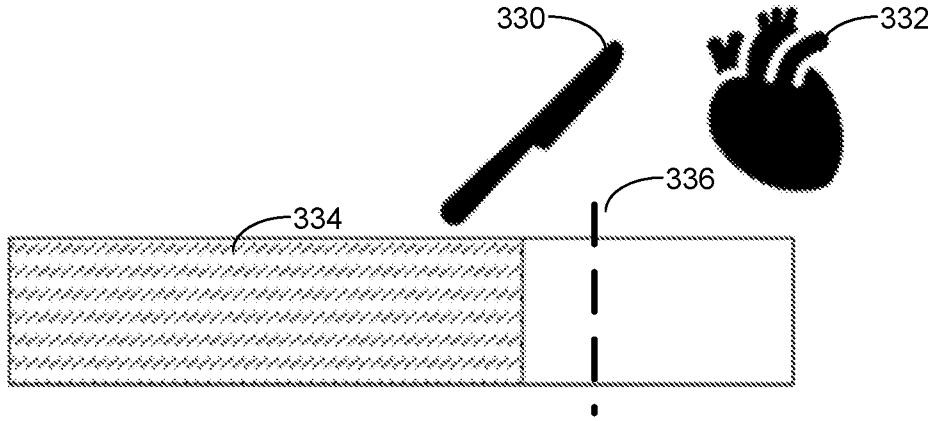
FIGS. 34A-34C illustrate adjusting a distance threshold in a thermal distance indicator in accordance with some embodiments.
Figure 34B:
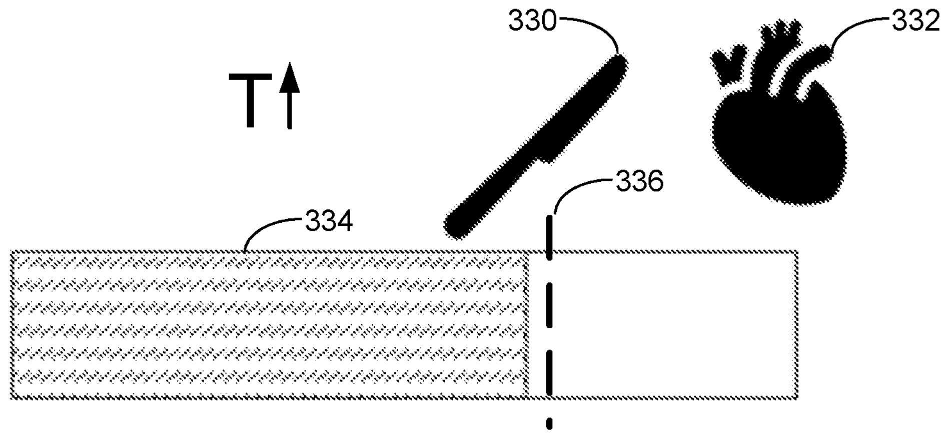
Figure 34C:
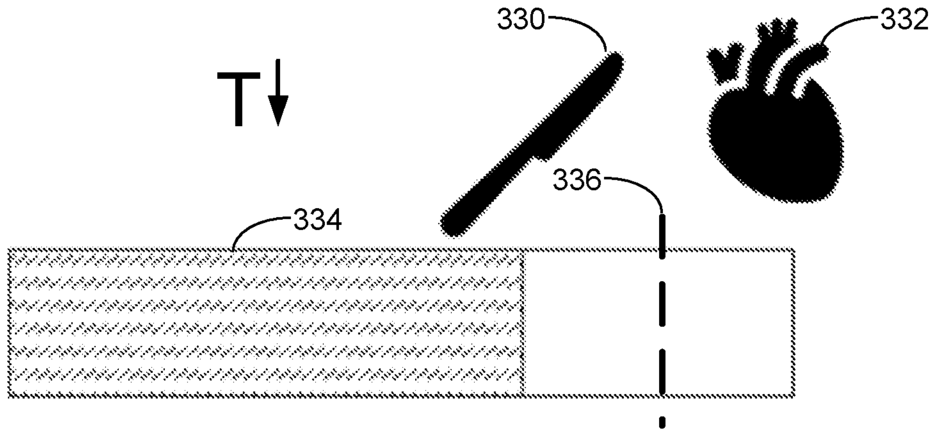

FIGS. 34A-34C illustrate adjusting a distance threshold in a thermal distance indicator in accordance with some embodiments. FIG. 34A corresponds to FIG. 33B, which illustrates a thermal distance indicator for a state in which the thermal instrument is adjacent to the surrounding tissue (but the distance between the thermal instrument and the surrounding tissue is greater than the critical distance).

FIG. 34B illustrates that the temperature of the thermal instrument has increased (e.g., due to an activation of the thermal instrument) and the distance threshold indicator 336 has moved (e.g., toward left) to indicate the increased critical distance. As a result, the margin between the current distance and the critical distance has decreased even when the distance between the thermal instrument and the surrounding tissue has not changed. If the temperature of the thermal instrument continues to increase, the critical distance can continue to increase and the distance between the thermal instrument and the surrounding tissue may fall short of the critical distance, which, in turn, triggers a warning even without any movement of the thermal instrument.

FIG. 34C illustrates that the temperature of the thermal instrument has decreased (e.g., due to the cooling of the thermal instrument over tie) and the distance threshold indicator 336 has moved (e.g., toward right) to indicate the decreased critical distance. As a result, the margin between the current distance and the critical distance has increased even when the distance between the thermal instrument and the surrounding tissue has not changed. If the temperature of the thermal instrument continues to decrease, the critical distance can continue to decrease.

In some embodiments, the critical distance, Dc, is mathematically described as a function of the temperature of the thermal instrument, T:

$$Dc = f(T)$$

For example, Dc may decrease substantially linearly as a function of T:

$$Dc = Dc_0 - k \cdot \min(0, T - T_0)$$

where k is a slope of Dc as a function of T, and $T_0$ is a temperature above which the critical distance is reduced.

In another example, Dc decreases nonlinearly as a function of T:

$$Dc = Dc_0 - k \cdot \min(0, (T - T_0)^p)$$

where p is a positive number other than 1.

Figure 35:
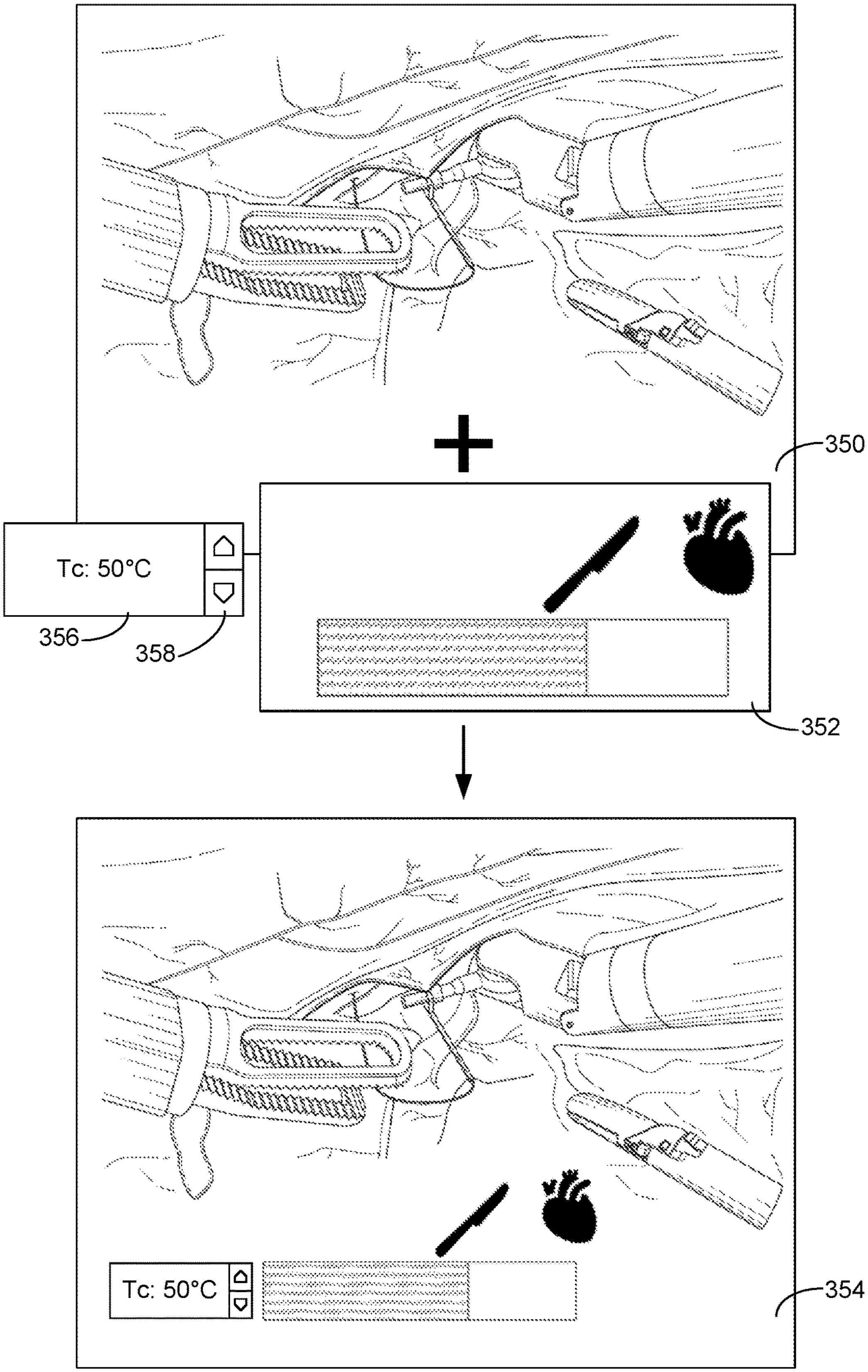
FIG. 35 illustrates generating a combined image including a thermal distance indicator in accordance with some embodiments.

In some embodiments, the thermal distance indicator shown in FIGS. 33A-33C and 34A-34C is displayed in the form of a graphical overlay. FIG. 35 illustrates generating a combined image including a thermal distance indicator in accordance with some embodiments. For example, an image 350 of a surgical site (e.g., collected by an imaging scope delivered to the surgical site) is received and a graphical representation 352 of the thermal distance indicator is generated. A combination of the image 350 of the surgical site and the graphical representation 352 of the thermal distance indicator is generated by laying the graphical representation 352 over the image 350 of the surgical site. The combined image 354 is provided to a display device for presentation of a user (e.g., a physician operator).

In some embodiments, the combined image 354 also includes a user interface object 356 for indicating the critical temperature and one or more user interface objects 358 for adjusting the critical temperature.

B. Activation/Deactivation of Thermal Distance Indicator.

As described above, the combination of temperature information and distance information of a thermal instrument can advantageously increase the safety of a robotic medical system. In some scenarios, it may be beneficial for a thermal instrument to be continuously activated. For example, when a surgeon is using a thermal instrument for cauterization (e.g., in surgery of the large or small bowel, isolating the mesentery for removal in the lower gastrointestinal tract, or bariatrics for the upper gastrointestinal tract, among other types of surgical procedures), the surgeon may want to use the thermal instrument in a repeated fashion to create an elongated zone of cauterized thermal dissection. In such cases whereby the thermal instrument would be continuously activated, turning off or delaying the warning notification can limit the potential for distraction to the surgeon by removing warnings while the surgeon is performing intended repetitive dissection and sealing using the thermal instrument.

Figure 36A:
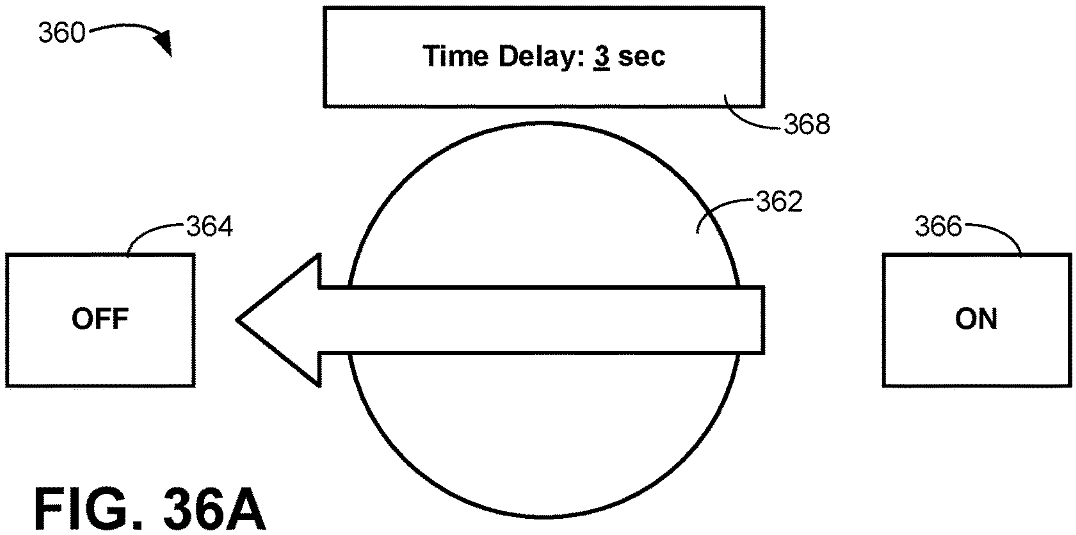
FIGS. 36A-36C illustrate user interface objects associated with controlling operations of a thermal distance indicator in accordance with some embodiments.
Figure 36B:
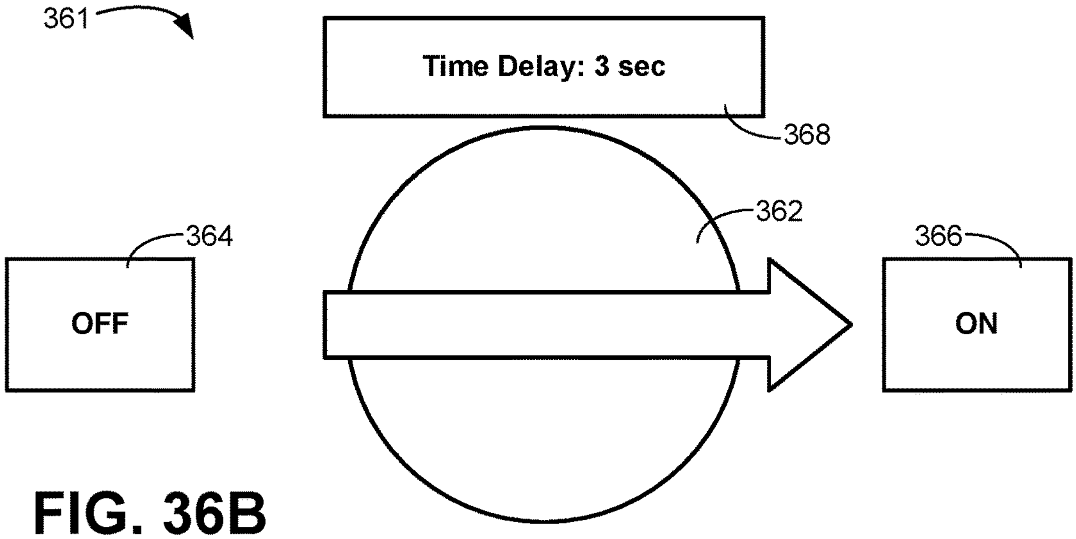
Figure 36C:
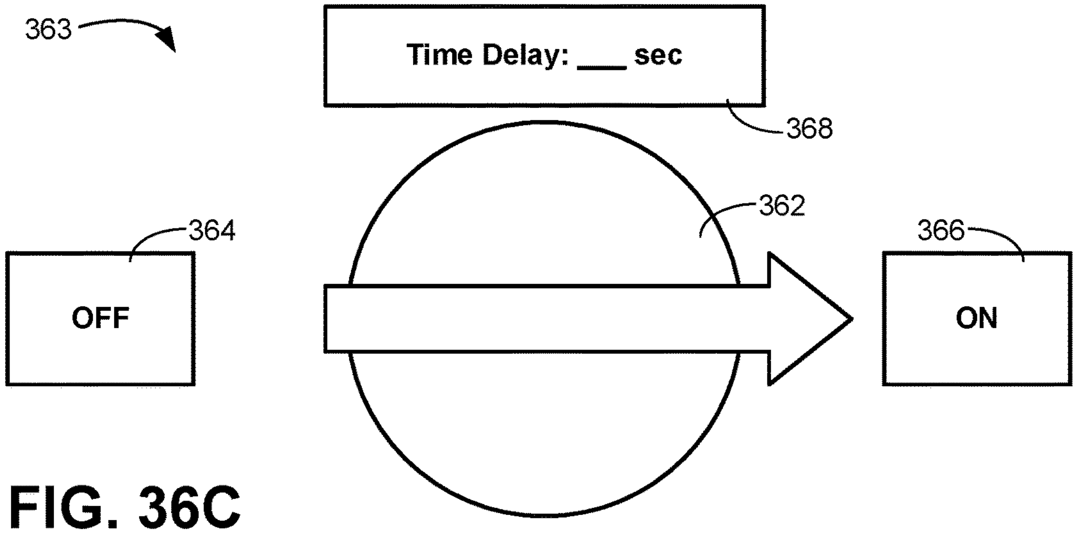

In some embodiments, a user interface is used to turn off or delay the warning notification. FIGS. 36A-36C illustrate user interface objects associated with controlling operations of a thermal distance indicator in accordance with some embodiments. A user interface 360 shown in FIG. 36A includes a state indicator 362 (e.g., a knob), an off state indicator 364, an on state indicator 366, and a delay time indicator 368, where the state indicator 362 points to the off state indicator 364, indicating that the thermal distance indicator is turned off (and the medical system is not in a thermal distance indication mode). In FIG. 36A, the delay time indicator 368 indicates the time delay of 3 seconds. In some embodiments, while the state indicator 362 points to the off state indicator 364, the delay time indicator 368 ceases to be displayed, is de-highlighted (e.g., greyed out or faded), or highlighted (e.g., the borders of the delay time indicator 368 are highlighted with a dark color or the delay time indicator 368 is shaded with a dark color).

FIG. 36B illustrates a user interface 361 that is similar to the user interface 360, except that the state indicator 362 points to the on state indicator 366, indicating that the thermal distance indicator is turned on (and the medical system is in the thermal distance indication mode). In some embodiments, the medical system switches from the user interface 360 to the user interface 361 in response to detecting a user input requesting that the thermal distance indicator is in the on state. In some embodiments, the user input is received on one or more physical input devices (e.g., physical buttons, knobs, keys, switches, etc.) of the medical system. In some embodiments, the user input is received on one or more input affordance on a display or corresponding regions of a touch-sensitive surface. For example, the medical system may activate the thermal distance indicator in response to receiving a mouse click while a cursor is at a location corresponding to the on state indicator 366, and the medical system may deactivate the thermal distance indicator in response to receiving a mouse click while a cursor is at a location corresponding to the off state indicator 364. In another example, the medical system may activate the thermal distance indicator in response to receiving a touch input (e.g., a tap gesture) at a location of a touch-sensitive surface (e.g., a touch-sensitive display) corresponding to the on state indicator 366, and the medical system may deactivate the thermal distance indicator in response to detecting a touch input (e.g., a tap gesture) at a location of the touch-sensitive surface corresponding to the off state indicator 364. In yet another example, the medical system may activate the thermal distance indicator in response to receiving a touch input (e.g., a tap gesture or a clockwise rotation gesture) at a location of a touch-sensitive surface (e.g., a touch-sensitive display) corresponding to the state indicator 362, and the medical system may deactivate the thermal distance indicator in response to detecting a touch input (e.g., a tap gesture or a counter-clockwise rotation gesture) at a location of the touch-sensitive surface corresponding to the state indicator 362.

FIG. 36C illustrates a user interface 363 that is similar to the user interface 361, except that the delay time indicator 368 does not indicate the length of delay. In some embodiments, the medical system displays the user interface 363 in response to detecting a user input requesting clearing or resetting of the length of delay. In some embodiments, the user input is received on one or more physical input devices (e.g., physical buttons, knobs, keys, switches, etc.) of the medical system. In some embodiments, the user input is received on one or more input affordances on a display or corresponding regions of a touch-sensitive surface. For example, the medical system may reset the length of delay in response to receiving a mouse click while a cursor is at a location corresponding to the delay time indicator 368. In another example, the medical system may reset the length of delay in response to detecting a touch input (e.g., a tap gesture) at a location of a touch-sensitive surface corresponding to the delay time indicator 368. In some embodiments, the medical system, after resetting the length of delay, receives subsequent user inputs to set a new length of delay. For example, the medical system may receive a physical input (e.g., inputs on a keypad) to set the new length of delay. In another example, the medical system may display one or more user interface objects (e.g., number objects or a number picker, such as a number wheel) to receive the new length of delay.

Figure 37:
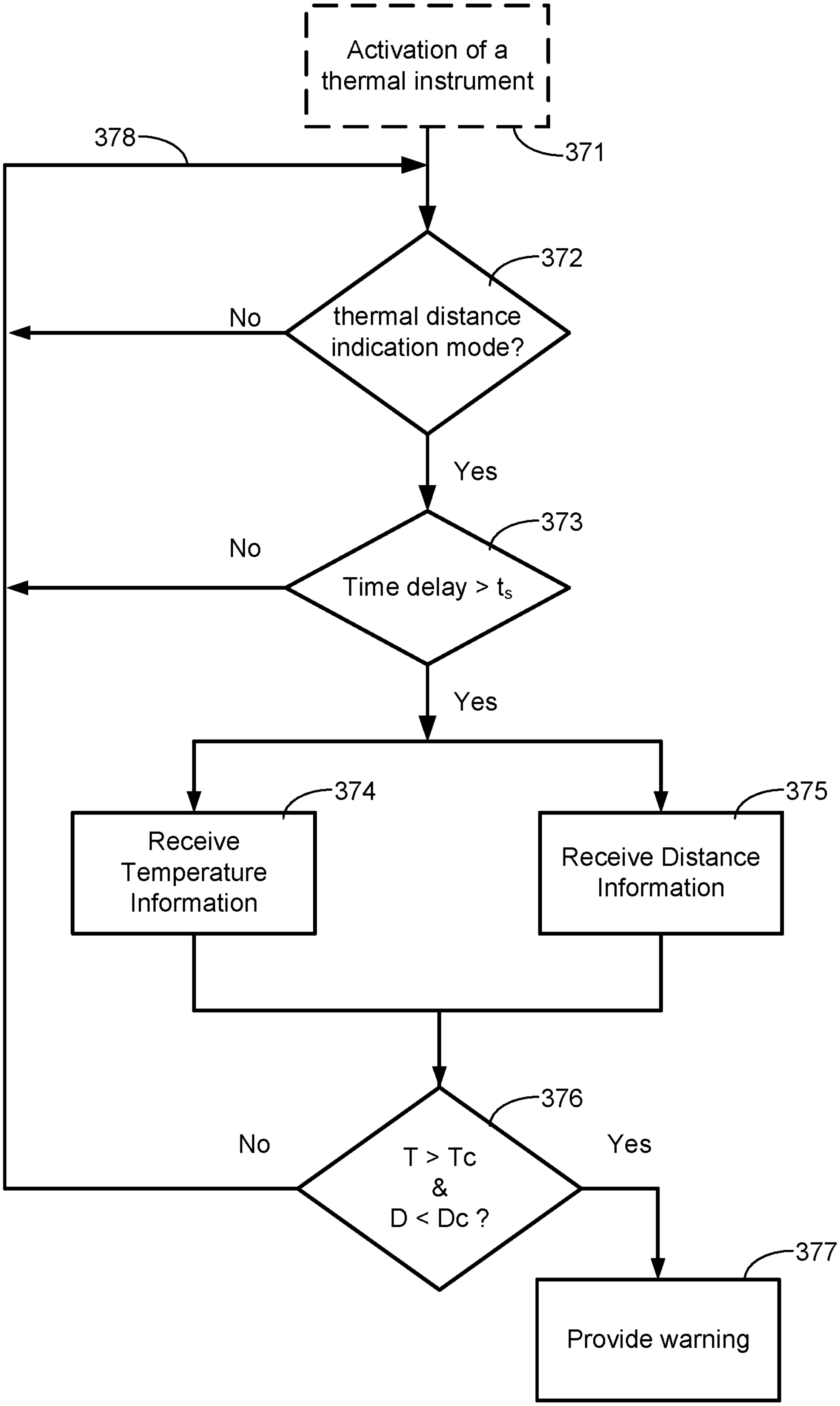
FIG. 37 is a flow diagram illustrating a method for controlling operations of a thermal distance warning in accordance with some embodiments.

FIG. 37 is a flow diagram 370 illustrating a method for controlling operations of a thermal distance warning in accordance with some embodiments.

In some cases, the method starts with a prior activation (371) of a thermal instrument, and as a result, the temperature of the thermal instrument can be high.

One or more processors of a medical system determines (372) whether the thermal distance indication mode is turned on. If the thermal distance indication mode is turned off, the one or more processors return (378) to monitor the thermal distance indication mode.

If the thermal distance indication mode is turned on, the one or more processors determine (373) whether an elapsed time is greater than a critical time (e.g., a preselected length of delay). If the time has not elapsed more than the critical time, the one or more processors return (378) to monitor the thermal distance indication mode and the elapsed time.

If the time has elapsed more than the critical time, the one or more processors receive temperature information (374) and distance information (375), and determine (376) whether a temperature of a thermal instrument is greater than a critical temperature and a distance between the thermal instrument and the surrounding tissue is less than a critical distance. If the temperature of the thermal instrument is greater than the critical temperature and the distance between the thermal instrument and the surrounding tissue is less than the critical distance, the one or more processors initiate (377) providing a warning. If the temperature of the thermal instrument is less than the critical temperature or the distance between the thermal instrument and the surrounding tissue is greater than the critical distance, the one or more processors return (378) to monitor the thermal distance indication mode and the elapsed time. The operations 374 through 377 are similar to the operations 321 through 326 and thus, their detailed descriptions are not repeated herein for brevity.

The method illustrated in FIG. 37 allow deactivating the thermal distance warning based on the thermal distance indication mode and the time delay. Some examples of how the time delay suppresses or delays the thermal distance warning are described with respect to FIGS. 38A-38C.

Figure 38A:
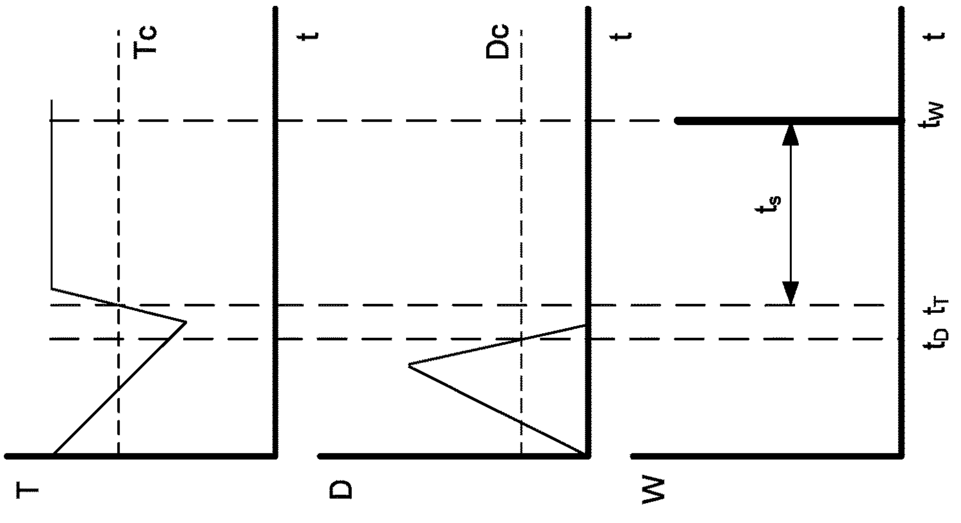
FIGS. 38A-38C are schematic diagrams illustrating operations of a thermal distance warning in accordance with some embodiments.
Figure 38B:
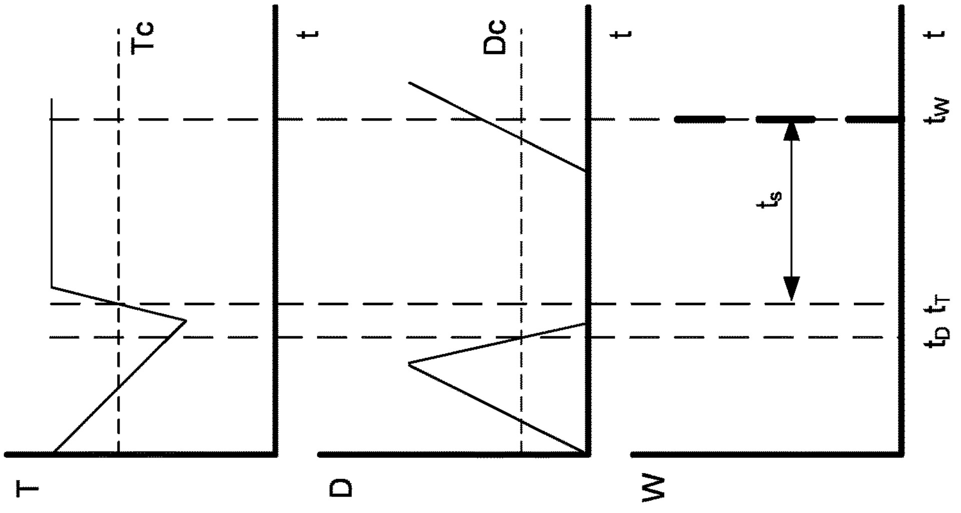
Figure 38C:
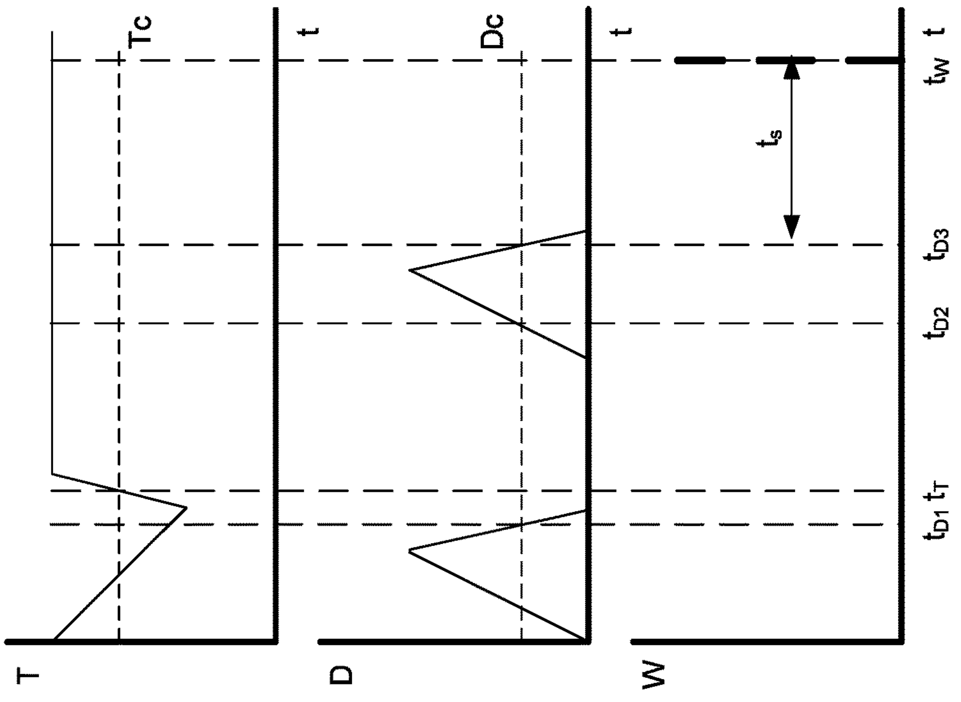

Each of FIGS. 38A-38C includes three graphs: i) a graph showing a temperature of a thermal instrument, T, as a function of a time; ii) a graph showing a distance D between the thermal instrument and the surrounding tissue, and iii) a graph showing when a warning is provided.

FIG. 38A shows that the temperature of the thermal instrument, T, decreases initially as a function of time and then increases, exceeding the critical temperature, Tc, at time $t_T$, Subsequently, T remains above Tc. In addition, the distance D between the thermal instrument and the surrounding tissue initially increases and then decreases to below the critical distance, Dc, at time $t_D$. Subsequently, the distance D remains below Dc.

In FIG. 38A, the latter of $t_D$ and $t_T$ (in this case, $t_T$) is when both temperature and distance conditions are satisfied, and the medical system monitors the elapsed time from the latter of $t_D$ and $t_T$. When the elapsed time matches the set length of delay, $t_S$, the medical system provides a warning at $t_W$.

FIG. 38B is similar to FIG. 38A, except that the distance D between the thermal instrument and the surrounding tissue rises above the critical distance, Dc, before the elapsed time matches the set length of delay, $t_S$. In some embodiments, the medical system forgoes providing a warning. For example, the medical system monitors the temperature of the thermal instrument, T, and the distance between the thermal instrument and the surrounding tissue, D, and forgoes providing the warning if the temperature T falls below the critical temperature, Tc, or if the distance D increases above the critical distance, Dc. In some embodiments, the medical system delays the warning but provides the warning after the set length of delay, $t_S$, from when both conditions were satisfied.

FIG. 38C illustrates a scenario where the temperature of the thermal instrument, T, decreases initially as a function of time and then increases, exceeding the critical temperature, Tc, at time $t_T$, Subsequently, T remains above Tc. In addition, the distance D between the thermal instrument and the surrounding tissue initially increases and then decreases to below the critical distance, Dc, at time $t_{D1}$. However, the distance D increases above the critical distance Dc at time $t_{D2}$, before the elapsed time matches the set length of delay, $t_S$. Thus, the medical system does not provide a warning after the set length of delay, $t_S$. Subsequently, the distance D falls below the critical distance Dc at time $t_{D3}$. The medical system monitors the elapsed time from the time $t_{D3}$, and when the elapsed time matches the set length of delay, $t_S$, the medical system provides a warning at time $t_W$.

Figure 39:
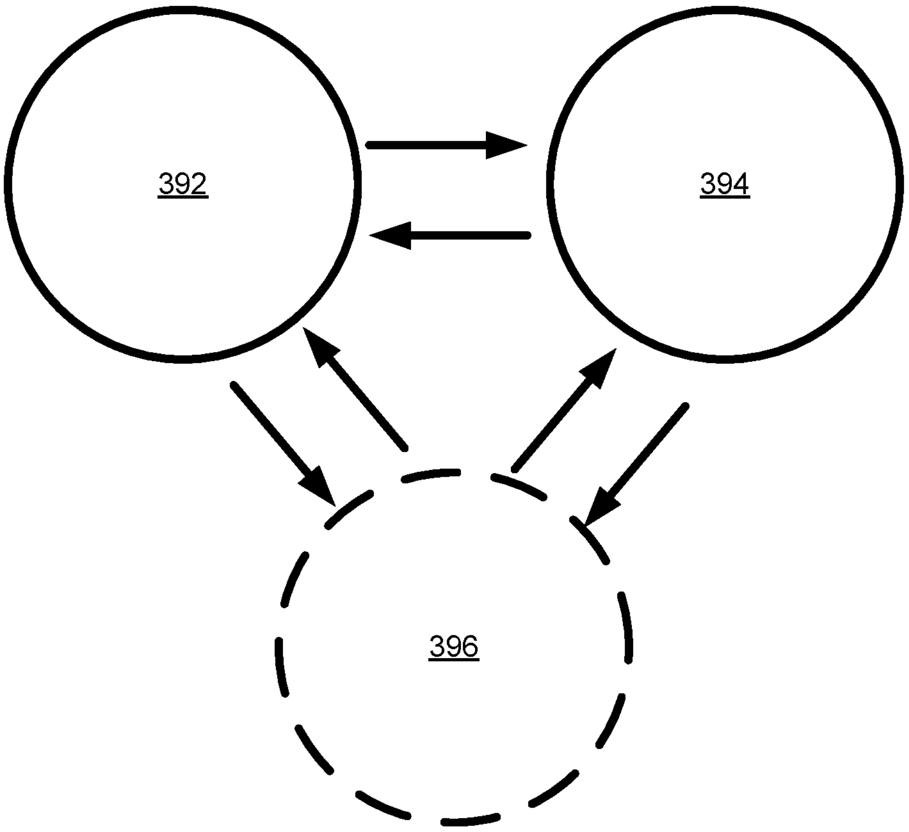
FIG. 39 is a state diagram illustrating states of a medical system in connection with operations of a thermal distance indicator in accordance with some embodiments.

FIG. 39 is a state diagram illustrating states of a medical system in connection with operations of a thermal distance indicator in accordance with some embodiments.

In some embodiments, the state machine of the medical system is described in connection with two states: (i) the thermal distance indication off state 392 (also called the thermal distance indication off mode) and (ii) the thermal distance indication on state 394 (also called the thermal distance indication on mode). As described with respect to FIGS. 36A and 36B, the medical system may switch between the thermal distance indication off state 392 and the thermal distance indication on state 394 in response to a user input (e.g., on a user interface).

In some embodiments, the state machine of the medical system also has a third state, (iii) the thermal instrument activation state 396 (also called the thermal instrument activation mode), in which the thermal instrument is activated to deliver energy to the tissue adjacent to the thermal instrument. In some embodiments, the medical system enters the third state in response to a user input (e.g., an input by a physician operator) to activate the thermal instrument. In some embodiments, the medical system stores information identifying the state of the medical system prior to entering the third state, and returns to the previous state upon determining that the user input to activate the thermal instrument has ceased to be detected.

3. Implementing Systems and Terminology

Figure 40:
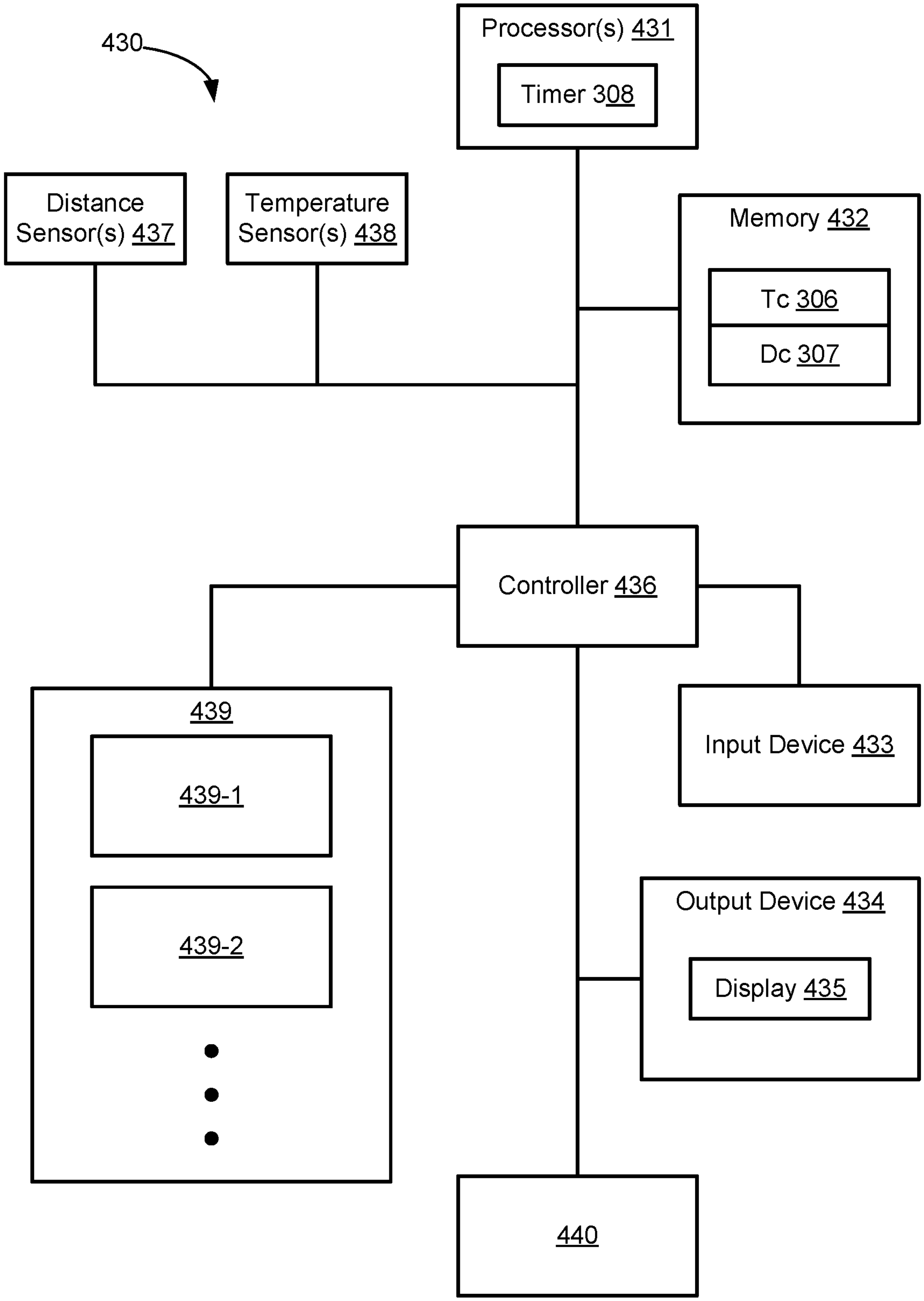
FIG. 40 is a schematic diagram illustrating electrical components of a medical system in accordance with some embodiments.

FIG. 40 is a schematic diagram illustrating electrical components of a medical system 430 in accordance with some embodiments.

Figure 41:
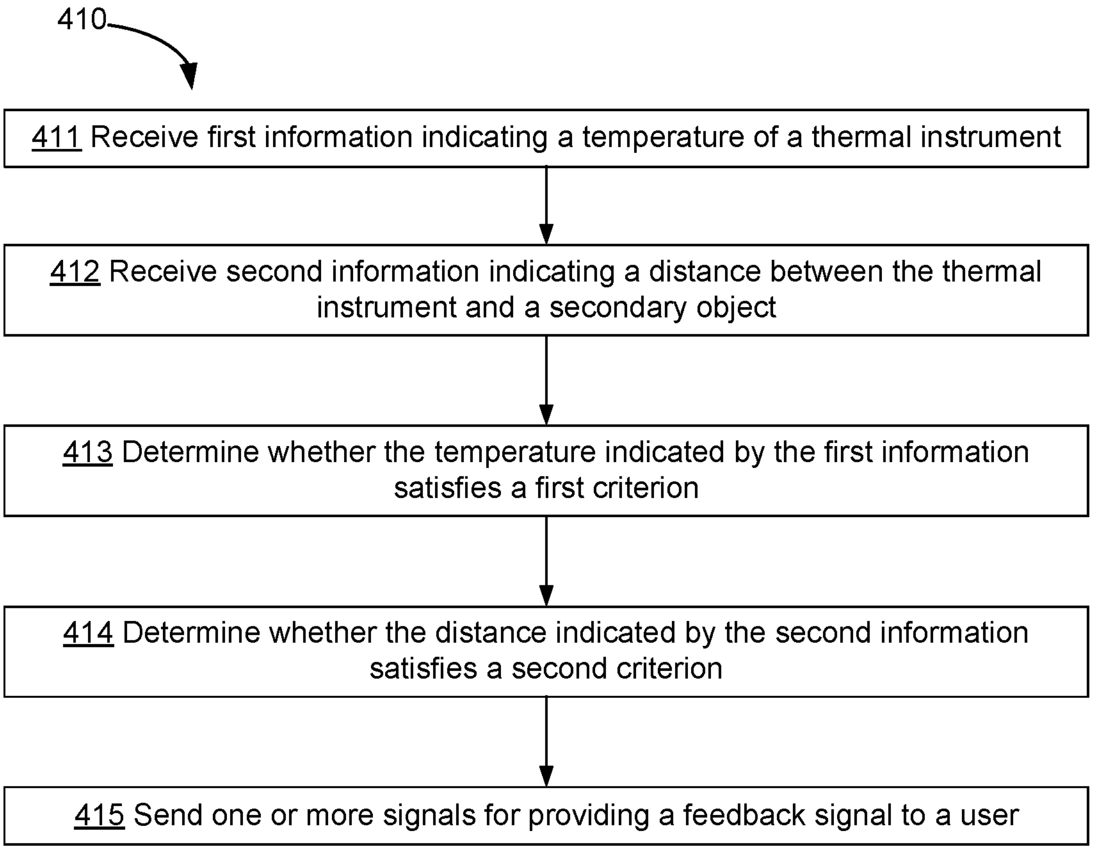
FIG. 41 is a flow diagram illustrating a method for providing a thermal distance warning in accordance with some embodiments.
Figure 42:
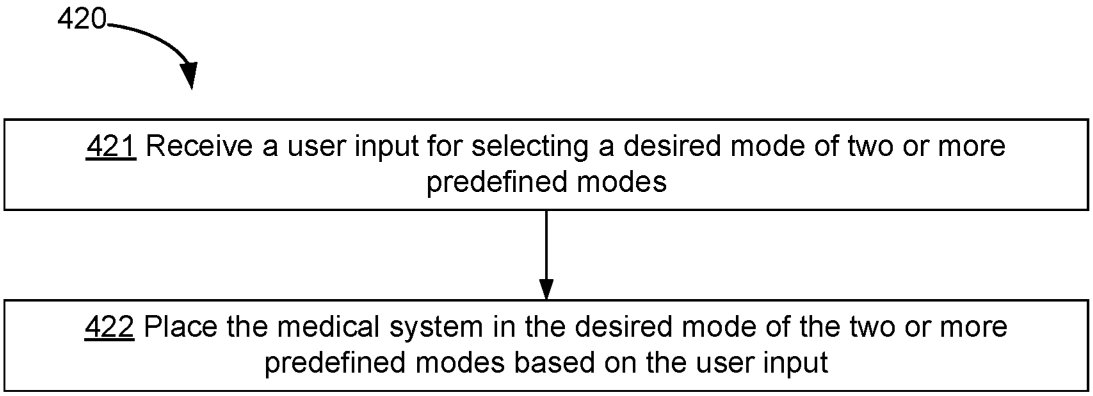
FIG. 42 is a flow diagram illustrating a method for controlling operations of a thermal distance warning in accordance with some embodiments.

The medical system 430 includes one or more processors 431, which are in communication with a computer readable storage medium 432 (e.g., computer memory devices, such as random-access memory, read-only memory, static random-access memory, and non-volatile memory, and other storage devices, such as a hard drive, an optical disk, a magnetic tape recording, or any combination thereof) storing instructions for performing any methods described herein (e.g., operations described with respect to FIGS. 41 and 42). In some embodiments, the one or more processors 431 are also in communication with an input/output controller 436 (via a system bus or any electrical circuit). The input/output controller 436 receives instructions and/or data from an input device (e.g., a user input device 433, such as a touch-sensitive screen, a keyboard, or a mouse) and relays the received instructions and/or data to the one or more processors 431 (e.g., with or without any translation, conversion, and/or data processing), or sensor devices (e.g., distance sensor 437 and temperature sensor 438). For example, the controller 436 may receive sensor output(s) from the sensors 437 and 438 and relay the information to the one or more processors 431. The input/output controller 436 also receives instructions and/or data from the one or more processors 431 (e.g., based on the data from the sensor(s) 437 and 438) and relays the instructions and/or data to one or more motors 439, such as first motor 439-1 and second motor 439-2 for actuating one or more robotic arms and/or end effectors, such as a thermal instrument. In some embodiments, the medical system 430 also includes, or is coupled to, an output device 434. The output device 434 may be a console capable of providing feedback to a physician operator. In some embodiments, the output device 434 includes a display device 435 for providing a visual feedback (e.g., displaying an image of a surgical site with or without a graphical overlay including a thermal distance indicator). In some embodiments, the output device 434 includes other modes of providing feedback, such as a speaker for providing an audio feedback or a haptic generator for providing a haptic feedback. In some embodiments, the instructions and/or data from the one or more processors 431 are directly transmitted to the motors 439.

The computer readable storage medium (or memory) 432 stores storing instructions for execution by the one or more processors. In some embodiments, the memory also stores the critical temperature 306 and the critical distance 307.

In some embodiments, the input/output controller 436 is coupled with a thermal instrument 440 (which may correspond to the thermal instrument 250) for activating the thermal instrument 440 in response to instruments and/or signals from the one or more processors 431.

In some embodiments, the medical system 430 includes a timer 308 (or a clock, for example in the one or more processors 431) for determining an elapsed time.

In some embodiments, the medical system 430 includes a subset of components shown in FIG. 40. In some embodiments, the medical system 430 includes additional components not shown in FIG. 40.

FIG. 41 is a flow diagram illustrating a method 410 for providing a thermal distance warning in accordance with some embodiments. In some embodiments, the method 410 is performed by a medical system (e.g., the medical system 430) that includes a thermal instrument (e.g., the thermal instrument 440), one or more processors (e.g., the one or more processors 432), and memory (e.g., the memory 432) storing instructions for execution by the one or more processors.

The medical system receives (411) first information indicating a temperature of the thermal instrument. In some embodiments, the medical system includes a temperature sensor (e.g., the temperature sensor 438) configured for measuring the temperature of the thermal instrument 440). In some embodiments, a temperature sensor is coupled to the thermal instrument to detect the temperature of the thermal instrument (e.g., the temperature sensor 304 coupled to the thermal instrument 250). In some embodiments, the temperature sensor comprises a thermocouple or an infrared sensor. In some embodiments, the first information is a signal (e.g., a voltage level or an encoded signal) representing the temperature of the thermal instrument.

The medical system also receives (412) second information indicating a distance between the thermal instrument and a secondary object. The secondary object is an object that is not part of the medical system. For example, in some embodiments, the secondary object is human tissue (e.g., a tissue of a patient). In some embodiments, the second information is a signal (e.g., a voltage level or an encoded signal) representing the distance between the thermal instrument and the secondary object.

In some embodiments, the medical system further includes a scope (e.g., the scope 311). In some embodiments, the scope includes a sensor for determining the distance between the thermal instrument and the secondary object (e.g., the distance sensor 312). In some embodiments, the sensor includes a structured light sensor (e.g., a combination of the light source 316 and the distance sensor 312), a time of flight sensor (e.g., the distance sensor 302), or a LIDAR sensor.

The medical system determines (413) whether the temperature indicated by the first information satisfies a first criterion. In some embodiments, the first criterion is satisfied when the temperature meets or exceeds a first temperature threshold (e.g., the critical temperature Tc).

In some embodiments, the first temperature threshold is predefined in the memory of the medical system (e.g., the temperature threshold is pre-programmed into the medical system and stored in the memory 432 as the critical temperature Tc 306).

In some embodiments, the medical system modifies the first temperature threshold (e.g., before or during a surgical procedure). In some embodiments, the medical system presents a user interface for modifying the temperature threshold (e.g., the combined image 354 including a user interface affordance 358, such as a lever, a knob, a slider, an input field, a spinner, etc., for modifying the temperature threshold), receives a user input for modifying the temperature threshold (e.g., a mouse click while a cursor is on the user interface affordance or a touch input at a location on a touch-sensitive surface corresponding to the user interface affordance 358), and modifies the temperature threshold based on the user input.

In some embodiments, the medical system adjusts the distance threshold based on the temperature of the thermal instrument. For example, if the temperature is exceptionally high (e.g., above a second temperature threshold), the medical system increases the distance threshold (e.g., FIG. 34B). Alternatively, if the temperature is lower than a third temperature threshold, the medical system decreases the distance threshold (e.g., FIG. 34C). In some embodiments, the medical system (or the one or more processors of the medical system) selects, based on the temperature, one of three or more predefined distances as the distance threshold (e.g., a short distance for a high temperature range, a medium distance for a medium temperature range, and a long distance for a low temperature range).

The medical system also determines (414) whether the distance indicated by the second information satisfies a second criterion. In some embodiments, the second criterion is satisfied when the distance between the thermal instrument and the secondary object is less than a distance threshold (e.g., the critical distance Dc). In some embodiments, the distance threshold is predefined in the memory of the medical system (e.g., the distance threshold is pre-programmed into the medical system and stored in the memory 432 as the critical distance Dc 307).

The medical system sends (415) one or more signals for providing a feedback signal to a user. In some embodiments, the one or more signals are sent to a user console and the feedback signal includes at least one of: a visual signal or a haptic signal. For example, the one or more signals sent by the medical system may include video signals sent to a display device for presenting a warning user interface or an image including a warning user interface object. In another example, the one or more signals sent by the medical system may include audio signals sent to an audio device (e.g., a speaker) or haptic signals sent to a haptic device.

In some embodiments, the feedback signal includes a visual signal in the form of a graphical overlay (e.g., a graphical overlay that is laid over an image or a video of a surgical site). For example, the feedback signal may be the combined image 354 that includes the image 350 of the surgical site and the graphical representation 352 of the thermal distance indicator.

FIG. 42 is a flow diagram illustrating a method 420 for controlling operations of a thermal distance warning in accordance with some embodiments. In some embodiments, the method 420 is performed by a medical system (e.g., the medical system 430) that includes a thermal instrument (e.g., the thermal instrument 440), one or more processors (e.g., the one or more processors 432), and memory (e.g., the memory 432) storing instructions for execution by the one or more processors.

The medical system receives (421) a user input for selecting a desired mode of two or more predefined modes (e.g., the first mode, such as the thermal distance indication "on" mode, or a second mode, such as the thermal distance indication "off" mode). This allows a user to manually activate or deactivate the thermal distance warning notification.

The medical system places (422) the medical system in the desired mode of the two or more predefined modes based on the user input. While the desired mode is a first mode of the two or more predefined modes (e.g., while the medical system is in the first mode), one or more signals for providing a feedback signal (e.g., a thermal distance warning notification) to a user are sent. For example, the medical system sends the one or more signals to a display device for providing a visual feedback.

The one or more signals are based on a temperature of a thermal instrument and a distance between the thermal instrument and a secondary object. For example, the medical system provides one or more signals for providing a thermal distance warning when the temperature of the thermal instrument is above a critical temperature and the distance between the thermal instrument and the secondary object is less than a critical distance. In another example, the medical system provides one or more signals for providing a user interface without the thermal distance warning when the temperature of the thermal instrument is below the critical temperature or the distance between the thermal instrument and the secondary object is greater than a critical distance.

In some embodiments, the medical system sends one or more signals to a display device for presenting a user interface for receiving the user input for selecting a desired mode of the two or more predefined modes (e.g., the medical system sends one or more signals to the display device for presenting the user interface 360 so that the user can interact with the displayed state indicator to activate or deactivate the thermal distance indication mode).

In some embodiments, the display device is part of the medical system. In some embodiments, the medical system is coupled to the display device, which is not part of the medical system.

In some embodiments, the medical system switches from the first mode to a second mode in accordance with a first user input (e.g., a user input that turns a physical knob or a knob displayed in a user interface from the "on" mode to the "off" mode), and switches from the second mode to the first mode in accordance with a second user input (e.g., a user input that turns the physical knob or the knob displayed in the user interface from the "off" mode to the "on" mode). In some embodiments, the first user input or the second user input is a keyboard input. In some embodiments, the first user input or the second user input is a user input on a physical switch. In some embodiments, the first user input or the second user input is a mouse click. In some embodiments, the medical system includes a touch-sensitive surface and the first user input or the second user input is an input on the touch-sensitive surface. In some embodiments, the medical system is coupled to a touch-sensitive surface (e.g., a touch-sensitive display), which is not part of the medical system, for receiving the user input.

In some embodiments, the one or more signals for providing the feedback signal include signals corresponding to a graphical overlay including a warning (for display in a display device) in connection with (e.g., in accordance with, or in response to) a determination that the temperature of the thermal instrument exceeds a temperature threshold and the distance between the thermal instrument and the secondary object is less than a distance threshold. For example, the combined image displayed on the display device may include the thermal distance indicator with a warning, as illustrated in FIG. 33C, when the temperature of the thermal instrument exceeds the temperature threshold and the distance between the thermal instrument and the secondary object is less than the distance threshold.

In some embodiments, the medical system provides a user interface for selecting a desired mode of the two or more predefined modes (e.g., the user interface 360 that includes the state indicator 362).

In some embodiments, the user interface also includes a time delay affordance (e.g., the delay time indicator 368) for selecting a delay duration in providing the feedback signal. This allows a user to manually set the delay duration.

In some embodiments, the one or more signals for providing the feedback signal are delayed by a delay duration (e.g., from a moment when the temperature of the thermal instrument is determined to exceed a temperature threshold and the distance between the thermal instrument and the secondary object is determined to be less than a distance threshold, such as $t_T$ in FIG. 38A). In some embodiments, the medical system includes a timer (e.g., the timer 308), and the medical system determines, with the timer, a period of time elapsed from the moment when the temperature of the thermal instrument is determined to exceed a temperature threshold and the distance between the thermal instrument and the secondary object is less than a distance threshold. In some embodiments, the medical system determines, with the timer, a period of time during which the moment from the temperature of the thermal instrument is determined to exceed a temperature threshold and the distance between the thermal instrument and the secondary object is less than a distance threshold. In some embodiments, the one or more signals for providing the feedback signal are sent in accordance with a determination that the period of time, during which the temperature of the thermal instrument exceeds the temperature threshold and the distance between the thermal instrument and the secondary object is less than the distance threshold, meets or exceeds the delay duration (e.g., the warning is provided the delay duration $t_S$ after the moment when both temperature and distance conditions were satisfied, namely at $t_T$, as shown in FIG. 38A). In some embodiments, the one or more signals for providing the feedback signal are sent further in accordance with a determination that the temperature of the thermal instrument has exceeded the temperature threshold for the delay duration and a determination that the distance between the thermal instrument and the secondary object has been less than the distance threshold for the delay duration.

In some embodiments, the determination whether the temperature of the thermal instrument exceeds the temperature threshold and whether the distance between the thermal instrument and the secondary object is less than the distance threshold is delayed by the delay duration from entering the first mode (e.g., from the second mode or a third mode in which the thermal instrument is activated). For example, the medical system may forgo monitoring the temperature of the thermal instrument and the distance between the thermal instrument and the surrounding tissue during the delay duration (e.g., from the moment when the medical system enters the first mode from another mode, such as the second mode).

In some embodiments, the delay duration is 1, 2, 3, 4, 5, 6, 7, 8, 9, or 10 seconds or a value within an interval between any two of the aforementioned values. In some embodiments, the delay duration is 3 or more seconds.

In some embodiments, the medical system delays sending the one or more signals for providing the feedback signal by a delay duration. For example, the medical system may send the one or more signals for providing the feedback after the delay duration, instead of forgoing sending the one or more signals for providing the feedback during the delay duration. In some embodiments, the medical system delays sending the one or more signals for providing the feedback signal from when the temperature of the thermal instrument is determined to exceed the temperature threshold and the distance between the thermal instrument and the secondary object is determined to be less than the distance threshold by the delay duration.

In some embodiments, the medical system, while in a second mode (e.g., the thermal distance indicator "off" mode), that is distinct from the first mode, of the two or more predefined modes, forgoes sending one or more signals for providing a feedback signal (e.g., a warning notification) based on a temperature of a thermal instrument and a distance between the thermal instrument and a secondary object (e.g., the medical system does not provide the thermal distance indicator while the medical system is in the thermal distance indicator off mode, independently of the temperature of the thermal instrument and the distance between the thermal instrument and the secondary object). In some embodiments, the medical system, while in the second mode, forgoes monitoring the temperature of the thermal instrument and forgoes monitoring the distance between the thermal instrument and the secondary object.

In some embodiments, the medical system switches to a third mode (e.g., the thermal instrument activation mode 396) in response to receiving one or more signals for activating the thermal instrument (e.g., electrical signals corresponding to a user input requesting activation of the thermal instrument for delivering energy to a tissue), and switches to the first mode or a second mode in accordance with a determination that the one or more signals for activating the thermal instrument have ceased. In some embodiments, the medical system, in response to a user input requesting activation of the thermal instrument (e.g., press on a button on a user input device), switches from the first mode to a third mode, and sends one or more activation signals to activate the thermal instrument. In some embodiments, the medical system ceases to send the one or more activation signals to activate the thermal instrument in accordance with a determination that the user input requesting activation of the thermal instrument has ceased. In some embodiments, the medical system switches from the third mode to the first mode or the second mode in accordance with the determination that the user input requesting activation of the thermal instrument has ceased.

In some embodiments, the medical system, in accordance with a determination that the temperature of the thermal instrument does not exceed the temperature threshold or a determination that the distance between the thermal instrument and the secondary object is equal to, or greater than, the distance threshold, forgoes sending the one or more signals for providing the feedback signal indicating a thermal distance warning.

In some embodiments, the medical system repeats receiving the first information (at different times), receiving the second information, determining whether the temperature of the thermal instrument exceeds the temperature threshold, and determining whether the distance between the thermal instrument and the secondary object is less than the distance threshold. For example, the medical system returns (378) to receive the temperature information and the distance information and continues to monitor whether the temperature of the thermal instrument exceeds the critical temperature and whether the distance between the thermal instrument and the surrounding tissue is less than the critical distance.

Implementations disclosed herein provide systems, methods and apparatus associated with dynamic visual indicators configured for use with robotic medical systems.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

Any phrases referencing specific computer-implemented processes/functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A non-transitory computer readable storage medium storing instructions for execution by one or more processors of a medical system, the stored instructions including instructions for:

displaying, via a viewer, an image depicting a representation of a thermal instrument and an image overlay associated with the thermal instrument, wherein the image overlay indicates a type of the thermal instrument;

activating a first mode associated with a thermal distance indication for the medical system; and while the medical system is in the first mode:

in response to a user input requesting activation of the thermal instrument, sending one or more activation signals to activate the thermal instrument;

receiving first information indicating a temperature of the thermal instrument;

receiving second information indicating a distance between the thermal instrument and a secondary object;

determining whether the temperature of the thermal instrument exceeds a temperature threshold;

determining whether the distance between the thermal instrument and the secondary object is less than a distance threshold;

when the temperature of the thermal instrument exceeds the temperature threshold and the distance between the thermal instrument and the secondary object is less than the distance threshold, updating at least one of the representation of the thermal instrument or the image overlay associated with the thermal instrument to indicate that the temperature of the thermal instrument exceeds the temperature threshold;

delaying the updating of the at least one of the representation of the thermal instrument or the image overlay associated with the thermal instrument by a delay duration, the delay duration beginning when the temperature of the thermal instrument is determined to exceed the temperature threshold and the distance between the thermal instrument and the secondary object is determined to be less than the distance threshold; and ceasing to send the one or more activation signals to deactivate the thermal instrument in response to determining that the user input requesting the activation of the thermal instrument has ceased.

2. The non-transitory computer readable storage medium of claim 1, wherein the updating of the at least one of the representation of the thermal instrument or the image overlay associated with the thermal instrument is performed when the temperature of the thermal instrument has remained in excess of the temperature threshold for the delay duration and the distance between the thermal instrument and the secondary object has remained less than the distance threshold for the delay duration.

3. The non-transitory computer readable storage medium of claim 1, wherein the stored instructions include instructions for restarting the delay duration upon determining that the distance between the thermal instrument and the secondary object has increased above the distance threshold before the delay duration has elapsed, and wherein the updating of the at least one of the representation of the thermal instrument or the image overlay associated with the thermal instrument is performed when the distance between the thermal instrument and the secondary object has remained less than the distance threshold for the delay duration subsequent to the restarting of the delay duration.

4. The non-transitory computer readable storage medium of claim 1, wherein the stored instructions include instructions for updating the at least one of the representation of the thermal instrument or the image overlay associated with the thermal instrument to indicate that the temperature of the thermal instrument does not exceed the temperature threshold when the temperature of the thermal instrument does not exceed the temperature threshold or when the distance between the thermal instrument and the secondary object is equal to, or greater than, the distance threshold.

5. The non-transitory computer readable storage medium of claim 1, wherein the delay duration comprises a predetermined value.

6. A method performed by a medical system, comprising:

receiving a user input indicating a selected delay duration;

receiving a user input requesting activation of a thermal instrument;

sending one or more activation signals to activate the thermal instrument, the one or more activation signals resulting in an increase in a temperature of an end effector of the thermal instrument;

displaying, via a viewer, an image depicting a representation of the thermal instrument and an image overlay associated with the thermal instrument, wherein the image overlay indicates a type of the thermal instrument;

receiving first information indicating the temperature of the thermal instrument;

receiving second information indicating a distance between the thermal instrument and a secondary object; and determining whether the temperature of the thermal instrument exceeds a temperature threshold;

determining whether the distance between the thermal instrument and the secondary object is less than a distance threshold; and when the temperature of the thermal instrument exceeds the temperature threshold and the distance between the thermal instrument and the secondary object is less than the distance threshold:

updating at least one of the representation of the thermal instrument or the image overlay associated with the thermal instrument to indicate that the temperature of the thermal instrument exceeds the temperature threshold, the updating the at least one of the representation of the thermal instrument or the image overlay associated with the thermal instrument being delayed by the selected delay duration indicated by the received user input, and ceasing to send the one or more activation signals to deactivate the thermal instrument, thereby ceasing the activation of the end effector to allow the temperature of the end effector to decrease.

7. The method of claim 6, wherein the updating the at least one of the representation of the thermal instrument or the image overlay comprises shading an end effector portion of the representation of the thermal instrument according to at least one of a preset color or a preset pattern to indicate that the temperature of the thermal instrument exceeds the temperature threshold.

8. The method of claim 6, wherein the updating the at least one of the representation of the thermal instrument or the image overlay comprises adding a shaded outline around at least a portion of the representation of the thermal instrument according to at least one of a preset color or a preset pattern to indicate that the temperature of the thermal instrument exceeds the temperature threshold.

9. The method of claim 6, wherein the updating the at least one of the representation of the thermal instrument or the image overlay comprises adding a shaded outline around at least a portion of the image overlay according to at least one of a preset color or a preset pattern to indicate that the temperature of the thermal instrument exceeds the temperature threshold.

10. The method of claim 6, wherein the updating the at least one of the representation of the thermal instrument or the image overlay comprises adding a progress bar to the image overlay, wherein the progress bar indicates at least one of a remaining cool down period of the thermal instrument or the temperature of the thermal instrument.

11. The non-transitory computer readable storage medium of claim 1, wherein the delay duration comprises a user-selected value.

12. The method of claim 6, the delay in the updating the at least one of the representation of the thermal instrument or the image overlay associated with the thermal instrument beginning when the temperature of the thermal instrument is determined to exceed the temperature threshold and the distance between the thermal instrument and the secondary object is determined to be less than the distance threshold.

* * * * *